(12) United States Patent
Davis et al.

(10) Patent No.: US 11,377,663 B1
(45) Date of Patent: Jul. 5, 2022

(54) GENETIC REGULATORY ELEMENTS

(75) Inventors: Ian W. Davis, Durham, NC (US); Tedd D. Elich, Durham, NC (US)

(73) Assignee: Monsanto Technology LLC, St. Louis, MO (US)

( * ) Notice: Subject to any disclaimer, the term of this patent is extended or adjusted under 35 U.S.C. 154(b) by 691 days.

(21) Appl. No.: 13/599,254

(22) Filed: Aug. 30, 2012

Related U.S. Application Data

(60) Provisional application No. 61/529,001, filed on Aug. 30, 2011, provisional application No. 61/535,109, filed on Sep. 15, 2011.

(51) Int. Cl.
*C12N 15/82* (2006.01)

(52) U.S. Cl.
CPC .............................. *C12N 15/8216* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford | |
| 5,240,855 A | 8/1993 | Tomes | |
| 5,316,931 A | 5/1994 | Donson | |
| 5,322,783 A | 6/1994 | Tomes | |
| 5,324,646 A | 6/1994 | Buising | |
| 5,380,831 A | 1/1995 | Adang | |
| 5,405,765 A | 4/1995 | Vasil | |
| 5,436,391 A | 7/1995 | Fujimoto | |
| 5,563,055 A | 10/1996 | Townsend | |
| 5,589,367 A | 12/1996 | Donson | |
| 5,605,793 A | 2/1997 | Stemmer | |
| 5,736,369 A | 4/1998 | Bowen | |
| 5,837,458 A | 11/1998 | Minshull | |
| 5,866,785 A | 2/1999 | Donson | |
| 5,879,918 A | 3/1999 | Tomes | |
| 5,886,244 A | 3/1999 | Tomes | |
| 5,889,190 A | 3/1999 | Donson | |
| 5,889,191 A | 3/1999 | Turpen | |
| 5,932,782 A | 8/1999 | Bidney | |
| 6,376,744 B1 * | 4/2002 | Maliga | C12N 15/8214 435/320.1 |
| 7,645,919 B2 | 1/2010 | Anderson | |
| 2003/0199681 A1 * | 10/2003 | Fincher | C12N 9/1092 536/23.2 |
| 2007/0204367 A1 * | 8/2007 | Flasinski | C12N 15/8216 800/278 |
| 2008/0141585 A1 | 6/2008 | Benfey | |
| 2013/0117883 A1 * | 5/2013 | Elich | C12N 15/8216 800/278 |

FOREIGN PATENT DOCUMENTS

| | | |
|---|---|---|
| EP | 1877575 | 9/2011 |
| EP | 2521439 | 11/2012 |
| WO | 94/000977 | 1/1994 |
| WO | 95/06722 | 3/1995 |
| WO | 00/28058 | 5/2000 |
| WO | 2006/110852 | 10/2006 |
| WO | 2011/084370 | 7/2011 |
| WO | 2012/006426 | 1/2012 |
| WO | 20121077020 | 6/2012 |
| WO | 2012/101191 | 8/2012 |

OTHER PUBLICATIONS

Tremousaygue et al., Plant J 20(5):553-61 (1999).*
Fourgoux-Nicol et al., Plant Mol Biol 40:857-72 (1999).*
Wahl et al., Meth Enzymol 152:399-407 (1987).*
Potenza et al., In Vitro Cell Dev Biol Plant 40:1-22 (2004).*
Saha et al., In Silico Biol 7(1):7-19 (2007).*
Rose, Curr Top Microbiol Immunol, 326:277-90 (2008).*
Liu et al., Nat Rev Genet 14:781-93 (2013).*
Axelos et al., Mol Gen Genet 219:106-12 (1989).*
Regad et al., J Mol Biol 239(2):163-69 (1994).*
McIntosh et al., Genome 54(9):738-51 (2011).*
Trémousaygue et al., Plant J 33:957-66 (2003).*
Thatcher et al., J Biol Chem 282(39):28915-28 (2007).*
Potenza et al., In Vitro Cell Dev Biol Plant 40:1-22, 2 (2004).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Axelos et al., Mol Gen Genet 219:106-12, 106 (1989).*
Saha et al., In Silico Biol 7(1):7-19, 8 (2007.*
Tsien (1998) Annu Rev Biochem 67:509-44.*
Luo et al., Promoter recognition based on the Interpolated Markov Chains optimized via simulated annealing and genetic algorithm, Pattern Recognition Letters, 2006, 27: 1031-1036.
Venter, M., Synthetic promoters: genetic control through cis engineering, TRENDS in Plant Science, 2007, 12:3, 118-124.
Pilpel et al., Identifying regulatory networks by combinatorial analysis of promoter elements, Genetics, 2001, 21: 153-159.
Holt et al., ModuleFinder and CoReg: alternative tools for linking gene expression modules with promoter sequences motifs to uncover gene regulation mechanisms in plants, Plant Methods, 2006, 2:8, 15 pages.
Damien, et al., Gibbs sampling for Bayesian non-conjugate and hierarchical models by using auxiliary variables, Journal Royal Statistical Society, 1999, 61: Part 2, 331-344.
United States Patent and Trademark Office, Office Action dated Jun. 2, 2015, for U.S. Appl. No. 13/599,255, 20 pages.
Halpin (2005) Plant Biotech. J. 3:141-155.
Rose et al. (2008) Plant Cell 20:543-551.
Stemmer (1994) PNAS 91:10747-10751.
Stemmer (1994) Nature 370:389-391.
Moore et al. (1997) J. Mol. Biol. 272:336-347.
Zhang et al. (1997) PNAS 94:4504-4509.
Crameri et al. (1998) Nature 391:288-291.

(Continued)

*Primary Examiner* — Russell T Boggs
(74) *Attorney, Agent, or Firm* — Harness, Dickey & Pierce, P.L.C.

(57) ABSTRACT

Polynucleotides comprising genetic regulatory elements, as well as constructs, host cells, and transgenic organisms comprising the same are described. The polynucleotides can control the expression of an operably linked gene in a host cell or organism, such as a plant cell or a plant. Methods of using the polynucleotide to control the expression of an operably linked gene of interest in a plant or plant cell are further provided.

26 Claims, 1 Drawing Sheet

Specification includes a Sequence Listing.

(56) References Cited

OTHER PUBLICATIONS

Hush et al. (1994) The Journal of Cell Science 107:775-784.
Innis et al., eds. (1990) PCR Protocols: A Guide to Methods and Applications (Academic Press, New York).
Clough and Bent (1998) Plant J. 16:735.
Sheen, J. 2002. A transient expression assay using maize mesophyll protoplasts. http://genetics.mgh.harvard.edu/sheenweb/.
Karlin and Altschul (1990) PNAS 87:2264.
Karlin and Altschul (1993) PNAS 90:5873-5877.
Altschul et al. (1990) J. Mol. Biol. 215:403.
Altschul et al. (1997) Nucleic Acids Res. 25:3389.
Myers and Miller (1988) CABIOS 4:11-17.
Edgar (2004) Nucleic Acids Res. 32(5):1792-1797.
Guerineau et al. (1991) Mol. Gen. Genet. 262:141-144.
Proudfoot (1991) Cell 64:671-674.
Sanfacon et al. (1991) Genes Dev. 5:141-149.
Mogen et al. (1990) Plant Cell 2:1261-1272.
Munroe et al. (1990) Gene 91:151-158.
Ballas et al. (1989) Nucleic Acids Res. 17:7891-7903.
Joshi et al. (1987) Nucleic Acids Res. 15:9627-9639.
Campbell and Gowri (1990) Plant Physiol. 92:1-11.
Murray et al. (1989) Nucleic Acids Res. 17:477-498.
Elroy Stein et al. (1989) PNAS USA 86:6126 6130.
Gallie et al. (1995) Gene 165(2):233-238.
Allison, Virology 154:9 20, (1986).
Macejak et al. (1991) Nature 353:90 94.
Jobling et al. (1987) Nature 325:622 625.
Gallie et al. (1989) in Molecular Biology of RNA, ed. Cech (Liss, New York), pp. 237-256.
Lommel et al. (1991) Virology 81:382 385.
Della Cioppa et al. (1987) Plant Physiol. 84:965 968.
Su et al. (2004) Biotechnol Bioeng. 85:610-9.
Fetter et al. (2004) Plant Cell 16:215-28.
Bolte et al. (2004) J. Cell Science 117:943-54.
Kato et al. (2002) Plant Physiol. 129:913-42.
Hepler et al. (1994) PNAS 91: 2176-2180.
Yarranton (1992) Curr. Opin. Biotech. 3:506-511.
Christopherson et al. (1992) PNAS 89:6314-6318.
Yao et al. (1992) Cell 71:63-72.
Reznikoff (1992) Mol. Microbiol. 6:2419-2422.
Barkley et al. (1980) in The Operon, pp. 177-220.
Hu et al. (1987) Cell 48:555-566.
Brown et al. (1987) Cell 49:603-612.
Figge et al. (1988) Cell 52:713-722.
Deuschle et al. (1989) PNAS 86:5400-5404.
Fuerst et al. (1989) PNAS 86:2549-2553.
Deuschle et al. (1990) Science 248:480-483.
Roberts (2011) The Use of Functional Genomics in Synthetic Promoter Design, 375-396. In Computational Biology and Applied Bioinformatics: Book Chapter (and references therein).
Edgar, Muscle: a multiple sequence alignment method with reduced time and space complexity, BMC Bioinformatics, 2004, 113-132.
Gossen (1993) Ph.D. Thesis, University of Heidelberg.
Reines et al. (1993) PNAS 90:1917-1921.
Labow et al. (1990) Mol. Cell. Biol. 10:3343-3356.
Zambretti et al. (1992) PNAS 89:3952-3956.
Baim et al. (1991) PNAS 88:5072-5076.
Wyborski et al. (1991) Nucleic Acids Res. 19:4647-4653.
Hillenand-Wissman (1989) Topics Mol. Struc. Biol. 10:143-162.
Degenkolb et al. (1991) Antimicrob. Agents Chemother. 35:1591-1595.
Kleinschnidt et al. (1988) Biochemistry 27:1094-1104.
Nomura et al. (1986) Plant Sci. 44:53-58.
Crossway et al. (1986) Mol Gen. Genet. 202:179-185.
Oliva et al. (1992) Antimicrob. Agents Chemother. 36:913-919.
Hlavka et al. (1985) Handbook of Experimental Pharmacology, vol. 78 ( Springer-Verlag, Berlin).
Gill et al. (1988) Nature 334:721-724.
An, G. et al. (1986) Plant Pysiol., 81:301-305.
Fry, J., et al. (1987) Plant Cell Rep. 6:321-325.
Block, M. (1988) Theor. Appl Genet.76:767-774.
Hinchee, et al. (1990) Stadler. Genet. Symp. 203212.203-212.
Cousins, et al. (1991) Aust. J. Plant Physiol. 18:481-494.
Chee, P. P. and Slightom, J. L. (1992) Gene 118:255-260.
Christou, et al. (1992) Trends. Biotechnol. 10:239-246.
D'Halluin, et al. (1992) Bio/Technol. 10:309-314.
Dhir, et al. (1992) Plant Physiol. 99:81-88.
Casas et al. (1993) PNAS 90:11212-11216.
Christou, P. (1993) In Vitro Cell. Dev. Biol.-Plant; 29P:119-124.
Davies, et al. (1993) Plant Cell Rep. 12:180-183.
Dong, J. A. and Mchughen, A. (1993) Plant Sci. 91:139-148.
Franklin, C. I. and Trieu, T. N. (1993) Plant. Physiol. 102:167.
Golovkin, et al. (1993) Plant Sci. 90:41-52.
Guo Chin Sci. Bull. 38:2072-2078.
Asano, et al. (1994) Plant Cell Rep. 13.
Ayeres N. M. And Park, W. D. (1994) Crit. Rev. Plant. Sci. 13:219-239.
Barcelo, et al. (1994) Plant. J. 5:583-592.
Becker, et al. (1994) Plant. J. 5:299-307.
Borkowska et al. (1994) Acta. Physiol Plant. 16:225-230.
Christou, P. (1994) Agro. Food. Ind. Hi Tech. 5: 17-27.
Eapen et al. (1994) Plant Cell Rep. 13:582-586.
Hartman, et al. (1994) Bio-Technology 12: 919923.
Ritala, et al. (1994) Plant. Mol. Biol. 24:317-325.
Wan, Y. C. and Lemaux, P. G. (1994) Plant Physiol. 104:3748.
Bilang et al. (1991) Gene 100: 247-250.
Scheid et al., (1991) Mol. Gen. Genet. 228: 104-112.
Guerche et al., (1987) Plant Science 52: 111-116.
Neuhause et al., (1987) Theor. Appl Genet. 75: 30-36.
Klein et al., (1987) Nature 327: 70-73.
Howell et al., (1980) Science 208:1265.
Horsch et al., (1985) Science 227: 1229-1231.
DeBlock et al., (1989) Plant Physiology 91: 694-701.
Methods for Plant Molecular Biology (Weissbach and Weissbach, eds.) Academic Press, Inc. (1988).
Methods in Plant Molecular Biology (Schuler and Zielinski, eds.) Academic Press, Inc. (1989).
Crossway et al. (1986) Biotechniques 4:320 334.
Riggs et al. (1986) PNAS 83:5602 5606.
Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin).
McCabe et al. (1988) Biotechnology 6:923 926.
Weissinger et al. (1988) Ann. Rev. Genet. 22:421 477.
Sanford et al. (1987) Particulate Science and Technology 5:27 37.
Christou et al. (1988) Plant Physiol. 87:671 674.
Finer and McMullen (1991) In Vitro Cell Dev. Biol. 27P:175-182.
Singh et al. (1998) Theor. Appl. Genet. 96:319-324.
Datta et al. (1990) Biotechnology 8:736 740.
Klein et al. (1988) PNAS 85:4305 4309.
Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin).
Klein et al. (1988) Plant Physiol. 91:440 444.
Fromm et al. (1990) Biotechnology 8:833 839.
Hooykaas-Van Slogteren et al. (1984) Nature (London) 311:763-764.
Bytebier et al. (1987) PNAS 84:5345-5349.
De Wet et al. (1985) in The Experimental Manipulation of Ovule Tissues, ed. Chapman et al. (Longman, New York), pp. 197-209.
Kaeppler et al. (1990) Plant Cell Reports 9:415-418.
Kaeppler et al. (1992) Theor. Appl. Genet. 84:560-566.
D'Halluin et al. (1992) Plant Cell 4:1495-1505.
Li et al. (1993) Plant Cell Reports 12:250-255.
Christou and Ford (1995) Annals of Botany 75:407-413.
Ishida et al. (1996) Nature Biotechnology 14:745-750.
McCormick et al. (1986) Plant Cell Reports 5:81-84.

* cited by examiner

GENETIC REGULATORY ELEMENTS

CROSS-REFERENCE TO RELATED APPLICATIONS

This application claims the benefit of U.S. Provisional Application No. 61/529,001, filed Aug. 30, 2011 and U.S. Provisional Patent Application Ser. No. 61/535,109 filed Sep. 15, 2011, each of which are hereby incorporated by reference in its entirety for all purposes.

TECHNICAL FIELD

The invention generally relates to regulatory elements, such as promoters and expression-enhancing introns, and to polynucleotides, cells, and organisms comprising the same.

DESCRIPTION OF THE TEXT FILE SUBMITTED ELECTRONICALLY

The contents of the text file submitted electronically are incorporated herein by reference in their entirety: A computer readable format copy of the Sequence Listing (filename: 5089_103_US.txt, date recorded: Sep. 30, 2021, file size 42 kilobytes).

BACKGROUND OF THE INVENTION

The production of transgenic cells and organisms comprising a heterologous gene sequence is now routinely practiced by molecular biologists. Methods for incorporating an isolated gene sequence into an expression cassette, producing transformation vectors, and transforming many types of cells and organisms are well known. The regulation or control of expression of the heterologous gene and the protein encoded by the gene can often be critical in the development of a transgenic organism for commercial use. For example, in transgenic plants cells and whole plants comprising a heterologous gene that confers tolerance to herbicide that is normally toxic to the plant, it can be critical to have the heterologous gene expressed in a temporal and spatial manner that corresponds to when the plant is exposed to the herbicide and to what parts of the plant the herbicide normally exerts its phytotoxic effect.

A number of genetic regulatory elements are known to play a role in regulating the expression of a gene in plants and other organisms including, for example, promoters, enhancers, 5'-untranslated regions (UTRs), 3'-untranslated regions, and expression-enhancing introns. To express a transgene in a plant or organism, one or more of these genetic regulatory elements is operably linked for expression to a nucleic acid sequence or gene of interest.

Recently, it has become commonplace to introduce or "stack" multiple transgenes into a single transgenic crop plant. The stacking of multiple transgenes into a single transgenic plant has, however, proved to be problematic, particularly when the same genetic regulatory elements are used in more than one of the stacked transgenes. The use of multiple copies of the same regulatory sequence within two or more transgenes in a single plant is known to promote the activation of gene silencing mechanisms (Halpin (2005) *Plant Biotech. J.* 3:141-155). Silencing of transgenes previously showing stable expression can also be triggered 'de novo' when a new transgene is added by crossing or re-transformation if, for example, the same promoter has been used in both transgenes in an effort to promote coordinated expression (Halpin (2005) *Plant Biotech. J.* 3:141-155). Often, the use of the same promoter in multiple transgenes in a single plant is due to the lack of more than one promoter that gives the desired pattern and level of expression. For example, the Cauliflower Mosaic Virus (CaMV) 35S promoter is frequently used as the promoter in plant transgenes because it provides for high-level constitutive expression of an operably linked gene of interest. Because of a lack of suitable alternative promoters, the CaMV 35 promoter is often used to drive the high-level constitutive expression of two or more transgenes in the same plant. Thus, additional promoters and other genetic regulatory elements are needed to avoid gene silencing that might be caused by the use of a particular genetic regulatory element more than once when two, three, four, or more transgenes are stacked in a single crop plant.

SUMMARY OF THE INVENTION

The present invention provides polynucleotides comprising one or more genetic regulatory elements that can control the expression of an operably linked gene in a host cell or organism, such as a plant cell or a plant. The invention further provides transgenic cells and organisms comprising one or more of these polynucleotides.

In particular, the invention provides polynucleotides comprising genetic regulatory elements which may act as promoters and/or expression enhancing introns. For example, polynucleotides having promoter activity may comprise a nucleotide sequence selected from SEQ ID NO: 1 to 5, 15 to 20, and 42 to 50, including fragments, and variants of these sequences. Polynucleotides acting at least in part as expression-enhancing introns include, but are not limited to, polynucleotides comprising a nucleotide sequence selected from SEQ ID NO: 6 to 10 and 15 to 20, including fragments and variants of these sequences. The polynucleotides may be in the form of constructs, which may contain convenient restriction sites for inserting one or more sequences of interest. Such constructs include expression constructs that allow a polynucleotide of the invention to be operably linked to a gene of interest for expression in a cell, such as a plant cell. The invention thus, provides methods of regulating (e.g., enhancing) the expression of a gene of interest in a cell, by operably associating the gene of interest with a polynucleotide described herein, and introducing such a construct into a cell for expression.

The present invention provides polynucleotides with gene expression control properties. In various embodiments, the polynucleotides are recombinant or synthetically produced. In some embodiments, the polynucleotide comprises a fragment and/or variant of the nucleotide sequence set forth in SEQ ID NO: 1 to 5, 15 to 20, and 42 to 50, wherein the fragment and/or variant retains the same, substantially the same, or stronger promoter activity as compared to the reference sequence. As used herein, the term "substantially the same" means a level of activity within ±50% in an assay described herein, which may generally be used to assess strength of promoter activity.

In some embodiments, the variant polynucleotide comprises a nucleotide sequence having at least 70% nucleotide sequence identity to a sequence selected from SEQ ID NO: 1 to 5, 15 to 20, and 42 to 50, said nucleotide sequence having promoter activity in a plant cell. In some embodiments, the polynucleotide comprises a fragment of at least 50 contiguous bases of any one of SEQ ID NO: 1 to 5 and 42 to 50, the polynucleotide having promoter activity in a plant cell. In some embodiments, the polynucleotide comprises one or more cis-acting sequences to support basic promoter activity, including a Site II sequence (e.g., SEQ ID NO: 39), a telo box sequence (e.g., SEQ ID NO: 40), and a TATA box sequence (e.g., SEQ ID NO: 41). These elements may be positioned within the region defined by −200 and +35 with respect to the transcription start site (TSS), and in some embodiments in the region defined by −118 to +7.

For example, the polynucleotide may comprise at least one Site II sequence, at least one telo box sequence, and at least one TATA box sequence. In some embodiments, the polynucleotide comprises two or more Site II sequences, and/or two or more telo box sequences, and/or two or more TATA box sequences. These cis-acting sequences may be positioned to support their cis-acting functions in the cell. For example, the two or more Site II sequences may be positioned adjacent to or close to each other, for example, about 0, 1, 5, 10, 15, 20, 25, 30, 50 or more nucleotides apart. At least one site II sequence may be positioned in the region of −25 to −200 relative to the TSS, or within −118 to +7 relative to the TSS in some embodiments. In some embodiments, the two or more telo box sequences are positioned adjacent or close to each other, for example, about 0, 1, 5, 10, 15, 20, 25, 30, 50 or more nucleotides apart. In some embodiments, at least one telo box sequence may be positioned within the region defined by −118 to +7 or in some embodiments −85 to +35 relative to the TSS. In some embodiments, the two or more TATA box sequences are positioned adjacent or close to each other. The start of the TATA box sequence(s) may be positioned just upstream from the TSS, for example, in a region defined by −4 to −50 from the TSS.

In some embodiments, the polynucleotide comprises an expression-enhancing intron, and comprises a nucleotide sequence selected from SEQ ID NO: 6 to 10 and 15 to 20. In some embodiments, the polynucleotide comprises a fragment and/or variant of the nucleotide sequence set forth in SEQ ID NO: 6 to 10, wherein the fragments and/or variants retains the same, substantially the same, or stronger enhancer activity compared to the reference sequence. As used herein, the term "substantially the same" means a level of activity within ±50% in an assay described herein, and such assays may be used to determine the relative strength of an expression-enhancing intron.

In some embodiments, the variant polynucleotide comprises a nucleotide sequence having at least 70% nucleotide sequence identity to the nucleotide sequence selected from SEQ ID NO: 6 to 10 and 15 to 20, wherein the polynucleotide is capable of enhancing the expression of an operably linked gene of interest in a cell (e.g., a plant cell). In some embodiments, the polynucleotide comprises a fragment of any one of SEQ ID NO: 6 to 10, wherein the polynucleotide is capable of enhancing the expression of an operably linked gene of interest in a cell (e.g., a plant cell).

The polynucleotide of the invention may be double stranded, or may be single stranded. Single-stranded polynucleotides can be either strand, e.g., the polynucleotide comprising any one of SEQ ID NOS: 1-10, 15 to 20, and 42 to 50, or variant or fragment thereof, or a complement thereof. In particular, single stranded polynucleotides can find use as probes and primers for constructing or detecting polynucleotides of the invention.

In some embodiments, the variant polynucleotide or fragment hybridizes to a sequence of SEQ ID NO: 1 to 10, 15 to 20, and 42 to 50. In some embodiments, the hybridization is under stringent conditions, as described herein.

In some embodiments, the present invention provides the polynucleotides as constructs containing other elements, such as, for example, replication elements, convenient cloning sites, gene sequences for expression, sequences to drive integration of nucleotide sequences into a target genome, and/or selection elements to aid cloning and selection of polynucleotide-containing cells. In some embodiments, the construct is an expression cassette suitable for expression in a bacteria cell, a fungal cell, a plant cell, or an animal cell. In some embodiments, the expression cassette further comprises a gene of interest operably linked for expression. In some embodiments, the expression cassette comprises a polynucleotide having promoter activity (e.g., a polynucleotide of SEQ ID NOS: 1 to 5 and 42 to 50, or fragment or variant thereof), which is generally positioned upstream (that is, 5' to) a transcribed sequence of interest to provide transcriptional control. In these or other embodiments, the polynucleotide has activity as an expression-enhancing intron (e.g., a polynucleotide of SEQ ID NO: 6, 7, 8, 9, or 10, or fragment or variant thereof), and in various embodiments is positioned as a first intron in the transcribed region. In some embodiments, the polynucleotide or construct has both a region of promoter activity (e.g., comprising a sequence of SEQ ID NOS: 1 to 5 and 42 to 50, or fragment or variant thereof) as well as an expression-enhancing intron sequence (e.g., a sequence selected from SEQ ID NOS: 6 to 10, or fragment or variant thereof). For example, the polynucleotide or construct may comprise a nucleotide sequence selected from SEQ ID NOS: 15 to 20, or fragment or variant thereof. The constructs may further take the form of vectors for introducing into and/or integrating polynucleotide of the invention into host cells, including a plant cell, animal cell, fungal cell, algae, or microorganism.

The present invention further provides non-human transgenic organisms comprising a transgenic cell of the invention. In some embodiments, the transgenic organism is a plant, or part derived therefrom. In some embodiments, the plant is a monocot or a dicot. In some embodiments, the transgenic plant is selected from soybean, cotton, maize, sorghum, wheat, rice, switchgrass, sugarcane, millet, *Brachypodium*, and *Arabidopsis*, as well as others described herein.

The present invention further provides seeds of the transgenic plant, and methods of producing the hybrid seeds or plants. In some embodiments, the methods comprise crossing the plant of the present invention or the progeny plant of the present invention with a different plant of the same species, and harvesting the resultant seed.

BRIEF DESCRIPTION OF THE DRAWINGS

FIG. 1 depicts sequence alignment of functional SP3, SP4, and SP5 promoter variants and non-functional SP3, SP4, SP5 promoter variants (SEQ ID NOS: 21-38) with the original SP3, SP4, and SP5 promoter sequences at position −118 to position+7 (SEQ ID NOS: 3-5). Conserved Site II sequence, telo box sequence, and TATA box sequence are highlighted.

SEQUENCE LISTING

The nucleotide sequences listed in the accompanying sequence listing are shown using standard letter abbreviations for nucleotide bases. The nucleotide sequences follow the standard convention of beginning at the 5' end of the sequence and proceeding forward (i.e., from left to right in each line) to the 3' end. Only one strand of each nucleic acid sequence is shown, but (unless otherwise stated) the complementary strand is understood to be included by reference to the displayed strand. SEQ ID NO: 1 sets forth the nucleotide sequence of the promoter designated as SP1.

SEQ ID NO: 2 sets forth the nucleotide sequence of the promoter designated as SP2.

SEQ ID NO: 3 sets forth the nucleotide sequence of the promoter designated as SP3.

SEQ ID NO: 4 sets forth the nucleotide sequence of the promoter designated as SP4.

SEQ ID NO: 5 sets forth the nucleotide sequence of the promoter designated as SP5.

SEQ ID NO: 6 sets forth the nucleotide sequence of the intron designated as SI1.

SEQ ID NO: 7 sets forth the nucleotide sequence of the intron designated as SI2.

SEQ ID NO: 8 sets forth the nucleotide sequence of the intron designated as SI3.

SEQ ID NO: 9 sets forth the nucleotide sequence of the intron designated as SI4.

SEQ ID NO: 10 sets forth the nucleotide sequence of the intron designated as SI5.

SEQ ID NO: 11 is the nucleotide sequence of the AT4G37830 promoter of PCT/US2011/043197 (SEQ ID NO: 10 therein).

SEQ ID NO: 12 is the nucleotide sequence of the AT1G51650 promoter from PCT/US2011/043197 (SEQ ID NO: 7 therein).

SEQ ID NO: 13 is the nucleotide sequence of the AT4G37830 intron from PCT/US2011/043197 designated as IN1.

SEQ ID NO: 14 is the nucleotide sequence of the AT1G51650 intron from PCT/US2011/043197 designated as IN2.

SEQ ID NO: 15 is the nucleotide sequence of SP1 operably linked to IN2, designated as SP1/IN2.

SEQ ID NO: 16 is the nucleotide sequence of SP2 operably linked to IN1, designated as SP2/IN1.

SEQ ID NO: 17 is the nucleotide sequence of SP2 operably linked to IN2, designated as SP2/IN2.

SEQ ID NO: 18 is the nucleotide sequence of SP3 operably linked to IN1, designated as SP3/IN1.

SEQ ID NO: 19 is the nucleotide sequence of SP3 operably linked to IN2, designated as SP3/IN2.

SEQ ID NO: 20 is the nucleotide sequence of SP5 operably linked to IN1, designated as SP5/IN1.

SEQ ID NOs: 21 to 23 are the −118 to +7 nucleotide sequences of SP3 variants (SP3 bad70; SP3 bad80; and SP3 bad90, respectively) that do not substantially maintain the function of the SP3 promoter ("bad" sequences).

SEQ ID NOs: 24 to 26 are the −118 to +7 nucleotide sequences of SP3 variants (SP3 good70; SP3 good80; and SP3 good90, respectively) that substantially maintain the function of the SP3 promoter ("good" sequences).

SEQ ID NOs: 27 to 29 are the −118 to +7 nucleotide sequences of SP4 variants (SP4 bad70; SP4 bad80; and SP4 bad90, respectively) that do not substantially maintain the function of the SP4 promoter ("bad" sequences).

SEQ ID NOs: 30 to 32 are the −118 to +7 nucleotide sequences of SP4 variants (SP4 good70; SP4 good80; and SP4 good90, respectively) that substantially maintain the function of the SP4 promoter ("good" sequences).

SEQ ID NOs: 33 to 35 are the −118 to +7 nucleotide sequences of SP5 variants (SP5 bad70; SP5 bad80; and SP5 bad90, respectively) that do not substantially maintain the function of the SP5 promoter ("bad" sequences).

SEQ ID NOs: 36 to 38 are the −118 to +7 nucleotide sequences of SP5 variants (SP5 good70; SP5 good80; and SP5 good90, respectively) that substantially maintain the function of the SP5 promoter ("good" sequences).

SEQ ID NO: 39 is the consensus Site II sequence shared by functional SP3, SP4, and SP5 variants.

SEQ ID NO: 40 is the consensus telo box sequence shared by functional SP3, SP4, and SP5 variants.

SEQ ID NO: 41 is the consensus TATA box sequence shared by functional SP3, SP4, and SP5 variants.

SEQ ID NOS: 42 to 59 are full length variant sequences described herein.

DETAILED DESCRIPTION OF THE INVENTION

In the context of this disclosure, a number of terms and abbreviations are used. The following definitions are provided.

The articles "a" and "an" are used herein to refer to one or more than one (i.e., to at least one) of the grammatical object of the article. By way of example, "an element" means one or more element.

Throughout the specification the word "comprise," or variations such as "comprises" or "comprising" will be understood to imply the inclusion of a stated element, integer or step, or group of elements, integers or steps, but not the exclusion of any other element, integer or step, or group of elements, integers or steps.

In certain embodiments, the invention relates to transgenic plants and methods for making the same. As used herein, the term "plant" refers to any living organism belonging to the kingdom Plantae (i.e., any genus/species in the Plant Kingdom). In some embodiments, the plant is a tree, herb, bush, grass, vine, fern, moss or green algae. The plant may be monocotyledonous (monocot), or dicotyledonous (dicot). Examples of particular plants that may comprise a polynucleotide of the invention include but are not limited to *Arabidopsis, Brachypodium*, switchgrass, corn, potato, rose, apple tree, sunflower, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, cauliflower, cavalo, collards, kale, kohlrabi, mustard greens, rape greens, and other *brassica* leafy vegetable crops, bulb vegetables (e.g. garlic, leek, onion (dry bulb, green, and Welch), shallot), citrus fruits (e.g. grapefruit, lemon, lime, orange, tangerine, citrus hybrids, pummelo), cucurbit vegetables (e.g. cucumber, citron melon, edible gourds, gherkin, muskmelons (including hybrids and/or cultivars of Cucumis melons), water-melon, cantaloupe, and other cucurbit vegetable crops), fruiting vegetables (including eggplant, ground cherry, pepino, pepper, tomato, tomatillo), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn (maize), rice, wheat, barley, sorghum, millets, oats, ryes, triticales, buckwheats, fonio, quinoa, oil palm), Brassicaceae family plants, and Fabaceae family plants, pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fiber crops (e.g. hemp, cotton), ornamentals, and the like.

*Arabidopsis* is often used as a model plant in biotech research because it offers several advantages to plant researches including but limited to the following: (1) it develops, reproduces and responds to stress and disease much the same way as many crop plants; (2) it produces many seeds and is easy and cheap to grow, since the plant is small and requires little space; (3) it has a shorter life cycle; (4) the low cost of production allows extensive genetic experiments on thousands of plants at once; (5) compared to other plants, it has a small genome and its genetic information is somewhat less complex, allowing for easier genetic analysis; and (6) it is the first plant to have its genome sequenced due to an internationally coordinated program. See, e.g., *Arabidopsis*: Model plant in biotech research (November, 1998) In: The Agbiotech Infosource, Issue 40, Ag-West Biotech Inc.

The invention in certain aspects includes plant parts derived from the transgenic plants described herein. As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

In some embodiments, the transgenic plant is of the Brassicaceae family. As used herein, Brassicaceae family refers to the plant family which is also known as the Cruiferae. The family contains over 330 genera and about 3700 species. Non-limiting examples of plants in this family include cabbage, broccoli, cauliflower, turnip, rapeseed, mustard, radish, horseradish, cress, wasabi, and watercress. Non-limiting examples of Brassicaceae plants include *Brassica oleracea* (broccoli, cabbage, cauliflower, etc.), *Brassica rapa* (turnip, Chinese cabbage, etc.), *Brassica napus* (rapeseed, etc.), *Raphanus sativus* (common radish), *Armoracia rusticana* (horseradish), *Matthiola* (stock), *Arabidopsis thaliana* (model organism), mustard, cress, wasabi, watercress and many others.

In some embodiments, the transgenic plant is a species of *Triticum*. As used herein, *Triticum* species refers to the species in the *Triticum* genus, including but are not limited to, *T. aestivum* (e.g., common wheat, or bread wheat, a.k.a. *Triticum aestivum* L. subsp. *Aestivum*; Club wheat, a.k.a. *Triticum aestivum* subspecies *compactum* (Host) MacKey; *Macha* wheat, a.k.a. *Triticum aestivum* subsp. *macha* (Dek. and Men.) MacKey; Vavilovi wheat, a.k.a. *Triticum aestivum* subsp. vavilovi (Tuman) Sears; Shot wheat, a.k.a. *Triticum aestivum* subsp. *sphacrococcum* (Perc.) MacKey), *T. aethiopicum, T. araraticum, T boeoticum* (e.g., wild Einkorn, a.k.a. *Triticum* boeotictim Boiss), *T. carthlicum, T. compactum, T. dimitrium, T dicoccoides* (e.g., wild emmer, a.k.a. *Triticum dicoccoides* (Koern. ex Ascb. & Graebn.) Aaronsohn.), *T. dicoccum* (e.g., Emmer), *T. durum* (e.g., durum wheat), *T. ispahanicum, T. karamyschevii, T. macha, T militinae, T. monococcum* (e.g., Einkorn, a.k.a. *Triticum monococcum* L.), *T. polonicum, T. spelta, T. sphaerococcum, T. timopheevii* (e.g. timopheevi wheat, a.k.a. *Triticum timopheevii* Zbuk.), *T. turanicum* (e.g., oriental wheat, a.k.a. *Triticum turanicum* jakubz), *T. turgidum* (e.g., poulard wheat, a.k.a. *Triticum turgidum* L.), *T. urartu, T. vavilovii,* and *T. zhukovskyi.*

In some embodiments, the transgenic plant is a species of rice. As used herein, rice refers to the species in the *Oryza* genus, including but not limited to *O. sativa* (e.g., Asian rice), *O. barthii, O. glaberrima* (e.g., Africa rice), *O. longistaminata, O. meridionalis, O. nivara, O. rufipogon* (e.g., brownbeard rice and red rice), *O. punctata, O. latifolia, O. alta, O. grandiglumis, O. eichingeri, O. officinalis, O. rhisomatis, O. minuta, O. australiensis, O. granulate, O. meyeriana,* and *O. brachyantha.*

In some embodiments, the transgenic plant is of the Fabaceae family. As used in herein, Fabaceae family plants refer to the plants in the Fabaceae family, (a.k.a. legume family, pea family, bean family or pulse family), including but are not limited to, *Glycine max* (soybean), *Phaseolus* (beans), *Pisum sativum* (pea), *Cicer arietinum* (chickpeas), *Medicago sativa* (alfalfa), *Arachis hypogaea* (peanut), *Ceratonia siliqua* (carob), and *Glycyrrhiza glabra* (licorice).

The present invention provides polynucleotides comprising genetic regulatory elements. As used herein, the term "genetic regulatory element" refers to a nucleotide sequences that can affect expression of a transcribed sequence in an organism of interest. Genetic regulatory elements of the present invention include, but are not limited to promoters, enhancers, introns, 5'-untranslated regions or part thereof, 3'-untranslated regions or part thereof, terminators, and chromatin control elements. It is recognized that polynucleotides of the present invention can comprise a plurality of regulatory elements such as, for example, a promoter and an enhancer. It is further recognized that some genetic regulatory elements act in concert with other genetic regulatory elements to control the regulation of an operably linked gene of interest. Moreover, it is recognized that some genetic regulatory elements such as, for example, an enhancer, can be separated from the transcribed region a gene of interest by 1, 2, 3, or more kilobases of DNA.

The polynucleotides of the invention may be synthetic nucleotide sequences. A "synthetic nucleotide sequence" is a nucleotide sequence that is not known to occur in nature or that is not naturally occurring. In some embodiments, the polynucleotide shares little or no extended homology to natural sequences. Extended homology in this context generally refers to 100% sequence identity extending beyond about 25 nucleotides of contiguous sequence.

The present invention also provides methods for controlling gene expression. By "controlling gene expression" is intended to mean controlling the expression an RNA transcript, and can further encompass translation of the transcript, or even an activity or function of the encoded protein. Controlling gene expression may include affecting one or more of RNA transcription, processing, turnover, and/or translation. In certain embodiments of the invention, the effect of a genetic regulatory element of the present invention on gene expression can be determined and/or quantified through an operably linked nucleotide sequence encoding the green fluorescent protein (GFP). Fluorescence emitted from the GFP protein when it is exposed to blue light is measured as a marker of expression.

The genetic regulatory elements as disclosed herein can be implemented as regulatory sequences to control gene expression in a "desired manner." The desired manner of gene expression can be temporally, spatially, or any combination thereof in a target organism including, but not limited to, constitutive expression, tissue-preferred expression, and organ-preferred expression. The desired manner of gene expression can also be expression in response to biotic stress (e.g., fungal, bacterial and viral pathogens, insects, herbivores and the like) and/or abiotic stress (e.g., wounding, drought, cold, heat, high nutrient levels, low nutrient levels, metals, light, herbicides and other synthetic chemicals, and the like).

In some embodiments, the present invention provides polynucleotides containing promoters and/or enhancers. "Promoter" refers to a nucleotide sequence that is capable of controlling the expression of an operably linked coding sequence or other sequence encoding an RNA that is not necessarily translated into a protein. Thus, the polynucleotide may comprise proximal promoter elements as well as more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, nucleic acid fragments of some variation may have identical or similar promoter activity.

Promoters that cause a gene to be expressed in most cell types of an organism and at most times are commonly referred to as "constitutive promoters". Expression of a gene in most cell types of an organism and at most times is referred to herein as "constitutive gene expression" or "constitutive expression".

In some embodiments, the regulatory element is an expression-enhancing intron. An "expression-enhancing intron" or "enhancing intron" is an intron that is capable of causing an increase in the expression of a gene to which it is operably linked. While the present invention is not known to depend on a particular biological mechanism, it is believed that the expression-enhancing introns of the present invention enhance expression through intron mediated enhancement (IME). It is recognized that naturally occurring introns that enhance expression through IME are typically found within 1 Kb of the transcription start site of their native genes (see, Rose et al. (2008) *Plant Cell* 20:543-551). Such introns are usually the first intron, whether the first intron is in the 5' UTR or the coding sequence, and need to be in a transcribed region. Introns that enhance expression solely through IME do not enhance gene expression when they are inserted into a non-transcribed region of gene, such as for example, a promoter. That is, they do not function as transcriptional enhancers. Unless stated otherwise or apparent from the context, the expression-enhancing introns of the present invention are capable of enhancing gene expression when they are found in a transcribed region of a gene but not when they occur in a non-transcribed region such as, for example, a promoter.

In some embodiments, the promoter is a plant promoter. A "plant promoter" is a promoter capable of initiating transcription in plant cells whether or not its origin is a plant cell, e.g. it is well known that *Agrobacterium* promoters are functional in plant cells. Thus, plant promoters include promoter DNA obtained from plants, plant viruses and bacteria such as *Agrobacterium* and *Bradyrhizobium* bacteria, and synthetic promoters capable of initiating transcription in plant cells. A plant promoter can be a constitutive promoter, a non-constitutive promoter, an inducible promoter, a repressible promoter, a tissue specific promoter (e.g., a root specific promoter, a stem specific promoter, a leaf specific promoter), a tissue preferred promoter (e.g., a root preferred promoter, a stem preferred promoter, a leaf preferred promoter), a cell type specific or preferred promoter (e.g., a meristem cell specific/preferred promoter), or many other types. In some embodiments, the variant polynucleotides or fragments described herein include additional known cis-acting sequences to drive expression of a transcribed gene in a desired manner.

In some embodiments, the promoter is a constitutive promoter. A "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. For illustration, constitutive promoters include, CaMV 19S promoter, CaMV 35S promoter (U.S. Pat. Nos. 5,352,605; 5,530,196 and 5,858,742), opine promoters, ubiquitin promoter, actin promoter, alcohol dehydrogenase promoter, etc. In some embodiments, the synthetic promoter prepared as described herein, is used to drive expression of a heterologous sequence, while CaMV 35S promoter is used to drive expression of a second sequence.

In some embodiments, the promoter is a non-constitutive promoter. A "non-constitutive promoter" is a promoter which is active under certain conditions, in certain types of cells, and/or during certain development stages. For example, tissue specific, tissue preferred, cell type specific, cell type preferred, inducible promoters, and promoters under developmental control are non-constitutive promoters. Examples of promoters under developmental control include promoters that preferentially initiate transcription in certain tissues, such as stems, leaves, roots, or seeds.

In some embodiments, the promoter is an inducible or a repressible promoter. A "inducible" or "repressible" promoter is a promoter which is under chemical or environmental factor control. Examples of environmental conditions that may affect transcription by inducible promoters include cold, heat, drought, or certain chemicals, or the presence of light.

In some embodiments, the promoter is a tissue specific promoter. A "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature. Non-limiting examples of known tissue specific promoters include, beta-amylase gene or barley hordein gene promoters (for seed gene expression), tomato pz7 and pz130 gene promoters (for ovary gene expression), tobacco RD2 gene promoter (for root gene expression), banana TRX promoter and melon actin promoter (for fruit gene expression), and embryo specific promoters, e.g., a promoter associated with an amino acid permease gene (AAP1), an oleate 12-hydroxylase:desaturase gene from *Lesquerella fendleri* (LFAH12), an 2S2 albumin gene (2S2), a fatty acid elongase gene (FAE1), or a leafy cotyledon gene (LEC2).

In some embodiments, the promoter is a tissue preferred promoter. A "tissue preferred" promoter is a promoter that initiates transcription mostly, but not necessarily entirely or solely in certain tissues.

In some embodiments, the promoter is a cell type specific promoter. A "cell type specific" promoter is a promoter that primarily drives expression in certain cell types in one or more organs, for example, vascular cells in roots, leaves, stalk cells, and stem cells.

In some embodiments, the promoter is a cell type preferred promoter. A "cell type preferred" promoter is a promoter that primarily drives expression mostly, but not necessarily entirely or solely in certain cell types in one or more organs, for example, vascular cells in roots, leaves, stalk cells, and stem cells.

In some embodiments, the promoter is a root specific promoter. A "root specific" promoter is a promoter that initiates transcription only in root tissues.

In some embodiments, the promoter is a root preferred promoter. A "root preferred" promoter is a promoter that initiates transcription mostly, but not necessarily entirely or solely in root tissues.

In some embodiments, the present invention provides method to obtain inbred plants comprising the polynucleotide sequences. As used herein, the term "inbred", "inbred plant" is used in the context of the present invention. This also includes any single gene conversions of that inbred. The phrase "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

In some embodiments, the present invention provides method to obtain hybrid plants comprising the polynucleotide sequences. As used herein, the term "hybrid" refers to any individual cell, tissue or plant resulting from a cross between parents that differ in one or more genes.

In some embodiments, the present invention provides samples comprising the polynucleotide of the invention. The term "sample" includes a sample from a plant, a plant part, a plant cell, or from a transmission vector, or a soil, water or air sample.

In some embodiments, the present invention provides offspring plants comprising the polynucleotides. As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

In some embodiments, the present invention provides methods for crossing the plants comprising the polynucleotide sequences. As used herein, the term "cross", "crossing", "cross pollination" or "cross-breeding" refer to the process by which the pollen of one flower on one plant is applied (artificially or naturally) to the ovule (stigma) of a flower on another plant.

In some embodiments, the present invention provides methods for obtaining plant cultivars comprising the polynucleotide sequences. As used herein, the term "cultivar" refers to a variety, strain or race of plant that has been produced by horticultural or agronomic techniques and is not normally found in wild populations.

In some embodiments, the transgenic plant is a dicot. As used herein, the terms "dicotyledon," "dicot" and "dicotyledonous" all refer to a flowering plant having an embryo containing two seed halves or cotyledons. Dicotyledon plants at least include the Eudicot, Magnoliid, Amborella, Nymphaeales, Austrobaileyales, Chloranthales, and Ceratophyllum groups. Eudicots include these clades: *Ranunculales, sabiales, Proteales, Trochodendrales, Buxales*, and *Core Eudicots* (e.g., *Berberidopsidales, Dilleniales, Gunnerales, Caryophyllales, Santalales, Saxifragales, Vitales, Rosids* and *Asterids*). Non-limiting examples of dicotyledon plants include tobacco, tomato, pea, alfalfa, clover, bean, soybean, peanut, members of the Brassicaceae family (e.g., camelina, Canola, oilseed rape, etc.), amaranth, sunflower, sugarbeet, cotton, oaks, maples, roses, mints, squashes, daisies, nuts; cacti, violets and buttercups.

In some embodiments, the transgenic plant is a monocot. As used herein, the term "monocotyledon," "monocot" and "monocotyledonous" all refer to any of a subclass (Monocotyledoneae) of flowering plants having an embryo containing only one seed leaf and usually having parallel-veined leaves, flower parts in multiples of three, and no secondary growth in stems and roots. Non-limiting examples of monocotyledon plants include lilies, orchids, corn, rice, wheat, barley, sorghum, millets, oats, ryes, triticales, buckwheats, fonio, *quinoa*, grasses, such as tall fescue, goat grass, and Kentucky bluegrass; grains, such as wheat, oats and barley, irises, onions, palms.

For example, to introduce the nucleic acid molecules into corn, the nucleic acid molecules are cloned into a binary vector suitable for corn transformation, such as the vectors described by Sidorov and Duncan, 2008 (*Agrobacterium*-Mediated Maize Transformation: Immature Embryos Versus Callus, Methods in Molecular Biology, 526:47-58), Frame et al., 2002 (*Agrobacterium tumefaciens*-Mediated Transformation of Maize Embryos Using a Standard Binary Vector System, Plant Physiology, May 2002, Vol. 129, pp. 13-22), Ahmadabadi et al., 2007 (A leaf-based regeneration and transformation system for maize (*Zea mays* L.), TransgenicRes. 16, 437-448), U.S. Pat. Nos. 6,420,630, 6,919,494 and 7,682,829, or similar experimental procedures well known to those skilled in the art.

In some embodiments, the present invention provides methods for obtaining plant genotypes comprising the polynucleotide sequences. As used herein, the term "genotype" refers to the genetic makeup of an individual cell, cell culture, tissue, organism (e.g., a plant), or group of organisms.

In some embodiments, the present invention provides homozygotes comprising the polynucleotide sequences. As used herein, the term "homozygote" refers to an individual cell or plant having the same alleles at one or more loci.

In some embodiments, the present invention provides homozygous plants comprising the polynucleotide sequences. As used herein, the term "homozygous" refers to the presence of identical alleles at one or more loci in homologous chromosomal segments.

In some embodiments, the transgenic cell or organism is hemizygous for the gene of interest which is under control of the synthetic regulatory element. As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

In some embodiments, the present invention provides heterozygotes comprising the polynucleotide sequences. As used herein, the terms "heterozygote" and "heterozygous" refer to a diploid or polyploid individual cell or plant having different alleles (forms of a given gene) present at least at one locus. In some embodiments, the cell or organism is heterozygous for the gene of interest which is under control of the synthetic regulatory element.

The polynucleotides of the invention may be positioned so as to control expression of an endogenous gene of interest, or a heterologous gene of interest. As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

In some embodiments, the cell or organism has at least one heterologous trait. As used herein, the term "heterologous trait" refers to a phenotype imparted to a transformed host cell or transgenic organism by an exogenous DNA segment, heterologous polynucleotide or heterologous nucleic acid. Various changes in phenotype are of interest to the present invention, including but not limited to modifying the fatty acid composition in a plant, altering the amino acid content of a plant, altering a plant's pathogen defense mechanism, increasing a plant's yield of an economically important trait (e.g., grain yield, forage yield, etc.) and the like. These results can be achieved by providing expression of heterologous products or increased expression of endogenous products in plants using the methods and compositions of the present invention.

In some embodiments, the present invention provides methods for obtaining plant lines comprising the polynucleotide sequences. As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

In some embodiments, the present invention provides open-pollinated populations comprising the polynucleotide sequences. As used herein, the terms "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

In some embodiments, the present invention provides self-pollination populations comprising the polynucleotide sequences. As used herein, the term "self-crossing", "self pollinated" or "self-pollination" means the pollen of one flower on one plant is applied (artificially or naturally) to the ovule (stigma) of the same or a different flower on the same plant.

In some embodiments, the present invention provides ovules and pollens comprising the polynucleotide sequences. As used herein when discussing plants, the term "ovule" refers to the female gametophyte, whereas the term "pollen" means the male gametophyte.

In some embodiments, the transgenic plants comprising the polynucleotide sequences have one or more preferred phenotypes. As used herein, the term "phenotype" refers to the observable characters of an individual cell, cell culture, organism (e.g., a plant), or group of organisms which results from the interaction between that individual's genetic makeup (i.e., genotype) and the environment.

In some embodiments, the present invention provides plant tissue comprising the polynucleotide sequences. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

In some embodiments, the present invention provides methods for obtaining plants comprising the polynucleotide sequences through transformation. As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

In some embodiments, the present invention provides transformants comprising the polynucleotide sequences. As used herein, the term "transformant" refers to a cell, tissue or organism that has undergone transformation. The original transformant is designated as "T0" or "$T_0$." Selfing the T0 produces a first transformed generation designated as "T1" or "$T_1$."

In some embodiments, the present invention provides transgenes comprising the polynucleotide sequences. As used herein, the term "transgene" refers to a nucleic acid that is inserted into an organism, host cell or vector in a manner that ensures its function.

In some embodiments, the present invention provides transgenic plants comprising the polynucleotide sequences. As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

In some embodiments, the present invention provides transgenic events comprising the polynucleotide sequences. As used herein, the term "transposition event" refers to the movement of a transposon from a donor site to a target site.

In some embodiments, the present invention provides plant varieties comprising the polynucleotide sequences. As used herein, the term "variety" refers to a subdivision of a species, consisting of a group of individuals within the species that are distinct in form or function from other similar arrays of individuals.

The present invention provides novel polynucleotides comprising genetic regulatory elements. Polynucleotides can be made by chemical synthesis of the entire nucleic acid molecule or part or parts thereof, and/or by molecular biology methods such as, for example, restriction endonuclease digestion, DNA amplification by polymerase and ligation.

In some embodiments, the present invention provides organisms comprising the polynucleotide sequences. As used herein, an "organism" refers any life form that has genetic material comprising nucleic acids including, but not limited to, prokaryotes, eukaryotes, and viruses. Organisms of the present invention include, for example, plants, animals, fungi, bacteria, and viruses, and cells and parts thereof.

By "gene of interest" is intended any nucleotide sequence that can be transcribed in a cell. The gene of interest may, but need not, encode a protein.

While the present invention does not depend on a particular method of determining if the polynucleotide is capable of regulating gene expression in the desired manner, typically the function of the polynucleotide of the present invention is determined by transforming an organism or at least one cell thereof with a polynucleotide construct comprising the polynucleotide operably linked to a gene of interest, such as, in some instances, a reporter gene. The polynucleotide construct can further comprise additional genetic regulatory elements, if desired or necessary for expression in the gene of interest in the organism or at least one cell thereof.

Those of skill in the art will appreciate that determining whether the polynucleotide is capable of regulating the expression of an operably linked gene in the desired manner in the target organism or any other organism of interest can depend on any number of factors including, for example, the type of genetic regulatory element (e.g., promoter, a 5'-untranslated region (UTR), a 3'-untranslated region, an intron, a terminator, a chromatin control element), the presence of additional genetic elements in the expression construct, the gene of interest to be expressed, the organism or part or cell thereof in which expression is assayed, the expression assay, the detection method (e.g., GFP visible fluorescence, detection of GFP RNA by qPCR), the environmental conditions during the assay, and the like.

In some embodiments, the transgenes of the present invention comprise 3' non-coding sequences. As used herein, the "3' non-coding sequences" or "3' untranslated regions" refer to DNA sequences located downstream of a coding sequence and include polyadenylation recognition sequences and other sequences encoding regulatory signals capable of affecting mRNA processing or gene expression. The polyadenylation signal is usually characterized by effecting the addition of polyadenylic acid tracts to the 3' end of the mRNA precursor. The use of different 3' non-coding sequences is exemplified by Ingelbrecht, I. L., et al. (1989) *Plant Cell* 1:671-680.

In some embodiments, the transgenes of the present invention comprise at least one reporter gene. As used herein a "reporter" or a "reporter gene" refers to a nucleic acid molecule encoding a detectable marker. The reporter gene can be, for example, luciferase (e.g., firefly luciferase or Renilla luciferase), β-galactosidase, chloramphenicol acetyl transferase (CAT), or a fluorescent protein (e.g., green fluorescent protein (GFP), red fluorescent protein (DsRed), yellow fluorescent protein, blue fluorescent protein, cyan fluorescent protein, or variants thereof, including enhanced variants such as enhanced GFP (eGFP). Reporter genes are detectable by a reporter assay. Reporter assays can measure the level of reporter gene expression or activity by any number of means, including, for example, measuring the level of reporter mRNA, the level of reporter protein, or the amount of reporter protein activity. Reporter assays are known in the art or otherwise disclosed herein.

The present invention provides polynucleotides comprising at least one genetic regulatory element. The polynucleotides of the invention include, but are not limited to, those comprising the nucleotide sequences set forth in SEQ ID NOS: 1 to 10, 15 to 20, and 42 to 50 and fragments and variants thereof that comprise the desired regulatory activity. Such polynucleotides find use in controlling the expression of an operably linked nucleotide sequence in a host cell or organism, particularly a plant, more particularly a crop plant. The invention further provides expression cassettes, plants, plant parts, plant cells, seeds and host cells comprising the polynucleotides of the present invention.

The present invention provides polynucleotides operably linked to at least one gene of interest. As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

Thus, the invention further provides methods for expressing a gene of interest in a plant, plant part, or plant cell. The methods involve operably linking a polynucleotide of the present invention to a gene of interest so as to produce a polynucleotide construct. Such genes of interest will depend on the desired outcome and can comprise nucleotide sequences that encode proteins and/or RNAs of interest. The methods further involve transforming at least one plant cell with the polynucleotide construct. The methods can additionally involve regenerating the transformed plant cell into a transformed plant.

The invention encompasses isolated or substantially purified nucleic acid molecule or polynucleotide compositions. An "isolated" or "purified" nucleic acid molecule or polynucleotide, or biologically active portion thereof, is substantially or essentially free from components that normally accompany or interact with the nucleic acid molecule or polynucleotide as found in its naturally occurring environment. Thus, an isolated or purified nucleic acid molecule or polynucleotide is substantially free of other cellular material or culture medium when produced by recombinant techniques, or substantially free of chemical precursors or other chemicals when chemically synthesized.

In some embodiments, the present invention provides recombinants comprising the polynucleotides. As used herein, the term "recombinant" refers to an artificial combination of two otherwise separated segments of sequence, e.g., by chemical synthesis or by the manipulation of isolated segments of nucleic acids by genetic engineering techniques.

In some embodiments, the present invention provides recombinant constructs comprising the polynucleotides. As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating.

In some embodiments, the present invention provides construct comprising at least one plant selectable or screenable marker. As used herein, the phrase "plant selectable or screenable marker" refers to a genetic marker functional in a plant cell. A selectable marker allows cells containing and expressing that marker to grow under conditions unfavorable to growth of cells not expressing that marker. A screenable marker facilitates identification of cells which express that marker.

The invention encompasses fragments and variants of the disclosed nucleic acid molecules or polynucleotides. By "fragment" is intended a portion of the nucleic acid molecule or polynucleotide, which may be combined with other sequences. Fragments of a polynucleotide comprising genetic regulatory element sequences retain regulatory activity, and/or find use as probes or primers for detecting or constructing the regulatory sequences. Thus, fragments may be (with reference to nucleotide sequences 1 to 10, 15 to 20, and 42 to 50) at least about 15 nucleotides in length, or at least about 20 nucleotides, at least about 30 nucleotides, at least about 40 nucleotides, at least about 50 nucleotides, at least about 60 nucleotides, at least about 70 nucleotides, at least about 80 nucleotides, at least about 90 nucleotides, at least about 100 nucleotides, at least about 150 nucleotides, at least about 200 nucleotides, at least about 250 nucleotides, at least about 300 nucleotides, at least about 350 nucleotides, or more, and each time with reference to a sequence selected from SEQ ID NOS:1 to 10, 15 to 20, and 42 to 50. In some embodiments, the fragment comprises the region of −118 to +7 of a polynucleotide selected from SEQ ID NOS:1 to 5 or 42 to 50 (or variant thereof), and as depicted in FIG. 1.

A fragment of a polynucleotide of the invention may include at least one genetic regulatory element. A biologically active portion of a genetic regulatory element can be prepared by isolating a portion of one of the polynucleotides of the invention that comprises the genetic regulatory element and assessing activity as described herein.

In some embodiments, the present invention provides variants of the polynucleotides. "Variants" is intended to mean substantially similar sequences, which have substantially the same or better activity in regulating gene expression. As used herein, the term "substantially the same" means a level of activity within ±50% in an assay described herein.

For polynucleotides, a variant comprises a polynucleotide having deletions (i.e., truncations) at the 5' and/or 3' end; deletion and/or addition of one or more nucleotides at one or more internal sites in the reference polynucleotide; and/or substitution of one or more nucleotides at one or more sites in the reference polynucleotide. Variant polynucleotides also includes those generated, for example, by using site directed mutagenesis but which still comprise genetic regulatory element activity. Generally, variants of a particular polynucleotide or nucleic acid molecule of the invention will have at least about 60%, 65%, 70%, 75%, 80%, 85%, 90%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or more sequence identity to that particular polynucleotide (e.g., selected from SEQ ID NO: 1 to 10, 15 to 20 and 42 to 50) as determined by conventional sequence alignment programs and parameters or as described elsewhere herein.

In some embodiments, the polynucleotide comprises one or more cis-acting sequences to support basic promoter activity, including a Site II sequence (e.g., SEQ ID NO: 39), a telo box sequence (e.g., SEQ ID NO: 40), and a TATA box sequence (e.g., SEQ ID NO: 41). These elements may be positioned as shown in FIG. 1, that is within the region defined by −200 and +35 with respect to the transcription start site (TSS), or within the region defined by −118 to +7 with respect to the TSS. For example, the polynucleotide may comprise at least one Site II sequence, at least one telo box sequence, and at least one TATA box sequence. In some embodiments, the polynucleotide comprises two or more Site II sequences, and/or two or more telo box sequences, and/or two or more TATA box sequences. These cis-acting sequences may be positioned to support their cis-acting functions in the cell. For example, the two or more Site II sequences may be positioned adjacent to or close to each other, for example, about 0, 1, 5, 10, 15, 20, 25, 30, 50 or more nucleotides apart. At least one site II sequence may be positioned in the region of −25 to −200 relative to the TSS, or in some embodiments, within the region defined by −118 to +7. In some embodiments, the two or more telo box sequences are positioned adjacent or close to each other, for example, about 0, 1, 5, 10, 15, 20, 25, 30, 50 or more nucleotides apart. In some embodiments, at least one telo box sequence may be positioned within the region defined by −118 to +7 or in some embodiments in the region defined by −85 to +35 relative to the TSS. In some embodiments, the two or more TATA box sequences are positioned adjacent or close to each other. The start of the TATA box sequence(s) may be positioned just upstream from the TSS, for example, in a region defined by −4 to −50 from the TSS. The variant sequences and/or fragments maintain other less characterized, or so far uncharacterized, cis-acting sequences that support or enhance promoter function. Likewise, intron sequences of the invention maintain less characterized or uncharacterized cis-acting sequences import for function.

Variant polynucleotides also encompass sequences derived from a mutagenic and recombinogenic procedure such as DNA shuffling. Strategies for such DNA shuffling are known in the art. See, for example, Stemmer (1994) *PNAS* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *PNAS* 94:4504-4509; Crameri et al. (1998) *Nature* 391:288-291; and U.S. Pat. Nos. 5,605,793 and 5,837,458. For PCR amplifications of the polynucleotides disclosed herein, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, New York). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In some embodiments, the present invention provides polynucleotides that hybridize with at least one of SEQ ID NOS: 1 to 10 and 42 to 50 under stringent hybridization conditions. The terms "stringency" or "stringent hybridization conditions" refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M Na$^+$ ion, typically about 0.01 to 1.0 M Na+ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or "conditions of reduced stringency" include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook et al., 2001.

It is recognized that the polynucleotide of the present invention encompass polynucleotide molecules comprising a nucleotide sequence that is sufficiently identical to one of the nucleotide sequences set forth in SEQ ID NOS: 1 to 10, 15 to 20, and 42 to 50. The term "sufficiently identical" is used herein to refer to a first nucleotide sequence that contains a sufficient or minimum number of identical or equivalent nucleotides to a second nucleotide sequence such that the first and second nucleotide sequences have a common functional activity. For example, polynucleotides that have at least about 70%, or at least about 80%, or at least about 90% or at least about 95% identity, or at least about 96%, 97%, 98% or 99% identity are defined herein as sufficiently identical.

To determine the percent identity of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. In some embodiments, a mathematical algorithm utilized for the comparison of two sequences is the algorithm of Karlin and Altschul (1990) *PNAS* 87:2264, modified as in Karlin and Altschul (1993) *PNAS* 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. In some embodiments, a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity values for pairs of sequences provided herein refer to the value obtained using the BLAST 2.0 suite of programs using default parameters (Altschul et al., (1997) *Nucleic Acids Res.* 25:3389-402) using the full-length sequences of the invention. Unless otherwise stated, sequence identity values for multiple sequence alignments provided herein refer to the value obtained using MUSCLE (Version 3.8) using default parameters using the full-length sequences of the invention. See, Edgar (2004) *Nucleic Acids Res.* 32(5):1792-1797; herein incorporated by reference.

The use of the term "polynucleotide" is not intended to limit the present invention to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double stranded forms, hairpins, stem-and-loop structures, and the like.

The polynucleotide of the present invention can be provided in expression cassettes for expression of a gene of interest in the plant or other organism or host cell of interest. It is recognized that the polynucleotide of the present invention and expression cassettes comprising them can be used for the expression in both human and non-human host cells including, but not limited to, host cells from plants, animals, fungi, and algae. In one embodiment of the invention, the host cells are human host cells or a host cell line that is incapable of differentiating into a human being.

The expression cassette will include 5' and 3' regulatory sequences operably linked to the gene of interest to be expressed. "Operably linked" is intended to mean a functional linkage between two or more elements. For example, an operable linkage between one or more genetic regulatory elements and a gene of interest is functional link between the gene of interest and the one or more genetic regulatory elements that allows for expression of the gene of interest. Operably linked elements may be contiguous or non-contiguous. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), polynucleotide to be expressed, and a transcriptional and translational termination region (i.e., termination region) functional in plants or other organism or host cell. The regulatory regions (i.e., promoters, transcriptional regulatory regions, and translational termination regions) and/or the polynucleotide to be expressed may be native/analogous to the host cell or to each other. The promoter may be provided by the polynucleotide of the invention in some embodiments.

Alternatively, any of the regulatory regions and/or the polynucleotide to be expressed may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

In addition to a promoter sequence, the expression cassette can also contain a transcription termination region downstream of the structural gene to provide for efficient termination. The termination region may be obtained from the same gene as the promoter sequence or may be obtained from different genes. The termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-15 9639.

In some embodiments, if the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., *EMBO J* 3:835-846 (1984)) or the nopaline synthase signal (Depicker et al., Mol. and Appl. Genet. 1:561-573 (1982)).

Where appropriate, the genes of interest may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (Virology 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. A selectable marker gene can be positively or negatively selectable. For positive selection, a foreign gene is supplied to a plant cell that allows it to utilize a substrate present in the medium that it otherwise could not use, such as mannose or xylose (for example, refer U.S. Pat. Nos. 5,767,378; 5,994,629). More typically, however, negative selection is used because it is more efficient, utilizing selective agents such as herbicides or antibiotics that either kill or inhibit the growth of nontransformed plant cells and reducing the possibility of chimeras. Non-limiting exemplary marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, sulfonylurea, glyphosate, glufosinate, L-phosphinothricin, triazine, benzonitrile and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng.* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol.* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *PNAS* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *PNAS* 86:5400-5404; Fuerst et al. (1989) *PNAS* 86:2549-2553; Deuschle et al. (1990) *Science* 248:480-483; Gossen (1993) Ph.D. Thesis, University of Heidelberg; Reines et al. (1993) *PNAS* 90:1917-1921; Labow et al. (1990) *Mol. Cell. Biol.* 10:3343-3356; Zambretti et al. (1992) *PNAS* 89:3952-3956; Baim et al. (1991) *PNAS* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *PNAS* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724; Bourouis et al., *EMBO J.* 2(7): 1099-1104 (1983) White et al., *Nucl Acids Res* 18: 1062 (1990), Spencer et al., *Theon Appl Genet* 79: 625-631(1990), U.S. Pat. Nos. 5,034,322; 6,174,724; 6,255, 560; 4,795,855; 5,378,824; and 6,107,549. Such disclosures are herein incorporated by reference.

The above list of selectable marker genes is not meant to be limiting. Any selectable marker gene can be used in the present invention. Numerous plant transformation vectors and methods for transforming plants are available. See, for example, An, G. et al. (1986) *Plant Pysiol.,* 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant Physiol.* 18:481-494; Chee, P. P. and Slightom, J. L. (1992) *Gene* 118:255-260; Christou, et al. (1992) *Trends. Biotechnol.* 10:239-246; D'Halluin, et al. (1992) *Bio/Technol.* 10:309-314; Dhir, et al. (1992) *Plant Physiol.* 99:81-88; Casas et al. (1993) *PNAS* 90:11212-11216; Christou, P. (1993) *In Vitro Cell. Dev. Biol.*-Plant; 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; Guo Chin Sci. Bull. 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) Plant. J. 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

In various embodiments, the methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. Nos. 5,693,512, 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector. *Agrobacterium tumefaciens* is a naturally occurring bacterium that is capable of inserting its DNA (genetic information) into plants, resulting in a type of injury to the plant known as crown gall. A transgenic plant formed using *Agrobacterium* transformation methods typically contains a single gene on one chromosome, although multiple copies are possible. Such transgenic plants can be referred to as being hemizygous for the added gene.

Other methods utilized for the delivery foreign DNA or other foreign nucleic acids involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701; *Methods for Plant Molecular Biology* (Weissbach and Weissbach, eds.) Academic Press, Inc. (1988); *Methods in Plant Molecular Biology* (Schuler and Zielinski, eds.) Academic Press, Inc. (1989); M. E. Fromm et al., Nature, 319, 791 (1986); H. Jones et al., Plant Mol. Biol., 13, 501 (1989) and H. Yang et al., Plant Cell Reports, 7, 421 (1988); UMizuno et al., 2004; Petolino et al., 2000; U.S. Pat. No. 5,302,523; and US Application Publication No. 20040197909; Kaepler et al., 1992; Raloff, 1990; Wang, 1995; U.S. Pat. Nos. 5,204,253; 5,015,580; 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and Raineri et al., Bio/Tech. 8:33-38 (1990), each of which is incorporated herein by reference in its entirety). The method of transformation depends upon the plant cell to be transformed, stability of vectors used, expression level of gene products and other parameters. Specific methods for transforming certain plant species (e.g., maize, rice, wheat, barley, soybean) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated by reference in its entirety.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *PNAS* 83:5602-5606, *Agrobacterium*-mediated transformation as described by Townsend et al., U.S. Pat. No. 5,563,055, Zhao et al., U.S. Pat. No. 5,981,840, Yukou et al., WO 94/000977, and Hideaki et al., WO 95/06722, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *PNAS* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bowen et al., U.S. Pat. No. 5,736,369 (cereals); Bytebier et al. (1987) *PNAS* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

In some embodiments, the polynucleotides of the invention may be introduced into plants using a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

In some embodiments, genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

In this manner, the present invention provides transformed seed (also referred to as "transgenic seed") having a polynucleotide construct of the invention, for example, an expression cassette of the invention, stably incorporated into their genome.

In specific embodiments, the nucleic acid molecules and polynucleotide constructs of the present invention can be provided to a plant using a variety of transient transformation methods. Such transient transformation methods include, but are not limited to, the introduction of the sequence or variants and fragments thereof directly into the plant or the introduction of a transcript into the plant. Such methods include, for example, microinjection, electroporation, or particle bombardment. See, for example, Crossway et al. (1986) *Mol Gen. Genet.* 202:179-185; Nomura et al. (1986) *Plant Sci.* 44:53-58; Hepler et al. (1994) PNAS 91: 2176-2180 and Hush et al. (1994) *The Journal of Cell Science* 107:775-784, Sheen, J. 2002. A transient expression assay using maize mesophyll protoplasts. Sheen, J. 2001. Signal transduction in maize and *Arabidopsis* mesophyll protoplasts. Plant Physiol. 2001 December; 127:1466-1475, Anderson et al., U.S. Pat. No. 7,645,919 B2, all of which are herein incorporated by reference. Alternatively, the polynucleotide can be transiently transformed into the plant using techniques known in the art.

The nucleic acid molecules and polynucleotide constructs of the present invention can be used for transformation of any plant species, including, but not limited to, monocots and dicots. Examples of plant species of interest include, but are not limited to, *Arabidopsis thaliana*, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), petunia (*Petunia* spp., e.g., *Petunia* x *hybrida* or *Petunia hybrida*), corn or maize (*Zea mays*), *Brassica* ssp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), green millet (*Setaria viridis*), finger millet (*Eleusine coracana*)), sunflower (*Helianthus annuus*), safflower (*Carthamus tinctorius*), wheat (*Triticum aestivum*), soybean (*Glycine max*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (Macadamia *integrifolia*), almond (*Prunus amygdalus*), sugar beets (*Beta vulgaris*), sugarcane (*Saccharum* spp.), switchgrass (*Panicum virgatum*), algae (e.g., *Chlamydomonas reinhardtii, Botryococcus braunii, Chlorella* spp., *Dunaliella tertiolecta, Gracilaria* spp.), oats, barley, vegetables, ornamentals, and conifers. The nucleic acid molecules and polynucleotide constructs of the present invention can also be used for transformation of any algae species.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, yield, abiotic stress tolerance, and commercial products. Genes of interest include, generally, those involved in oil, starch, carbohydrate, or nutrient metabolism. In addition, genes of interest include genes encoding enzymes and other proteins from plants and other sources including prokaryotes and other eukaryotes.

In some embodiments, the expression unit may be further optimized by employing supplemental elements such as transcription terminators and/or enhancer elements. Enhancer sequences derived from the CaMV can also be utilized (U.S. Pat. Nos. 5,164,316; 5,196,525; 5,322,938; 5,530,196; 5,352,605; 5,359,142; and 5,858,742 for example).

The present invention provides methods of producing a transgenic plant comprising one or more synthetic promoters and/or synthetic introns as described above. In one embodiment, the methods comprise incorporating the promoters and/or introns of the present invention into a plant. One skilled in the art would be able to select suitable methods of incorporation. For example, the polynucleotides can be incorporated into a plant by transforming the plant with an expression vector. The promoters and/or introns can also be incorporated into a plant by breeding methods. For example, a transgenic plant comprising synthetic promoters and/or synthetic introns of the present invention can be crossed to a second plant to produce a progeny wherein new transgenic plants comprising the synthetic promoters and/or synthetic introns can be isolated. Methods of breeding are discussed separately below. Plants and their progeny, including plant cultures, may be prepared by conventional methods, which are summarized below.

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subcultured) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microflora will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora do not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, and conversely any positive traits would remain within the line also. Plant tissue culture is used widely in plant science; it also has a number of commercial applications. Applications include:

1. Micropropagation is widely used in forestry and in floriculture. Micropropagation can also be used to conserve rare or endangered plant species.
2. A plant breeder may use tissue culture to screen cells rather than plants for advantageous characters, e.g. pathogen resistance/tolerance.
3. Large-scale growth of plant cells in liquid culture inside bioreactors as a source of secondary products, like recombinant proteins used as biopharmaceuticals.
4. To cross distantly related species by protoplast fusion and regeneration of the novel hybrid.
5. To cross-pollinate distantly related species and then tissue culture the resulting embryo which would otherwise normally die (Embryo Rescue).
6. For production of doubled monoploid (dihaploid) plants from haploid cultures to achieve homozygous lines more rapidly in breeding programs, usually by treatment with colchicine which causes doubling of the chromosome number.
7. As a tissue for transformation, followed by either short-term testing of genetic constructs or regeneration of transgenic plants.
8. Certain techniques such as meristem tip culture can be used to produce clean plant material from infected stock, such as potatoes and many species of soft fruit.
9. Micropropagation using meristem and shoot culture to produce large numbers of identical individuals.

Non-limiting exemplary tissue culture methods for wheat, rice, maize have been described by Trione et al., Dodig, et al., O'Hara et al., Zaidi et al., Wang et al., Ting et al., Hawes et al., and Sheridan, each of which is incorporated by reference in its entirety.

The present invention also provides a cutting, a rootstock, a scion, or an explant from the plants of the present invention.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. Detailed non-limiting grafting methods for wheat and maize are described by Lacadena, 1968, and Katsumi et al., each of which is incorporated by reference in its entirety.

Any transgenic plant comprising a polynucleotide (e.g., one or more promoters and/or introns) of the present invention can be used as a donor to produce more transgenic plants through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

In some embodiments, said methods comprise (i) crossing any one of the plants of the present invention comprising one or more promoters and/or introns as a donor to a recipient plant line to create a F1 population; (ii) evaluating the transgene expression in the offsprings derived from said F1 population; and (iii) selecting offsprings that have functional transgene expression under the control of the synthetic promoters and/or synthetic introns.

In some embodiments, complete chromosomes of the donor plant are transferred. For example, the transgenic plant with the promoters and/or introns can serve as a male or female parent in a cross pollination to produce offspring plants, wherein by receiving the transgene from the donor plant, the offspring plants obtained the synthetic promoters and/or synthetic introns. In some embodiments, only the genomic fragment containing the transgene (e.g., having the synthetic promoters and/or synthetic introns) is incorporated into the recipient plant.

In some embodiments, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, production of specific biofuels, increased food production, improved food quality, etc. Additional examples of agronomically important traits includes pest resistance, vigor, development time (time to harvest), enhanced nutrient content, novel growth patterns, flavors or colors, salt, heat, drought and cold tolerance, and the like. Agronomically important traits do not include selectable marker genes (e.g., genes encoding herbicide or antibiotic resistance used only to facilitate detection or selection of transformed cells), hormone biosynthesis genes leading to the production of a plant hormone (e.g., auxins, gibberellins, cytokinins, abscisic acid and ethylene that are used only for selection), or reporter genes (e.g. luciferase, β-glucuronidase, chloramphenicol acetyl transferase (CAT, etc.). For example, the recipient plant can be a plant with increased seed weight and/or seed size. The recipient plant can also be a plant with preferred carbohydrate composition, e.g., composition preferred for nutritional or industrial applications, especially those plants in which the preferred composition is present in seeds.

The invention further provides methods for developing plants in a plant breeding program using plant breeding techniques including recurrent selection, backcrossing, pedigree breeding, molecular marker (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), and Simple Sequence Repeats (SSRs) which are also referred to as Microsatellites, etc.) enhanced selection, genetic marker enhanced selection and transformation. Seeds, plants, and parts thereof produced by such breeding methods are also part of the invention.

In addition, any and all products made using the seeds, plants and parts thereof obtained from the transgenic plants or parts of such transgenic plants, or from any progeny plants or parts of such progeny plants produced using the transgenic plants as a direct or indirect parent to produce such progeny are also part of the invention. Examples of such products include but are not limited to lumber, flowers, animal feed, fruit, meal, flour, starch, syrup, sweetener, oil, biofuels, such as ethanol, and renewable chemicals, such as isobutanol. The origin of the transgene used in such plant products can be determined by tracking the source of the corn used to make the products and/or by using protein (isozyme, ELISA, etc.) and/or DNA (RFLP, PCR, SSR, SNP, EST, etc.) testing.

Classic breeding methods can be included in the present invention to introduce one or more synthetic regulatory elements of the present invention into other plant varieties, or other close-related species that are compatible to be crossed with the transgenic plants of the present invention.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, Plant Breeding Methodology, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics. A synthetic variety is produced by crossing a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic varies widely. In practice, numbers of parental lines range from 10 to several hundred, with 100-200 being the average. Broad based synthetics formed from 100 or more clones would be expected to be more stable during seed multiplication than narrow based synthetics.

Pedigreed varieties. A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that are used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

This invention is further illustrated by the following examples which should not be construed as limiting. The contents of all references, patents and published patent applications cited throughout this application, as well as Sequence Listings, are incorporated herein by reference.

Example 1

Preparation and Quantitative Root Expression Testing of Identified Synthetic Promoters in Stably Transformed *Arabidopsis*

To assess promoter activity of certain putative promoters in stable transformed plants, polynucleotides comprising each of the nucleotide sequences set forth in SEQ ID NOS: 1-5 (synthetic promoters SP1-SP5) were synthesized with flanking AscI and RsrII sites and cloned into a pUC57 vector by a contract DNA synthesis vendor (GenScript USA Inc., Piscataway, N.J. 08854). The AscI/RsrII promoter containing fragment from the resulting plasmid was then excised and cloned into AscI and RsrII sites of binary vector pGR716 using standard molecular biology procedures. pGR716 is a modified version of the binary vector pCambia0380. To construct pGR716, the region between the left and right T-DNA borders of pCambia0380 was replaced with an expression cassette consisting of a constitutively expressed NptII kanamycin resistance gene followed by a promoterless mGFP5-ER gene with AscI and RsrII sites 5' to the ATG start codon. The final constructs were transferred to *Agrobacterium* for transformation into *Arabidopsis* 'Columbia' ecotype plants by the floral dip method (Clough and Bent (1998) *Plant J.* 16:735) to generate polynucleotide::GFP fusions in transgenic plants. Transformed plants (T1) are selected by growth in the presence of kanamycin. Following selection, transformants are transferred to MS plates and allowed to recover.

In general, at least 12 kanamycin resistant T1s were selected per construct and allowed to set seed (T2 generation). Copy number analysis was performed on excised leaves of the T1s by qPCR. Typically, representative T2 seedlings from the 6 lowest copy number lines of each construct were visually screened for GFP fluorescence with a fluorescent microscope.

Constructs that showed GFP fluorescence in 2 or more independent transgenic lines were analyzed further. To assess expression in root tissues, T2 seedlings from two lines with observable GFP fluorescence were grown in MS media in the RootArray, a device designed for confocal imaging of living plant roots under controlled conditions, and described in U.S. Patent Publication No. 2008/0141585 which is hereby incorporated by reference in its entirety. After 5 days growth, the roots were stained with FM4-64 and imaged for GFP fluorescence in the meristematic zone, elongation zone and maturation zone with approximately 50 seedlings analyzed per line.

In order to yield quantitative results from image pixel intensities, imaging conditions and measurements were strictly controlled. The imaging normalization and calibration methods were based on two key measurements. First, on any day measurements are taken, a dilution series of an external reference fluorophore was quantitatively imaged. Second, the post objective laser intensity was directly measured before and after each RootArray experiment in order to account for variations in laser light intensity that may have occurred.

The dilution series that was imaged each day was prepared from a reference standard. The reference standard was prepared from a concentrated stock of Alexa Fluor 488 in MES buffer (pH 6.0), with its concentration determined by spectrophotometry. Aliquots of the reference standard were stored at −20° C. as a master stock. For calibration use, a dilution series of the stock was prepared in a sealed, modified 96 well plate. The dilution series was stored at 4° C. in the dark and used for up to one month before being replaced. The Alexa Fluor standard was verified to be stable under these conditions. The dilution series was imaged at the beginning of each day to characterize the performance of the detector and optics of the microscope as described below.

Tests have shown that laser light intensity can vary up to 10% at a given setting over the course of a RootArray experiment. To correct for this, laser power is measured before and after each RootArray experiment. The laser intensity is actively adjusted to 355±15 μW at 488 nm at the beginning of each experiment. The change in intensity measured at the end of a RootArray experiment was assumed to be due to a linear transition. Therefore, the estimated light intensity for a specific RootArray image was interpolated from that image's timestamp.

To correct for variations in laser intensity and detector response a model was developed to describe how Alexa Fluor 488 fluorescence varied with laser intensity under the imaging conditions described herein. The laser correction model for Alexa Fluor 488 is based on the relative change of the dilution series slope versus the relative change of laser light intensity. Experiments have demonstrated that this relationship is independent of scan settings. This model was then adapted to GFP in root tissue with the addition of a GFP specific variable. This model is used to calculate a GFP expression index (GEI) as described in Equation 1 below.
Equation 1: GFP expression index (GEI)

$$GEI = \frac{\mu(roi(Img)) - bkg(Img))}{\alpha_{AF}^{DS} \beta_{Sat}} \gamma_{AF}^{DS} \gamma_{AF}^{Img} \delta_{GFP}^{Img}$$

roi(Img): The pixel population for the quantification channel (green channel) over a selected region of interest. In this case each ROI is a tissue type.

bkg(Img): The background pixel value for every experimental image is characterized with a novel statistics based approach, described below.

$\alpha_{AF}^{DS}$: Normalized slope of the dilution series standard.

$\gamma_{AF}^{DS}$: Laser correction factor for Alexa Fluor 488 fluorophore to normalize the dilution series to the reference laser power (355 μW at 488 nm).

$\gamma_{AF}^{DS}$: Laser correction factor for Alexa Fluor 488 fluorophore at the laser power the GFP image was taken.

$\delta_{GFP}^{Img}$: Relative laser correction factor for GFP fluorophore in the experimental image.

$\beta_{Sat}$: Normalization constant to prevent pixel oversaturation of the detector when the image was acquired.

The green channel image signal passes through this function to produce the GEI, a metric of fluorescent intensity that allows for comparison across RootArrays over time. The background of each experimental image was calculated as described below and subsequently subtracted from the pixel population of the region of interest. The negative values were zeroed to create an image with minimal background noise. The mean of corrected pixel intensities was divided by the slope of the dilution series to convert the pixel output to a metric of light intensity relative to the dilution series standard. The first gamma value $\gamma_{AF}^{DS}$ is a laser correction factor that adjusts the slope of the dilution series to what it would be if the dilution series was imaged at exactly 355 μW. The next gamma $\gamma_{AF}^{Img}$ and the delta values $\delta_{GFP}^{Img}$ correct the GFP signal to what it would be if the root was imaged at exactly 355 μW. It is noted that all correction factors typically varied by less than 5% between experiments.

Regions of interest that have a strong signal near the point of pixel oversaturation of the detector did not exhibit a linear relationship with GFP expression. Therefore a normalization constant $\beta_{Sat}$ was included to limit the scope of the dynamic bit range of the detector and the GEI is capped at 1 to preserve its linear correlation with GFP expression for all reported values <1. To calculate the background of an image bkg(Img), the image was first split into a grid of squares and the pixel population of each square is examined. A small number of squares was initially selected based on having the lowest percentile rankings in terms of standard deviation, 95th percentile pixel value, mean, median, and gradient magnitude. The pixel populations in the initial "seed" squares, which are assumed to be background, were then compared against the pixel populations of all other squares in a one tailed unpaired t test in order to categorize each square as "background" or "non-background". The median pixel intensity of all squares determined to be "background" was then used as the bkg(Img) value in Equation 1. Tests have shown that this algorithm robustly selected background pixel populations even if there were several roots in the field of view.

The correspondence of regions of interest to different cell-types was determined from the images using a predefined root template. The template was calculated using a series of images manually segmented to find the root's "tissue percentage profile" (TPP), in which each region of interest in the template is a percentage of the root thickness at the specified location relative to the quiescent center (QC). Using different TPPs for each root zone, the images were segmented into different regions of interest (ROI) corresponding to different root cell-types. Specifically, the regions determined in all three developmental zones were the epidermis, the cortex, the endodermis, and the stele. In addition to these four regions, the root cap and the quiescent center were also determined in the meristematic zone.

To determine if a particular transgenic line exhibited significant GFP expression in an ROI, the GEI measurements for each of the 14 tissue-zone ROIs were compared to the corresponding values determined from 48 non-transgenic *Arabidopsis* Columbia ecotype seedlings grown under identical conditions. Significance was determined using a one-tailed Welch's t-test with a cutoff of p<0.01.

The average GEI for each of the 14 tissue-zone ROIs for two representative lines of five nucleic acid molecules that passed prescreening is shown in Table 1. All values for the nucleic acid molecules in Table 1 represent significant expression (p<0.01). The GEIS measured from seedlings containing a CaMV 35S promoter-GFP transgene are shown for comparison. The 35S promoter is widely used in plant biotechnology and considered a standard for strong promoters. These data demonstrate that the promoters of the present drive significant expression of an operably linked gene of interest.

TABLE 1

GFP Expression Index (GEI) in Root Tissue for Five Synthetic Nucleic Acid Molecules with Promoter Activity

| Promoter | Meristem | | | | | | Elongation | | | | Maturation | | | |
| --- | --- | --- | --- | --- | --- | --- | --- | --- | --- | --- | --- | --- | --- | --- |
| | epi* | cor | end | ste | qc | cap | epi | cor | end | ste | epi | cor | end | ste |
| SP1-1 | 0.077 | 0.078 | 0.07 | 0.068 | 0.019 | 0.027 | 0.022 | 0.017 | 0.013 | 0.017 | 0.01 | 0.006 | 0.008 | 0.014 |
| SP1-2 | 0.242 | 0.253 | 0.208 | 0.153 | 0.065 | 0.094 | 0.048 | 0.035 | 0.027 | 0.033 | 0.016 | 0.011 | 0.016 | 0.037 |
| SP2-1 | 0.32 | 0.311 | 0.287 | 0.216 | 0.167 | 0.188 | 0.096 | 0.084 | 0.067 | 0.058 | 0.022 | 0.018 | 0.022 | 0.037 |
| SP2-2 | 0.046 | 0.038 | 0.033 | 0.019 | 0.324 | 0.257 | 0.047 | 0.01 | 0.006 | 0.005 | 0.072 | 0.043 | 0.04 | 0.073 |
| SP3-1 | 0.222 | 0.306 | 0.274 | 0.171 | 0.161 | 0.129 | 0.072 | 0.059 | 0.051 | 0.039 | 0.014 | 0.014 | 0.018 | 0.033 |
| SP3-2 | 0.336 | 0.358 | 0.341 | 0.271 | 0.318 | 0.274 | 0.088 | 0.066 | 0.055 | 0.047 | 0.021 | 0.019 | 0.024 | 0.058 |
| SP4-1 | 0.162 | 0.169 | 0.153 | 0.106 | 0.057 | 0.065 | 0.052 | 0.031 | 0.021 | 0.021 | 0.019 | 0.011 | 0.012 | 0.017 |
| SP4-2 | 0.529 | 0.556 | 0.495 | 0.381 | 0.124 | 0.212 | 0.186 | 0.13 | 0.1 | 0.093 | 0.041 | 0.031 | 0.041 | 0.054 |
| SP5-1 | 0.241 | 0.318 | 0.261 | 0.122 | 0.012 | 0.016 | 0.116 | 0.114 | 0.084 | 0.059 | 0.021 | 0.021 | 0.024 | 0.024 |
| SP5-2 | 0.366 | 0.42 | 0.389 | 0.257 | 0.048 | 0.065 | 0.136 | 0.119 | 0.1 | 0.084 | 0.025 | 0.026 | 0.035 | 0.059 |
| CaMV 35S | 0.396 | 0.282 | 0.236 | 0.229 | 0.957 | 1 | 0.24 | 0.083 | 0.084 | 0.195 | 0.235 | 0.216 | 0.31 | 0.545 |

*In Table 1, "epi" is epidermis, "cor" is cortex, "end" is endodermis, "ste" is stele, "qc" is quiescent center, and "cap" is root cap.

Expression of GFP in aerial tissue of the stably transformed *Arabidopsis* described above was assessed by qRT-PCR. T2 seeds from each line were grown on MS agar plates. After 4 days the segregating seedlings were screened for GFP fluorescence to identify those that carried the transgene. The GFP positive seedlings were grown an additional 7 days after which the aerial portions of approximately 10 GFP positive plants were collected in triplicate for RNA extraction and cDNA synthesis. Tissue was homogenized in liquid nitrogen via bead milling and total RNA was extracted using the Allprep DNA/RNA kit (Qiagen). cDNA was generated from total RNA using the Superscript VILO cDNA synthesis kit (Invitrogen) per the manufacturer's instructions. Multiplex qPCR TaqMan assays were conducted using either the CFX96 Real-Time PCR Detection System or the iCycler iQ Real-Time PCR Detection System (both instruments are from Bio-Rad Laboratories) with primers and probes specific for GFP and the strong, constitutively expressed, internal control gene UBC9 (AT4G27960). Three technical qRT-PCR replicates were performed on each biological replicate, and data was processed using CFX Manager software (Bio-Rad).

To determine relative GFP expression level, PCR reaction efficiency was calculated using LinRegPCR software (Ruijter) and verified using a standard curve based method. Ct and baseline threshold values were obtained from the CFX Manager software. Data analysis was performed using the statistics package R, available at the R Project for Statistical Computing. After correcting the Ct values for reaction efficiency, the relative GFP expression was calculated by subtracting the Ct of the UBC control from that of GFP, followed by averaging across all replicates. To assess statistical significance of the data, the relative GFP expression of each line was compared to that determined from non-transgenic *Arabidopsis* ecotype Columbia seedlings using a one-tailed Welch's t-test. All statistical analysis was performed on the corrected Ct values, but these values were exponentiated to a linear expression scale for presentation. To normalize the linear expression scale, the data was expressed relative to a 35S-promoter control that was included in all experiments. The 35S-promoter control value was set to 100 on this scale.

Aerial expression data for the two representative lines of the five nucleic acid molecules is shown in Table 2. All expression measurements were statistically significant (p<0.01). These data demonstrate that the synthetic promoters drive significant expression of an operably linked gene of interest.

TABLE 2 qRT-PCR Expression Data in Aerial Tissue for Five Synthetic Nucleic Acid Molecules with Promoter Activity

| Promoter | Relative Expression |
| --- | --- |
| SP1-1 | 0.2 |
| SP1-2 | 0.6 |
| SP2-1 | 2.9 |
| SP2-2 | 1.7 |
| SP3-1 | 3.8 |
| SP3-2 | 6.7 |
| SP4-1 | 0.9 |
| SP4-2 | 1.4 |
| SP5-1 | 0.1 |
| SP5-2 | 0.8 |

Example 2

Preparation and Testing of Expression-Enhancing Activity of Identified Synthetic Introns in Stably Transformed *Arabidopsis*

The expression enhancement activity of synthetic introns, prepared in accordance with this disclosure, was assessed in stable transformed plants. Nucleic acid molecules comprising each of the nucleotide sequences set forth SEQ ID NOS: 6-10 were linked to the 3'-end of promoter-5'-UTR sequences from each of the *Arabidopsis* AT4G37830 and AT1G51650 genes. The promoter-UTR sequences that were used to assess expression enhancement activity comprise either 857 bp (AT4G37830; SEQ ID NO: 11) or 815 bp (AT1G5160; SEQ ID NO: 12) of sequence directly upstream of the ATG start codons of the respective genes. These promoter-UTR sequences were previously shown to drive GFP expression in all root tissues when operably linked to enhancing introns, but did not drive detectable GFP expression in the absence of enhancing introns (see, PCT/US2011/043197, which is hereby incorporated by reference in its entirety).

Each promoter-UTR-intron sequence was synthesized as a single polynucleotide with flanking AscI and RsrII sites and cloned into a pUC57 vector by a contract DNA synthesis vendor (GenScript USA Inc., Piscataway, N.J. 08854). The AscI/Rsth promoter-UTR-intron containing fragment from the resulting plasmid was then excised and cloned into AscI and RsrII sites of binary vector pGR716 using standard molecular biology procedures. pGR716 is a modified version of the binary vector pCambia0380. To construct pGR716, the region between the left and right T-DNA borders of pCambia0380 was replaced with an expression cassette consisting of a constitutively expressed NptII kanamycin resistance gene followed by a promoterless mGFP5-ER gene with AscI and RsrII site 5' to the ATG start codon. The final constructs were transferred to *Agrobacterium* for transformation into *Arabidopsis* Columbia ecotype plants by the floral dip method (Clough and Bent (1998) *Plant J.* 16:735) to generate polynucleotide::GFP fusions in transgenic plants. Transformed plants (T1) were selected by growth in the presence of kanamycin. Following selection, transformants were transferred to MS plates and allowed to recover.

In general, about 20-40 kanamycin resistant T1 s were visually screened under a fluorescent microscope for GFP fluorescence in root tissues. Average expression of each promoter and intron combination was scored by eye using the following scale: "−" for no detectable expression; 1 to 5 "+"s for minimal to very strong expression, respectively; and "n/a" if not tested (see Table 3). Note that in the absence of an intron, neither promoter is capable of driving detectable GFP expression.

TABLE 3

Expression
Enhancement of Two Promoters
by Operably Linking Five Synthetic
Introns Combinations

| Intron | AT4G37830 | AT1G51650 |
| --- | --- | --- |
| SI 1 | +++ | ++ |
| SI 2 | ++++ | +++ |
| SI 3 | +++ | nd |
| SI 4 | +++ | +++ |
| SI 5 | +++ | ++ |
| None | | |

*nd = not determined

The data shown in Table 3 demonstrate that expression-enhancing introns of the present invention can be operably linked to promoters to enhance their expression activity.

Example 3a

Preparation and Quantitative Root Expression Testing of Functional Variants of Synthetic Promoters in Stably Transformed *Arabidopsis*

3 variants were made of each of SP3, SP4, and SP5 at each of approximately 90%, 80%, and 70% identity (the % identity of the variants is shown in Table 4a). The variants designated "good" maintained cis elements predicted to be important for promoter activity while the variants designated "bad" had mutations in conserved nucleotides within these elements (Table 4a and FIG. 1). The prediction is that the "good" variants will fully or substantially retain promoter activity, or even have more activity while the "bad" variants will not.

Specifically, the "good" and "bad" sequences can be distinguished by the presence or absence of three nucleotide motifs in approximately the −118 to +7 region, relative to the expected transcription start site (TSS), that are predicted to be important for promoter activity. The "good" sequences preserve all three motifs, while the "bad" sequences disrupt one or more of them. The first motif is the Site II element, (A/G)GCCCA(A/T)(A/T) (SEQ ID NO: 39), which may occur on either strand (i.e. the reverse complement of the motif may appear in the listed sequences). The notation "(A/G)" signifies that either an "A" or a "G" is acceptable in that position, and so on. The second motif is the telo box element, AAACCCTA(G/A) (SEQ ID NO: 40), which may also occur on either strand. The third motif is the TATA box, TATA(T/A)A(T/A)A (SEQ ID NO: 41). The TATA box must occur on the sense strand, but the first 6 positions are conserved more than the last two. The presence of these motifs within the variant sequences is shown in FIG. 1.

SP3 and the "good" variants thereof contain (from 5' to 3') three superimposed Site II elements, a single Site II element, a telo box, and a TATA box. Both the sequence and position of the elements is conserved. The "bad" variants of SP3 include at least 3 mutations within these elements at positions that are conserved in the "good" variants, and typically include multiple mutations in each element.

SP4 and the "good" variants thereof contain (from 5' to 3') two individual Site II elements, a telo box, and a TATA box. Both the sequence and exact position of the elements is conserved. The "bad" variants of SP4 include at least 3 mutations within these elements at positions that are conserved in the "good" variants, and typically include multiple mutations in each element.

SP5 and the "good" variants thereof contain (from 5' to 3') a single Site II element, a telo box, and two TATA boxes with the last 1-2 bases not conserved. Both the sequence and position of the elements is conserved. The "bad" variants of SP5 include at least 3 mutations within these elements at positions that are absolutely conserved in the active variants, and typically include multiple mutations in each element.

To assess the activity of functional variants of the synthetic promoters indicated in Table 4a, the variant sequences were synthesized, cloned in front of the mGFP5-ER gene in vector pGR716, and transformed into *Arabidopsis* as described in Example 1. For each variant, 12 to 44 T1s were selected as described in Example 1 and visually assessed for GFP expression by fluorescence microscopy. Average expression of each variant was scored by eye using the following scale: "−" for no detectable expression; 1 to 5 "+"s for minimal to very strong expression, respectively (Table 4a). Comparable visual expression scores for T2 seedlings from 3 to 6 independent lines of the parent SPs are also shown in Table 4a for comparison. Note that the visual expression scores for the parent sequences can be compared to the quantitative measurements reported in Table 1.

The data in Table 4a demonstrates that sequence variants of synthetic promoters described herein retain functional promoter activity in stably transformed plants when they retain these three conserved nucleotide motifs which are critical, but not alone sufficient for function. The polynucleotides maintain other sequences critical for, or optimal for, function.

TABLE 4a

Expression activity of sequence variants of synthetic promoters

| Variant | % identity | retain cis-elements | Expression | SEQ ID NO. |
|---|---|---|---|---|
| SP3 |  | yes | ++ | 3 |
| SP4 |  | yes | ++ | 4 |
| SP5 |  | yes | ++ | 5 |
| SP3good90 | 90.5% | yes | ++ | 42 |
| SP4good90 | 90.1% | yes | ++ | 43 |
| SP5good90 | 91.1% | yes | +++ | 44 |
| SP3good80 | 80.4% | yes | + | 45 |
| SP4good80 | 80.2% | yes | ++ | 46 |
| SP5good80 | 81.2% | yes | ++ | 47 |
| SP3good70 | 69.7% | yes | ++ | 48 |
| SP4good70 | 70.3% | yes | ++ | 49 |
| SP5good70 | 71.3% | yes | ++ | 50 |
| SP3bad90 | 89.7% | no | — | 51 |
| SP4bad90 | 89.9% | no | — | 52 |
| SP5bad90 | 90.5% | no | — | 53 |
| SP3bad80 | 80.6% | no | — | 54 |
| SP4bad80 | 80.8% | no | — | 55 |
| SP5bad80 | 79.8% | no | — | 56 |
| SP3bad70 | 69.7% | no | — | 57 |
| SP4bad70 | 70.3% | no | — | 58 |
| SP5bad70 | 70.3% | no | — | 59 |

Example 3b

Preparation and Quantitative Root Expression Testing Synthetic Expression-Enhancing Introns in Stably Transformed *Arabidopsis*

To select and assess the activity of functional variants of the synthetic introns, one or more variants of the synthetic introns are subjected to the procedures as described in Example 1 or Example 2.

Non-limiting examples of synthetic intron variants are listed in Table 4b. In some embodiments, these variants to be tested are identified or made by replacing one or more motif sequences in the synthetic intron with one or more natural, conserved motifs in a plant intron, or by hybridization in a synthetic sequence library, using any one of SEQ ID NOs: 6-10 as bait.

TABLE 4b

Synthetic Intron Variants

Synthetic Intron Sequence

Sequences at least 70%, 75%, 80%, 85%, 90%, or 95% identical to SEQ ID NO: 6
Sequences at least 70%, 75%, 80%, 85%, 90%, or 95% identical to SEQ ID NO: 7
Sequences at least 70%, 75%, 80%, 85%, 90%, or 95% identical to SEQ ID NO: 8
Sequences at least 70%, 75%, 80%, 85%, 90%, or 95% identical to SEQ ID NO: 9
Sequences at least 70%, 75%, 80%, 85%, 90%, or 95% identical to SEQ ID NO: 10

The synthetic intron variants are expected to have the same, substantially the same, or greater enhancing activity of SEQ ID NO:6, 7, 8, 9, or 10. For example, the activity of the variant to be tested is expected to be at least about 50%, 60%, 70%, 80%, 90%, 95%, 99%, 100%, 105%, 110% or more of the activity of SEQ ID NO: 6, 7, 8, 9, or 10.

Example 4

Preparation and Quantitative Root Expression Testing of Synthetic Promoter Elements Operably Linked to Native Expression Enhancing Intron Sequences in Stably Transformed *Arabidopsis*

To assess the activity of representative synthetic promoters from Example 1 in the presence of known enhancing introns, the AscI/RsrII promoter containing fragments were cloned into pGR799 and pGR687. pGR799 and pGR687 are derivatives of pGR716 that contain UTR-intron sequences from *Arabidopsis* genes AT4G37830 (SEQ ID NO: 13) and AT1G51650 (SEQ ID NO: 14), respectively, in front of the mGFP5-ER reporter of pGR716. These intron sequences and their enhancing properties have been previously described (see PCT/US2011/043197, herein incorporated by reference). All subsequent procedures were as described in Example 1.

GFP Expression Index (GEI) in *Arabidopsis* root tissue for four Synthetic nucleic acid molecules operably linked to the native enhancing introns were measured and shown in Table 5. GEIS in meristematic cells, elongation cells, and maturation cells were measured.

qRT-PCR was used to measure the relative expression levels of GFP in *Arabidopsis* aerial tissue for five synthetic nucleic acid molecules operably linked to native enhancing introns. The result is shown in Table 6.

Sequences of the native expression enhancing introns and operably linked synthetic introns-native expression enhancing introns are SEQ ID NO: 13 (IN1); SEQ ID NO: 14 (IN2); SEQ ID NO: 15 (SP1/IN2); SEQ ID NO: 16 (SP2/IN1); SEQ ID NO: 17 (SP2/IN2); SEQ ID NO: 18 (SP3/IN1); SEQ ID NO: 19 (SP3/IN2); SEQ ID NO: 20 (SP5/IN1).

TABLE 5

GFP Expression Index (GEI) in Arabidopsis Root Tissue for Four Synthetic Nucleic Acid Molecules Operably Linked to Native Enhancing Introns

| Promoter/ intron | Meristematic | | | | | | Elongation | | | | Maturation | | | |
|---|---|---|---|---|---|---|---|---|---|---|---|---|---|---|
|  | epi* | cor | end | ste | qc | cap | epi | cor | End | ste | epi | cor | end | ste |
| SP1/IN2-1 | 0.546 | 0.441 | 0.42 | 0.362 | 0.384 | 0.62 | 0.299 | 0.2 | 0.17 | 0.143 | 0.063 | 0.091 | 0.116 | 0.206 |
| SP1/IN2-2 | 0.45 | 0.348 | 0.328 | 0.273 | 0.326 | 0.594 | 0.282 | 0.182 | 0.144 | 0.12 | 0.064 | 0.085 | 0.103 | 0.197 |
| SP2/IN1-1 | 0.061 | 0.051 | 0.044 | 0.025 | 0.266 | 0.537 | 0.089 | 0.015 | 0.009 | 0.007 | 0.115 | 0.083 | 0.085 | 0.203 |
| SP2/IN1-2 | 0.038 | 0.042 | 0.035 | 0.02 | 0.233 | 0.242 | 0.061 | 0.014 | 0.008 | 0.007 | 0.062 | 0.043 | 0.042 | 0.099 |
| SP2/IN2-1 | 0.12 | 0.077 | 0.065 | 0.042 | 0.362 | 0.383 | 0.195 | 0.049 | 0.025 | 0.016 | 0.098 | 0.091 | 0.101 | 0.157 |
| SP2/IN2-2 | 0.156 | 0.102 | 0.083 | 0.047 | 0.551 | 0.618 | 0.222 | 0.042 | 0.022 | 0.015 | 0.138 | 0.092 | 0.098 | 0.144 |
| SP3/IN1-1 | 0.387 | 0.335 | 0.311 | 0.258 | 0.331 | 0.393 | 0.211 | 0.146 | 0.123 | 0.119 | 0.063 | 0.073 | 0.084 | 0.146 |
| SP3/IN1-2 | 0.714 | 0.637 | 0.609 | 0.505 | 0.51 | 0.68 | 0.297 | 0.204 | 0.169 | 0.151 | 0.064 | 0.073 | 0.097 | 0.208 |
| SP3/IN2-1 | 0.672 | 0.599 | 0.55 | 0.438 | 0.563 | 0.726 | 0.341 | 0.234 | 0.192 | 0.164 | 0.074 | 0.08 | 0.106 | 0.208 |

TABLE 5-continued

GFP Expression Index (GEI) in Arabidopsis Root Tissue for Four Synthetic Nucleic Acid Molecules Operably Linked to Native Enhancing Introns

| Promoter/ | Meristematic | | | | | | Elongation | | | | Maturation | | | |
|---|---|---|---|---|---|---|---|---|---|---|---|---|---|---|
| intron | epi* | cor | end | ste | qc | cap | epi | cor | End | ste | epi | cor | end | ste |
| SP3/IN2-2 | 0.218 | 0.198 | 0.178 | 0.141 | 0.152 | 0.185 | 0.105 | 0.075 | 0.062 | 0.053 | 0.029 | 0.03 | 0.036 | 0.063 |
| SP5/IN1-1 | 0.458 | 0.502 | 0.463 | 0.307 | 0.396 | 0.365 | 0.231 | 0.188 | 0.157 | 0.125 | 0.052 | 0.062 | 0.085 | 0.158 |
| SP5/IN1-2 | 0.312 | 0.279 | 0.26 | 0.193 | 0.266 | 0.316 | 0.135 | 0.106 | 0.088 | 0.072 | 0.031 | 0.035 | 0.047 | 0.095 |
| CaMV35S | 0.396 | 0.282 | 0.236 | 0.229 | 0.957 | 1 | 0.24 | 0.083 | 0.084 | 0.195 | 0.235 | 0.216 | 0.31 | 0.545 |

TABLE 6 qRT-PCR Expression Data in Arabidopsis Aerial Tissue fo Five Synthetic Nucleic Acid Molecules Operably Linked to Native Enhancing Introns

| Promoter/intron | Relative Expression |
|---|---|
| SP1/N2-1 | 21.0 |
| SP1/N2-2 | 21.4 |
| SP2/IN1-1 | 10.9 |
| SP2/IN1-2 | 6.3 |
| SP2/IN2-1 | nd* |
| SP2/IN2-2 | 2.6 |
| SP3/IN1-1 | 2.4 |
| SP3/IN1-2 | 7.8 |
| SP3/IN2-1 | 1.2 |
| SP3/IN2-2 | 11.0 |
| SP5/IN1-1 | 2.1 |
| SP5/IN1-2 | 2.9 | nd = not determined

These data demonstrate that the activity of synthetic promoters can be increased by operably linking enhancing introns to their 5'-UTR sequences (compare Tables 1 and 2 to Tables 5 and 6).

Example 5

Preparation and Quantitative Root Expression Testing of Synthetic Promoter Elements Operably Linked to Synthetic Enhancing Intron Sequences in Stably Transformed *Arabidopsis*

Synthetic introns can also be used to enhance the expression of synthetic promoters.

To assess the activity of representative synthetic promoters from Example 1 or functional variants thereof in the presence of the synthetic enhancing introns (e.g., SEQ ID NOs: 6-10, or functional variants therefore), or any synthetic enhancing intron previously described, the synthetic promoters from Example 1 or functional variants thereof can be operably linked to the synthetic enhancing introns or functional variants thereof of the present application. All subsequent procedures are as described in Example 1.

A non-limiting list of construct comprising sequences that can be tested is shown in Table 7.

TABLE 7

Constructs with Synthetic Promoters Operably Linked to Synthetic Introns

| Construct No. | Synthetic Promoter Sequence | Synthetic Intron Sequence |
|---|---|---|
| 1. | SEQ ID NO: 1, or at least 90% identical to SEQ ID NO: 1 | SEQ ID NO: 6, or at least 90% identical to SEQ ID NO: 6 |
| 2. | SEQ ID NO: 1, or at least 90% identical to SEQ ID NO: 1 | SEQ ID NO: 7, or at least 90% identical to SEQ ID NO: 7 |
| 3. | SEQ ID NO: 1, or at least 90% identical to SEQ ID NO: 1 | SEQ ID NO: 8, or at least 90% identical to SEQ ID NO: 8 |
| 4. | SEQ ID NO: 1, or at least 90% identical to SEQ ID NO: 1 | SEQ ID NO: 9, or at least 90% identical to SEQ ID NO: 9 |
| 5. | SEQ ID NO: 1, or at least 90% identical to SEQ ID NO: 1 | SEQ ID NO: 10, or at least 90% identical to SEQ ID NO: 10 |
| 6. | SEQ ID NO: 2, or at least 90% identical to SEQ ID NO: 2 | SEQ ID NO: 6, or at least 90% identical to SEQ ID NO: 6 |
| 7. | SEQ ID NO: 2, or at least 90% identical to SEQ ID NO: 2 | SEQ ID NO: 7, or at least 90% identical to SEQ ID NO: 7 |
| 8. | SEQ ID NO: 2, or at least 90% identical to SEQ ID NO: 2 | SEQ ID NO: 8, or at least 90% identical to SEQ ID NO: 8 |
| 9. | SEQ ID NO: 2, or at least 90% identical to SEQ ID NO: 2 | SEQ ID NO: 9, or at least 90% identical to SEQ ID NO: 9 |
| 10. | SEQ ID NO: 2, or at least 90% identical to SEQ ID NO: 2 | SEQ ID NO: 10, or at least 90% identical to SEQ ID NO: 10 |
| 11. | SEQ ID NO: 3, or at least 90% identical to SEQ ID NO: 3 | SEQ ID NO: 6, or at least 90% identical to SEQ ID NO: 6 |
| 12. | SEQ ID NO: 3, or at least 90% identical to SEQ ID NO: 3 | SEQ ID NO: 7, or at least 90% identical to SEQ ID NO: 7 |
| 13. | SEQ ID NO: 3, or at least 90% identical to SEQ ID NO: 3 | SEQ ID NO: 8, or at least 90% identical to SEQ ID NO: 8 |
| 14. | SEQ ID NO: 3, or at least 90% identical to SEQ ID NO: 3 | SEQ ID NO: 9, or at least 90% identical to SEQ ID NO: 9 |
| 15. | SEQ ID NO: 3, or at least 90% identical to SEQ ID NO: 3 | SEQ ID NO: 10, or at least 90% identical to SEQ ID NO: 10 |
| 16. | SEQ ID NO: 4, or at least 90% identical to SEQ ID NO: 4 | SEQ ID NO: 6, or at least 90% identical to SEQ ID NO: 6 |
| 17. | SEQ ID NO: 4, or at least 90% identical to SEQ ID NO: 4 | SEQ ID NO: 7, or at least 90% identical to SEQ ID NO: 7 |
| 18. | SEQ ID NO: 4, or at least 90% identical to SEQ ID NO: 4 | SEQ ID NO: 8, or at least 90% identical to SEQ ID NO: 8 |
| 19. | SEQ ID NO: 4, or at least 90% identical to SEQ ID NO: 4 | SEQ ID NO: 9, or at least 90% identical to SEQ ID NO: 9 |
| 20. | SEQ ID NO: 4, or at least 90% identical to SEQ ID NO: 4 | SEQ ID NO: 10, or at least 90% identical to SEQ ID NO: 10 |
| 21. | SEQ ID NO: 5, or at least 90% identical to SEQ ID NO: 5 | SEQ ID NO: 6, or at least 90% identical to SEQ ID NO: 6 |
| 22. | SEQ ID NO: 5, or at least 90% identical to SEQ ID NO: 5 | SEQ ID NO: 7, or at least 90% identical to SEQ ID NO: 7 |
| 23. | SEQ ID NO: 5, or at least 90% identical to SEQ ID NO: 5 | SEQ ID NO: 8, or at least 90% identical to SEQ ID NO: 8 |
| 24. | SEQ ID NO: 5, or at least 90% identical to SEQ ID NO: 5 | SEQ ID NO: 9, or at least 90% identical to SEQ ID NO: 9 |
| 25. | SEQ ID NO: 5, or at least 90% identical to SEQ ID NO: 5 | SEQ ID NO: 10, or at least 90% identical to SEQ ID NO: 10 |

GFP Expression Index (GEI) in *Arabidopsis* root tissue for these constructs can be measured. GEIS in meristematic cells, elongation cells, and maturation cells can be measured.

qRT-PCR can be used to measure the relative expression levels of GFP in *Arabidopsis* aerial tissue for five synthetic nucleic acid molecules operably linked to native enhancing introns.

The results will indicate that one or more pairs of synthetic promoter-synthetic introns lead to increased expression profiles.

Example 6

Preparation and Quantitative Root Expression Testing of Genetic Regulatory Elements and Expression-Enhancing Activity of Identified Synthetic Introns in Stably Transformed *Brassica* Species To assess promoter activity of the nucleic acid molecules of the present invention in stably transformed *Brassica* species, nucleic acid molecules comprising each of the nucleotide sequences set forth in Table 8 can be synthesized and cloned into a vector either by a contract DNA synthesis vendor or by the inventors. The fragment containing the synthetic sequences from the resulting plasmid can be excised and cloned into a binary vector suitable for *Brassica* species transformation, such as the vectors described by Bhalla et al., 2008 (*Agrobacterium*-mediated transformation of *Brassica napus* and *Brassica oleracea*, Nature Protocols, 3:181-189) or similar ones. *Brassica* plants can be transformed by using any method described in the above references. Each of the references mentioned above is hereby incorporated by reference in its entirety.

TABLE 8

Constructs with Synthetic Promoters and/or Synthetic Introns

| Construct No. | Synthetic Promoter Sequence | Synthetic Intron Sequence |
| --- | --- | --- |
| 1. | SEQ ID NO: 1, or at least 90% identical to SEQ ID NO: 1 | SEQ ID NO: 6, or at least 90% identical to SEQ ID NO: 6 |
| 2. | SEQ ID NO: 1, or at least 90% identical to SEQ ID NO: 1 | SEQ ID NO: 7, or at least 90% identical to SEQ ID NO: 7 |
| 3. | SEQ ID NO: 1, or at least 90% identical to SEQ ID NO: 1 | SEQ ID NO: 8, or at least 90% identical to SEQ ID NO: 8 |
| 4. | SEQ ID NO: 1, or at least 90% identical to SEQ ID NO: 1 | SEQ ID NO: 9, or at least 90% identical to SEQ ID NO: 9 |
| 5. | SEQ ID NO: 1, or at least 90% identical to SEQ ID NO: 1 | SEQ ID NO: 10, or at least 90% identical to SEQ ID NO: 10 |
| 6. | SEQ ID NO: 2, or at least 90% identical to SEQ ID NO: 2 | SEQ ID NO: 6, or at least 90% identical to SEQ ID NO: 6 |
| 7. | SEQ ID NO: 2, or at least 90% identical to SEQ ID NO: 2 | SEQ ID NO: 7, or at least 90% identical to SEQ ID NO: 7 |
| 8. | SEQ ID NO: 2, or at least 90% identical to SEQ ID NO: 2 | SEQ ID NO: 8, or at least 90% identical to SEQ ID NO: 8 |
| 9. | SEQ ID NO: 2, or at least 90% identical to SEQ ID NO: 2 | SEQ ID NO: 9, or at least 90% identical to SEQ ID NO: 9 |
| 10. | SEQ ID NO: 2, or at least 90% identical to SEQ ID NO: 2 | SEQ ID NO: 10, or at least 90% identical to SEQ ID NO: 10 |
| 11. | SEQ ID NO: 3, or at least 90% identical to SEQ ID NO: 3 | SEQ ID NO: 6, or at least 90% identical to SEQ ID NO: 6 |
| 12. | SEQ ID NO: 3, or at least 90% identical to SEQ ID NO: 3 | SEQ ID NO: 7, or at least 90% identical to SEQ ID NO: 7 |
| 13. | SEQ ID NO: 3, or at least 90% identical to SEQ ID NO: 3 | SEQ ID NO: 8, or at least 90% identical to SEQ ID NO: 8 |
| 14. | SEQ ID NO: 3, or at least 90% identical to SEQ ID NO: 3 | SEQ ID NO: 9, or at least 90% identical to SEQ ID NO: 9 |
| 15. | SEQ ID NO: 3, or at least 90% identical to SEQ ID NO: 3 | SEQ ID NO: 10, or at least 90% identical to SEQ ID NO: 10 |
| 16. | SEQ ID NO: 4, or at least 90% identical to SEQ ID NO: 4 | SEQ ID NO: 6, or at least 90% identical to SEQ ID NO: 6 |
| 17. | SEQ ID NO: 4, or at least 90% identical to SEQ ID NO: 4 | SEQ ID NO: 7, or at least 90% identical to SEQ ID NO: 7 |
| 18. | SEQ ID NO: 4, or at least 90% identical to SEQ ID NO: 4 | SEQ ID NO: 8, or at least 90% identical to SEQ ID NO: 8 |
| 19. | SEQ ID NO: 4, or at least 90% identical to SEQ ID NO: 4 | SEQ ID NO: 9, or at least 90% identical to SEQ ID NO: 9 |
| 20. | SEQ ID NO: 4, or at least 90% identical to SEQ ID NO: 4 | SEQ ID NO: 10, or at least 90% identical to SEQ ID NO: 10 |
| 21. | SEQ ID NO: 5, or at least 90% identical to SEQ ID NO: 5 | SEQ ID NO: 6, or at least 90% identical to SEQ ID NO: 6 |
| 22. | SEQ ID NO: 5, or at least 90% identical to SEQ ID NO: 5 | SEQ ID NO: 7, or at least 90% identical to SEQ ID NO: 7 |
| 23. | SEQ ID NO: 5, or at least 90% identical to SEQ ID NO: 5 | SEQ ID NO: 8, or at least 90% identical to SEQ ID NO: 8 |
| 24. | SEQ ID NO: 5, or at least 90% identical to SEQ ID NO: 5 | SEQ ID NO: 9, or at least 90% identical to SEQ ID NO: 9 |
| 25. | SEQ ID NO: 5, or at least 90% identical to SEQ ID NO: 5 | SEQ ID NO: 10, or at least 90% identical to SEQ ID NO: 10 |
| 26. | SEQ ID NO: 1, or at least 90% identical to SEQ ID NO: 1 | None |
| 27. | SEQ ID NO: 2, or at least 90% identical to SEQ ID NO: 2 | None |
| 28. | SEQ ID NO: 3, or at least 90% identical to SEQ ID NO: 3 | None |
| 29. | SEQ ID NO: 4, or at least 90% identical to SEQ ID NO: 4 | None |
| 30. | SEQ ID NO: 5, or at least 90% identical to SEQ ID NO: 5 | None |
| 31. | None | SEQ ID NO: 6, or at least 90% identical to SEQ ID NO: 6 |
| 32. | None | SEQ ID NO: 7, or at least 90% identical to SEQ ID NO: 7 |
| 33. | None | SEQ ID NO: 8, or at least 90% identical to SEQ ID NO: 8 |
| 34. | None | SEQ ID NO: 9, or at least 90% identical to SEQ ID NO: 9 |
| 35. | None | SEQ ID NO: 10, or at least 90% identical to SEQ ID NO: 10 |

To construct the transformation vector, the region between the left and right T-DNA borders of a backbone vector can be replaced with an expression cassette consisting of a constitutively expressed selection marker gene (e.g., the herbicide resistance gene) followed by a one or more of the expression elements listed in Table 8 operably linked to a reporter gene (e.g., GUS or GFP). The final constructs are transferred to *Agrobacterium* for transformation into *Brassica* species, e.g., *Brassica oleracea* (broccoli, cabbage, cauliflower, etc.), *Brassica rapa* (turnip, Chinese cabbage, etc.), and *Brassica napus* (rapeseed, etc.) plants by the method described in U.S. Published Patent Application No. 20110258740 to generate polynucleotide::GFP fusions in transgenic plants.

Pre-cultured healthy *Brassica* explants are immersed into bacteria liquid of *Agrobaterium* containing recombinant plasmid with constant oscillation to fully contact the bacteria liquid with explants. Spare bacteria liquid is quickly removed with aseptic filter paper. Then *Brassica* explants are layed flat onto co-culture medium to be co-cultivated for 2 days. To screen for transformed explants, *Brassica* explants are inoculated into differential medium (MS+2 mg/L of 6-BA, herbicide, 2.5 mg/L of AgNO$_3$ and 19.62 mg/L of AS) to continue the cultivation. Germ callus are obtained after 4 weeks of cultivation with the medium renewed by every 2 weeks.

The germ is sliced from callus tissue and transferred onto radication medium (½ MS, 0.15 mg/L of NAA and 250 mg/L of Cef) after both germ callus had grown up with 4-6 pieces of euphylla on screening culture medium (MS+2 mg/L of 6-BA, 2.5 mg/L of AgNO$_3$, 500 mg/L of Carb and 10 mg/L of Kan). The culture tank is moved outdoors for 2-3 d after the root system of regenerated seedlings grow well, followed by opening the tank and hardening seedlings for 2-3 d. Transgenic plants comprising desired transgene are cultivated respectively on radiation medium to develop the entire root system, and then transferred to pot culture. PCR is used to detect the transgenic *Brassica* plants.

Herbicide resistant *Brassica* plants (T1s) are selected. For example, the root tissues can be examined under the fluorescence microscope to determine the number of embryos with GFP expression. Plants are grown to maturity and seeds are harvested from individual plants. Quantitative results are produced by following the procedure described in Example 1. The results will indicate that one or more constructs listed in Table 8 are suitable for expression a gene in the root of a *Brassica* species.

Example 7

Preparation and Quantitative Root Expression Testing of Genetic Regulatory Elements and Expression-Enhancing Activity of Identified Synthetic Introns in Stably Transformed Soybean To assess promoter activity of the nucleic acid molecules of the present invention in stably transformed soybean, nucleic acid molecules comprising each of the nucleotide sequences set forth in Table 8 can be synthesized and cloned into a vector either by a contract DNA synthesis vendor or by the inventors. The fragment containing the synthetic sequences from the resulting plasmid can be excised and cloned into a binary vector suitable for soybean species transformation, such as the vectors and methods described by Yi et al. 2006 (Transformation of multiple soybean cultivars by infecting cotyledonary-node with *Agrobacterium tumefaciens*, African Journal of Biotechnology Vol. 5 (20), pp. 1989-1993, 16 Oct. 2006), Paz et al., 2004 (Assessment of conditions affecting *Agrobacterium*-mediated soybean transformation using the cotyledonary node explant, Euphytica 136: 167-179, 2004), U.S. Pat. Nos. 5,376,543, 5,416,011, 5,968,830, and 5,569,834, or by similar experimental procedures well known to those skilled in the art. Soybean plants can be transformed by using any method described in the above references.

To construct the transformation vector, the region between the left and right T-DNA borders of a backbone vector can be replaced with an expression cassette consisting of a constitutively expressed selection marker gene (e.g., the NptII kanamycin resistance gene) followed by one or more of the expression elements listed in Table 8 operably linked to a reporter gene (e.g., GUS or GFP). The final constructs are transferred to *Agrobacterium* for transformation into soybean plants by any of the methods described in Yi et al. 2006, Paz et al., 2004, U.S. Pat. Nos. 5,376,543, 5,968,830, and 5,569,834, or similar ones to generate polynucleotide:: β-glucuronidase (GUS) fusions in transgenic plants.

Soybean cotyledon explants of desired cultivars are prepared from seedlings obtained from germinated sterile seeds. The explant is inoculated with a smear of *A. tumefaciens* containing the construct of the present invention. β-glucuronidase (GUS) enzyme is included in the construct for detecting promoter activity. Selectable neomycin phosphotransferase marker gene (NOS/NPTII/NOS) is used for selection. Kanamycin resistance is assayed by the ability of leaf tissue to produce callus on medium containing MS salts, 2 mg/l BA, 0.5 mg/l NAA, 500 mg/l carbenicillin, 100 mg/l cefotaxime and 100 mg/l kanamycin. Whole or cut leaflets are placed on the medium, and if callusing occurred within 4 weeks, they are scored as resistant. Nontransgenic leaf tissue failed to callus on this medium. Transformed explant tissue is selected on media containing 200-300 mg/l kanamycin. Shoots from kanamycin resistant tissue are rooted and plantlets are obtained.

β-glucuronidase (GUS) enzyme activity in transformed soybean plants is analyzed as described. Root tissue of transgenic soybean plants is collected and stained in a histochemical reaction. After the histochemical reaction is complete, the plant tissue are fixed in FAA for 1 day and cleared in 70% ethanol. Quantitative results can be produced. The results will indicate that one or more constructs listed in Table 8 are suitable for expression a gene in the root of a soybean plant.

Example 8

Preparation and Quantitative Root Expression Testing of Genetic Regulatory Elements in Stably Transformed Corn To assess promoter activity of the nucleic acid molecules of the present invention in stably transformed corn, nucleic acid molecules comprising each of the nucleotide sequences set forth in Table 8 can be synthesized and cloned into a vector either by a contract DNA synthesis vendor or by the inventors. The fragment containing the synthetic sequences from the resulting plasmid can be excised and cloned into a binary vector suitable for corn transformation, such as the vectors described by Sidorov and Duncan, 2008 (*Agrobacterium*-Mediated Maize Transformation: Immature Embryos Versus Callus, Methods in Molecular Biology, 526:47-58), Frame et al., 2002 (*Agrobacterium tumefaciens*-Mediated Transformation of Maize Embryos Using a Standard Binary Vector System, Plant Physiology, May 2002, Vol. 129, pp. 13-22), Ahmadabadi et al., 2007 (A leaf-based regeneration and transformation system for maize (*Zea mays* L.), TransgenicRes. 16, 437-448), U.S. Pat. Nos. 6,420,630, 6,919,494 and 7,682,829, or similar experimental procedures well known to those skilled in the art. Corn plants are transformed by using any method described in the above references.

To construct the transformation vector, the region between the left and right T-DNA borders of a backbone vector can be replaced with an expression cassette consisting of a constitutively expressed selection marker gene (e.g., the herbicide resistance gene) followed by one or more of the expression elements listed in Table 8 operably linked to a reporter gene (e.g., GUS or GFP). The final constructs are transferred to *Agrobacterium* for transformation into corn plants by any of the methods described in Sidorov and Duncan, 2008, Frame et al., 2002, Ahmadabadi et al., 2007, U.S. Pat. Nos. 6,420,630, 6,919,494 and 7,682,829, or similar ones to generate polynucleotide:: GFP fusions in transgenic plants.

Ears containing immature embryos are harvested approximately 10 days after pollination. Immature embryos are isolated from surface sterilized ears and directly dropped into the prepared *Agrobacterium* cell suspension. After *Agrobacterium* cell suspension is removed using a fine tipped sterile transfer pipette, the immature embryos are transferred onto a co-culture medium. The embryos are placed on the medium with the scutellum side facing up. The embryos are cultured in a dark incubator for approximately 24 h. After the co-cultivation, the embryos are transferred onto a MS medium supplemented with herbicide in Petri dishes, 20 to 25 embryos per plate. The plates are kept in a dark culture room at 27° C. for approximately 2 weeks. At the end of 2 weeks, each piece of callus cultures from individual embryos is examined under a fluorescence stereomicroscope and the number of callus pieces with well-developed GFP-positive sectors is determined. All the callus pieces are then transferred individually onto a regeneration medium. The cultures are moved to a culture room with 16-h light/8-h dark photoperiod and 27° C. After 5-7 days, the callus pieces are transferred onto a second regeneration medium in Petri dishes. In another 2 weeks, the callus pieces that have shoots regenerated or are still alive are transferred onto the same hormone-free medium in Phytatrays for further growth.

Regenerated plants (R0) when they reach to the top of Phytatrays and have one or more healthy roots are moved to soil in pots in a growth chamber. In 7 to 10 days, they are transplanted into 12-in pots and moved to greenhouse with conditions for normal corn plant growth. The plants are either self-pollinated or crossed with wild-type plants.

Root tissues from some of the R0 plants are harvested at different times. The root tissues are examined under the fluorescence microscope to determine the number of embryos with GFP expression. In approximately 7 to 10 days, the number of embryos germinated to seedlings is also determined. Other plants are grown to maturity and seeds are harvested from individual plants. Quantitative results can be produced. The results will indicate that one or more constructs listed in Table 8 are suitable for expression a gene in the root of a corn plant.

Example 9

Preparation and Quantitative Root Expression Testing of Genetic Regulatory Elements in Stably Transformed Rice To assess promoter activity of the nucleic acid molecules of the present invention in stably transformed rice, nucleic acid molecules comprising each of the nucleotide sequences set forth in Table 8 can be synthesized and cloned into a vector either by a contract DNA synthesis vendor or by the inventors. The fragment containing the synthetic sequences from the resulting plasmid can be excised and cloned into a binary vector suitable for rice transformation, such as the vectors described by Lee et al., 2006 (Plastid transformation in the monocotyledonous cereal crop, rice (*Oryza sativa*) and transmission of transgenes to their progeny. *Mol. Cells* 21, 401-410), Toki et al., 2006 (*Agrobacterium*-mediated transformation of rice, The Plant Journal (2006) 47, 969-976), Nishimura et al., 2007 (A protocol for *Agrobacterium*-mediated transformation in rice, Nature Protocols 1, 2796-2802), Toriyama et al., 1985 (Cell suspension and protoplast culture in rice. Plant Science 41:179-183), Hiei, et al., 1994 (Efficient transformation of rice(*Oryza sativa* L.) mediated by *agrobacterium* and sequence analysis of the boundaries of the T-DNA. Plant J. 6:271-282), Christou 1997 (Rice transformation: bombardment, Plant Molecular Biology 35: 197-203, 1997.), Latha et al. 2006 (Tools for rice transformation: A flexible series of vectors harbouring phytohormone genes and specific promoters, Indian J. Crop Science, 1(1-2): 42-48 (2006)), U.S. Pat. Nos. 6,215,051, 6,329,571, or similar experimental procedures well known to those skilled in the art. Rice plants are transformed by using any method described in the above references.

To construct the transformation vector, the region between the left and right T-DNA borders of a backbone vector can be replaced with an expression cassette consisting of a constitutively expressed selection marker gene (e.g., the NptII kanamycin resistance gene) followed by a one or more of the expression elements listed in Table 8 operably linked to a reporter gene (e.g., GUS or GFP). The final constructs are transferred to *Agrobacterium* for transformation into rice plants by any of the methods described in Lee et al., 2006, Toki et al., 2006, Nishimura et al., 2007, Toriyama et al., 1985, Hiei, et al., 1994, Christou 1997, Latha et al. 2006, U.S. Pat. Nos. 6,215,051, 6,329,571, or similar ones to generate polynucleotide::GFP fusions in transgenic plants. At 10-12 days post-anthesis, seeds are dehulled, sterilized with 1% NaOCl and 1 drop of Tween-20 for 90 min., and washed extensively with sterile distilled water. Immature embryos are excised aseptically in a lamina flow bench. Excised embryos are placed on N6RD medium (Chan, M. T., et al (1992), supra) containing N6 salts (Chu, C. C., et al, Scientia Sinica 18: 659-668, 1975), N6 vitamins, 3% sucrose, 0.8% agarose (w/v), 2 µg/l 2,4-D, and cultured at 25° C. for 16 hours under light (1000 lux). Two days later, the immature embryos are inoculated with *Agrobacterium*. Calli are formed from the cultured embryos 3 weeks after *Agrobacterium* inoculation. The calli are transferred to N6RFB medium (similar to N6RF but containing 13 µg/ml 4-FPA, 1 µg/ml 6-benzylamino-purine (6-BAP), 40 µg/ml G-418 and 200 mg/ml cefotaxime) for selection of transformants. After selection for 3 weeks, calli are transferred to N6 medium for shoot regeneration and root development. Regenerated plants are eventually transferred to pot soil in the green-house and grown to self-pollination. Segregation of the kanamycin resistant phenotype in the progeny is analysed by germinating the R1 seeds on MS medium containing 300 µg/ml kanamycin. DNA from transgenic plants can be isolated according to the CTAB method (M. G. Murry and W. F. Thompson, Nucl. Acids Res. 8: 4321-4325, 1980). DNA bolt analysis can be performed as described by Maniatis et al (Molecular Cloning: A Laboratory Mannual, pressed by Cold Spring Harbor Laboratory 1982). To demonstrate the absence of any *Agrobacterium* contamination in the transformed plants, the same nylon filters hybridized with GFP DNA are stripped and rehybridized with a GFP probe.

Kanamycin resistant plants are either self-pollinated or crossed with wild-type plants. Root tissues from some of the R1 plants are harvested at different times for GFP expression analysis. The root tissues are examined under the fluorescence microscope to determine the number of embryos with GFP expression. Transgenic rice plants are grown to maturity and seeds are harvested from individual plants. Quantitative results can be produced. The results will indicate that one or more constructs listed in Table 8 are suitable for expression a gene in the root of a rice plant.

Example 10

Preparation and Quantitative Root Expression Testing of Genetic Regulatory Elements in Stably Transformed Wheat To assess promoter activity of the nucleic acid molecules of the present invention in stably transformed wheat, nucleic acid molecules comprising each of the nucleotide sequences set forth in Table 8 are synthesized and cloned into a vector either by a contract DNA synthesis vendor or by the inventors. The fragment containing the synthetic sequences from the resulting plasmid is then excised and cloned into a binary vector suitable for wheat transformation, such as the vectors described by Zhang et al., 2000 (An efficient wheat transformation procedure: transformed calli with long-term morphogenic potential for plant regeneration, Plant Cell Reports (2000) 19: 241-250), Cheng et al., 1997 (Genetic Transformation of Wheat Mediated by *Agrobacterium tumefaciens*, Plant Physiol. (1997) 115: 971-980), Abdul et al., (Genetic Transformation of Wheat (*Triticum aestivum* L): A Review, T G G 2010, Vol. 1, No. 2, pp 1-7), Pastori et al., 2000 (Age dependent transformation frequency in elite wheat varieties, J. Exp. Bot. (2001) 52 (357): 857-863), Jones 2005 (Wheat transformation: current technology and applications to grain development and composition, Journal of Cereal Science Volume 41, Issue 2, March 2005, Pages 137-147), Galovic et al., 2010 (MATURE EMBRYO-DERIVED WHEAT TRANSFORMATION WITH MAJOR STRESS MODULATED ANTIOXIDANT TARGET GENE, Arch. Biol. Sci., Belgrade, 62 (3), 539-546), or similar ones. Wheat plants are transformed by using any method described in the above references.

To construct the transformation vector, the region between the left and right T-DNA borders of a backbone vector is replaced with an expression cassette consisting of a constitutively expressed selection marker gene (e.g., the NptII kanamycin resistance gene) followed by one or more of the expression elements listed in Table 8 operably linked to a reporter gene (e.g., GUS or GFP). The final constructs are transferred to *Agrobacterium* for transformation into wheat plants by any of the methods described in Zhang et al., 2000, Cheng et al., 1997, Abdul et al., Pastori et al., 2000, Jones 2005, Galovic et al., 2010, U.S. Pat. No. 7,197,9964 or similar ones to generate polynucleotide::GFP fusions in transgenic plants.

Spring cultivars of wheat are grown in the greenhouse as described previously (Wan and Lemaux 1994; Lemaux et al. 1996) which are used as source of explants. Immature caryopses are collected approximately two weeks post anthesis, surface-sterilized with 20% bleach (5.25% sodium hypochlorite) and 0.1% Tween 20 for 30 min, and then washed five times with sterile double-distilled H2O. Immature embryos are isolated and placed with the scutellum side up on a callus induction medium as described by Weeks et al. (1993) with 1.5 mg/l of 2,4-D as the auxin source. Immature embryos are either used directly after dissection or incubated on callus induction. Wheat immature embryos or five-day-old embryogenic calli are washed twice in bacteria-free infection medium. Wheat explants are inoculated with *A. tumefaciens* strains EHA101, C58 or LBA4404 harboring the construct of the present invention and suspended in infection medium (MS salts with 150 mg/l L-asparagine, 1.5 mg/l 2,4-D, 68.4 g/l sucrose, 36.0 g/l glucose (pH 5.2) and supplemented with 100 µM acetosyringone (AS) before use). The tubes are incubated at room temperature for 5 min or 30 min. After infection the explants are transferred to the surface of co-cultivation medium. Embryos are oriented with the embryo-axis side in contact with the medium. Plates are wrapped and incubated in the dark at 22° C. for four days after which explants are transferred to resting medium. The number of embryogenic calli is determined as the number of co-cultivated immature embryos or calli that have initiated embryogenic calli after two weeks.

Selection of resistant clones is carried out by transferring wheat calli to selection medium containing kanamycin. Calli are incubated on this medium for two weeks before they are transferred to selection medium containing kanamycin. Putatively transformed events are regenerated on regeneration medium containing MS basal salts and vitamins, 2 mg/l TDZ, and solidified by 2 g/l phytagel. After two weeks, young wheat shoots are transferred to a rooting medium which contains half-strength MS basal salts and vitamins for 2-3 weeks. Well-rooted plants are transferred to the greenhouse potting mix soil:beatmos:sand (1:1:1).

Root tissue of transgenic wheat plants are harvested at different times for GFP expression analysis. The root tissues are examined under the fluorescence microscope to determine the number of embryos with GFP expression. Transgenic wheat plants are grown to maturity and seeds are harvested from individual plants. Quantitative results are produced. The results will indicate that one or more constructs listed in Table 8 are suitable for expression a gene in the root of a wheat plant.

Example 11

*Brassica* Breeding Program Using the Transgenic Plants Comprising the Synthetic Promoters and/or Synthetic Introns Non-limiting methods for *Brassica* breeding and agriculturally important traits (e.g., improving yield, biotic stress tolerance, and abiotic stress tolerance etc.) are described in, for example, Brown, J. and A. P Brown, 1997 (Gene transfer between canola (*Brassica napus* L. and *B. campestris* L.) Ann. Appl. Biol. 129:513-522); Montei, 1998, (Trend and perspectives of vegetable *brassica* breeding world-wide, World Conference on Horticultural Research, 1998); McCaughey et al., 2010 (Overview of *Brassica* Breeding and Genomics Research at AAFC); and Mark et al., 2005 (Breeding program for disease resistance in *Brassica* Crops, North Carolina Vegetable Growers Association).

A *brassica* plant comprising one or more synthetic promoters and/or synthetic introns of the present invention can be self-crossed to produce offspring comprising the same transgene.

A *brassica* plant comprising one or more synthetic promoters and/or synthetic introns of the present invention ("donor plant") can be also crossed with another plant ("recipient plant") to produce a F1 hybrid plant.

The F1 hybrid plants can be back-crossed to the recipient plant for 1, 2, 3, 4, 5, 6, 7, or more times. After each backcross, seeds are harvested and planted to select plants that comprise the synthetic promoter and/or synthetic intron, and preferred traits inherited from the recipient plant. Such selected plants can be used as either male or female plants to backcross with the recipient plants.

As a result, a new *brassica* plant can be produced which comprises all of the preferred traits inherited from the recipient plant along with the synthetic promoter and/or synthetic intron inherited from the donor plant.

Example 12

Soybean Breeding Program Using the Transgenic Plants Comprising the Synthetic Promoters and/or Synthetic Introns Non-limiting methods for soybean breeding and agriculturally important traits are described in, for example, Pathan and Sleper 2008 (Advances in Soybean Breeding, Plant Genetics and Genomics: Crops and Models, 2008, Volume 2, Part II, 113-133); Wilcox 1987 (Soybeans: improvement, production, and uses, American Society of Agronomy, 1987, ISBN 0891180907, 9780891180906); Singh, 2010 (The Soybean: Botany, Production and Uses, CABI, 2010, ISBN 1845936442, 9781845936440); Meghji, M. R., et al., 1984 (Inbreeding Depression, Inbred & Hybrid Grain Yields, and Other Traits of Maize Genotypes Representing Three Eras", *Crop Science*, Vol. 24, pp. 545-549); Openshaw et al. 1994, (Marker-assisted selection in backcross breeding". pp.

41-43.); Poehlman et al (1995) *Breeding Field Crop*, 4th Ed., Iowa State University Press, Ames, I A., pp. 132-155 and 321-344); and Werner et al., 2004 (Recurrent selection for yield in *Glycine max* using genetic male-sterility. Euphytica 50(1), 19-26) and U.S. Pat. No. 7,838,740.

A soybean plant comprising one or more synthetic promoters and/or synthetic introns of the present invention can be self-crossed to produce offspring comprising the same transgene.

A soybean plant comprising one or more synthetic promoters and/or synthetic introns of the present invention ("donor plant") can also crossed with another plant ("recipient plant") to produce a F1 hybrid plant.

The F1 hybrid plant can be back-crossed to the recipient plant for 1, 2, 3, 4, 5, 6, 7, or more times. After each backcross, seeds are harvested and planted to select plants that comprise the synthetic promoter and/or synthetic intron, and preferred traits inherited from the recipient plant. Such selected plants are used as either male or female plants to backcross with the recipient plants.

As a result, a new soybean plant can be produced which comprises all preferred traits inherited from the recipient plant and the synthetic promoter and/or synthetic intron inherited from the donor plant.

Example 13

Corn Breeding Program Using the Transgenic Plants Comprising the Synthetic Promoters and/or Synthetic Introns Non-limiting methods for corn breeding and agriculturally important traits are described in, for example, Allard, Principles of Plant Breeding, 1960; Simmonds, Principles of Crop Improvement, 1979; Fehr, "Breeding Methods for Cultivar Development", Production and Uses, 2nd ed., Wilcox editor, 1987, Carena et al., 2010 (Quantitative Genetics in Maize Breeding, Springer, 2010 ISBN 1441907653, 9781441907653); and Kriz and Larkins, 2008 (Molecular Genetic Approaches to Maize Improvement, Springer, 2008, ISBN 3540689192, 9783540689195).

A corn plant comprising one or more synthetic promoters and/or synthetic introns of the present invention can be self-crossed to produce offspring that comprising the same transgene.

A corn plant comprising one or more synthetic promoters and/or synthetic introns of the present invention ("donor plant") can also crossed with another plant ("recipient plant") to produce a F1 hybrid plant.

Some of the F1 hybrid plant can be back-crossed to the recipient plant for 1, 2, 3, 4, 5, 6, 7, or more times. After each backcross, seeds are harvested and planted to select plants that comprise the synthetic promoter and/or synthetic intron, and preferred traits inherited from the recipient plant. Such selected plants can be used as either male or female plant to backcross with the recipient plant.

As a result, a new corn plant can be produced which comprises all preferred traits inherited from the recipient plant and the synthetic promoter and/or synthetic intron inherited from the donor plant.

Example 14

Rice Breeding Program Using the Transgenic Plants Comprising the Synthetic Promoters and/or Synthetic Introns Non-limiting methods for rice breeding and agriculturally important traits are described in Virmani et al., (Two-Line Hybrid Rice Breeding Manual, International Rice Research Institute); Virmani 1997 (Hybrid Rice Breeding Manual, International Rice Research Institute, ISBN 9712201031, 9789712201035); Hu et al. (A draft sequence of the rice genome (*Oryza sativa* L. ssp. Indica) Science 296:79-92); Yang et al., 1996 (Theories and methods of rice breeding for maximum yield. Acta Agron. Sin. 22(3), 295-304); Wenfu et al. 2001, (Development of the new rice plant type and advances in research on breeding for super high yield. Rice research for food security and poverty alleviation. International Rice Research Institute, Manila, Philippines, pp. 43-50); Vaughan, 1994 (The wild relatives of rice, A genetic resources handbook. International Rice Research Institute, Manila, Philippines. pp. 1-137); and Guimaraes 2009 (Rice Breeding, M. J. Carena (ed.), Cereals, The Banks and the Italian Economy DOI: 10.1007/978-0-387-72297-9), and Datta 1981 (Principles and Practices of Rice Production, Int. Rice Res. Inst., 1981, ISBN 0471097608, 9780471097600).

A rice plant comprising one or more synthetic promoters and/or synthetic introns of the present invention can be self-crossed to produce offspring that comprising the same transgene.

A rice plant comprising one or more synthetic promoters and/or synthetic introns of the present invention ("donor plant") can also crossed with another plant ("recipient plant") to produce a F1 hybrid plant.

Some of the F1 hybrid plants can be back-crossed to the recipient plant for 1, 2, 3, 4, 5, 6, 7, or more times. After each backcross, seeds are harvested and planted to select plants that comprise the synthetic promoter and/or synthetic intron, and preferred traits inherited from the recipient plant. Such selected plants are used as either male or female plants to backcross with the recipient plants.

As a result, a new rice plant can be produced which comprises all preferred traits inherited from the recipient plant and the synthetic promoter and/or synthetic intron inherited from the donor plant.

Example 15

Wheat Breeding Program Using the Transgenic Plants Comprising the Synthetic Promoters and/or Synthetic Introns Non-limiting methods for wheat breeding and agriculturally important traits (e.g., improving wheat yield, biotic stress tolerance, and abiotic stress tolerance etc.) are described in Slafer and Araus, 2007, ("Physiological traits for improving wheat yield under a wide range of conditions", Scale and Complexity in Plant Systems Research: Gene-Plant-Crop Relations, 147-156); Reynolds ("Physiological approaches to wheat breeding", Agriculture and Consumer Protection. Food and Agriculture Organization of the United Nations); Richard et al., ("Physiological Traits to Improve the Yield of Rainfed Wheat: Can Molecular Genetics Help", published by International Maize and Wheat Improvement Center.); Reynolds et al. ("Evaluating Potential Genetic Gains in Wheat Associated with Stress-Adaptive Trait Expression in Elite Genetic Resources under Drought and Heat Stress Crop science", Crop Science 2007 47: Supplement 3: S-172-S-189); Setter et al., (Review of wheat improvement for waterlogging tolerance in Australia and India: the importance of anaerobiosis and element toxicities associated with different soils. Annals of Botany, Volume 103(2): 221-235); Foulkes et al., (Major Genetic Changes in Wheat with Potential to Affect Disease Tolerance. Phytopathology, July, Volume 96, Number 7, Pages 680-688 (doi:

10.1094/PHYTO-96-0680); Rosyara et al., 2006 (Yield and yield components response to defoliation of spring wheat genotypes with different level of resistance to *Helminthosporium* leaf blight. Journal of Institute of Agriculture and Animal Science 27. 42-48.); U.S. Pat. Nos. 7,652,204, 6,197,518, 7,034,208, 7,528,297, 6,407,311; U.S. Published Patent Application Nos. 20080040826, 20090300783, 20060223707, 20110027233, 20080028480, 20090320152, 20090320151; WO/2001/029237A2; WO/2008/025097A1; and WO/2003/057848A2.

A wheat plant comprising one or more synthetic promoters and/or synthetic introns of the present invention can be self-crossed to produce offspring that comprising the same transgene.

A wheat plant comprising one or more synthetic promoters and/or synthetic introns of the present invention ("donor plant") can also crossed with another plant ("recipient plant") to produce a F1 hybrid plant.

Some of the F1 hybrid plants can be back-crossed to the recipient plant for 1, 2, 3, 4, 5, 6, 7, or more times. After each backcross, seeds are harvested and planted to select plants that comprise the synthetic promoter and/or synthetic intron, and preferred traits inherited from the recipient plant. Such selected plants can be used as either male or female plant to backcross with the recipient plant.

As a result, a new wheat plant can be produced which comprises all preferred traits inherited from the recipient plant and the synthetic promoter and/or synthetic intron inherited from the donor plant.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the non-limiting exemplary methods and materials are described herein.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference. Nothing herein is to be construed as an admission that the present invention is not entitled to antedate such publication by virtue of prior invention.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A polynucleotide comprising a nucleotide sequence having at least 90% sequence identity to the nucleotide sequence set forth in SEQ ID NO: 1, wherein the nucleotide sequence comprises a SEQ ID NO: 39 (Site II sequence), a SEQ ID NO: 40 (telo box sequence) and a TATA box, wherein the nucleotide sequence is active as a promoter.

2. The polynucleotide of claim 1, wherein the nucleotide sequence comprises at least two telo box sequences and at least three Site II sequences.

3. The polynucleotide of claim 2, wherein the telo box sequences and Site II sequences are arranged, in a 5'-3' direction: telo box sequence, Site II sequence, telo box sequence, Site II sequence, Site II sequence, and TATA box sequence; wherein the telo box, Site II, and TATA box sequences are not contiguous.

4. The polynucleotide of claim 1, wherein the polynucleotide comprises at least 100 contiguous nucleotides of SEQ ID NO: 1.

5. The polynucleotide of claim 1, wherein the nucleotide sequence has at least 95% sequence identity to a nucleotide sequence set forth in SEQ ID NO: 1.

6. The polynucleotide of claim 1, wherein the nucleotide sequence has at least 99% sequence identity to a nucleotide sequence set forth in SEQ ID NO: 1.

7. A construct comprising at least one copy of said polynucleotide of claim 1, and an operably linked transcribable sequence of interest.

8. The construct of claim 7, wherein the nucleotide sequence has at least 95% sequence identity to a nucleotide sequence set forth in SEQ ID NO: 1.

9. The construct of claim 7, wherein the nucleotide sequence has at least 99% sequence identity to a nucleotide sequence set forth in SEQ ID NO: 1.

10. The construct of claim 7, wherein the construct comprises in the 5'-3' direction: (a) the at least one copy of said polynucleotide; (b) the operably linked transcribable sequence of interest; and (c) a gene termination sequence.

11. The construct of claim 7, wherein the transcribable sequence of interest comprises an open reading frame encoding a polypeptide.

12. A transgenic cell comprising the polynucleotide of claim 1.

13. The transgenic cell of claim 12, wherein the cell is a plant cell, an animal cell, a bacterial cell, an algae cell, or a fungal cell.

14. The transgenic cell of claim 12, wherein the cell is a plant cell.

15. An organism comprising the transgenic cell of claim 12, wherein the organism is a plant, a non-human animal, an algae, or a fungus.

16. The organism of claim 15, wherein the organism is a plant.

17. The organism of claim 15 or 16, wherein said polynucleotide is stably incorporated into the genome of the organism.

18. The organism of claim 15, wherein said polynucleotide is operably linked to a transcribable sequence of interest.

19. The organism of claim 16, wherein said plant is a monocot or a dicot.

20. The organism of claim 16, wherein said plant is selected from soybean, cotton, maize, sorghum, wheat, rice, switchgrass, sugarcane, millet, Brachypodium, and Arabidopsis.

21. A plant part of the plant of any one of claim 16, 19 or 20, wherein the plant part comprises the transgenic cell.

22. The plant part of claim 21, wherein the plant part is a seed.

23. A progeny plant of the plant of claim 16, wherein the progeny plant comprises said polynucleotide.

24. A method of expressing a gene of interest in a plant or plant cell, said method comprising incorporating into a plant cell, a construct comprising the polynucleotide of claim 1 operably linked to a transcribable nucleotide sequence of interest, wherein the polynucleotide is capable of driving the expression of the operably linked sequence of interest in the plant cell.

25. The method of claim 24, further comprising regenerating a transformed plant from said plant cell.

26. The method of claim 24, wherein said plant cell is stably transformed with said construct.

* * * * *

SEQUENCE LISTING

<160> NUMBER OF SEQ ID NOS: 59

<210> SEQ ID NO 1
<211> LENGTH: 500
<212> TYPE: DNA
<213> ORGANISM: Artificial Sequence
<220> FEATURE:
<223> OTHER INFORMATION: SP1

<400> SEQUENCE: 1

```
aaatagggtt tttctccccc cacggcccac cacggcccac ctaggcccac cctaaaaaaa      60
ccctaggtgg gtgggcccat tttttttttt tttttttttt ttttaggtgg ggtgggccgt     120 gggggaggt gggccgtggg cccatgaaaa aaaaaaaata gggttgggcc cacctaaaaa     180 aaaaaccta gggtgggccc aaaaaaaaaa aaaaaatgg gcccacccta tagggttttt     240
ttttttttta agagtccgga cttccagaag aataataatc tcggcccacg tctaaaaaag     300
aaaccaccca tccgtccatg ggcccacctc agaccggccc accaagacaa agcccaccaa     360
cggtgggccg gcccattggt tcacagtcac ggcccacggc ccacccggcc caccgctcta     420
taaaccctat ataagaaacc ctccacctcc tcgccctctt ggtttcctcc ctcttccgcc     480
gcacacaccc acccagagat                                                500
```

<210> SEQ ID NO 2
<211> LENGTH: 600
<212> TYPE: DNA
<213> ORGANISM: Artificial Sequence

```
<220> FEATURE:
<223> OTHER INFORMATION: SP2

<400> SEQUENCE: 2
gctagcgctt atggagcgtg atggactgaa agagacccct accacgtgtt gacgtaagca      60
atgacataaa accgatccta atctctccta cgaacgacag cggagagtac tgctgaaagc     120
tatgctttta tttttcttta tttttctcgt cagtggaata cacgttttgt cggtgtgtgt     180
ccttttccaa agaaagacgg aactgcctag gacaacgtcg gctaccaaag cacaatgtaa     240
agtagacatg atgatcgacg acgtcatgca tgacgtttaa catgcattgt atgtgtccgt     300
cagtctataa ataggtcaag aacaaacatc gagaaaaggc agaggcgaaa tacccatctg     360
cctatctctc aagaaataac tctctcttgt tcttcatcct ttctttcata gtttaaaaac     420
ctgaaattgg gcaagcccca taggcatttt ggtatcagag cgagtaagga caagtaggta     480
agtccctaaa atacttctat caataaaatt tctacgccaa gaagggtaag ttgtacgttt     540
atcctacacc cttgtgtttg taaccaggct tggtcaagtg cacaagggta tttgagtccc     600

<210> SEQ ID NO 3
<211> LENGTH: 500
<212> TYPE: DNA
<213> ORGANISM: Artificial Sequence
<220> FEATURE:
<223> OTHER INFORMATION: SP3

<400> SEQUENCE: 3
aacataactt gtatatttaa acataaagat aaaccttctt agagagaaca tatttaaatt      60
gtgttatcca ttacttttaa taaggaaata taatcttttc agtttgaatt gaaaataact     120
ttatcaaaat ttatgacaaa tacaaataaa aaccaaaaca caaaagaat tgtgtatatg     180 ttattgagaa acgatttta ttcactcgta catgattcat agaaaatttt aatttagtat     240
aaaaagtata aatataatat taatcaaata aattcttatg aaataaataa attcttcttc     300
aagggtaaat gaaaccttat gagtaaagtc tattctgcac ttaaaagaaa agagaattga     360
gtattttttg gaagcccatt tgggcccatt ttaaaatata ataagaaag cccaataatg     420 agaattaaaa accctagttt tcttcccctc ctatataaat cgacattttg ttcgttcctt     480
ctcttctctt ctcttcctct                                                 500

<210> SEQ ID NO 4
<211> LENGTH: 500
<212> TYPE: DNA
<213> ORGANISM: Artificial Sequence
<220> FEATURE:
<223> OTHER INFORMATION: SP4

<400> SEQUENCE: 4
aaattgttga tagaatttca aacataacat aacttaacat gaaatcttaa ttaattatca      60
gaaatacgat cactatcatc cgattttgtc ttttcgattt tattaatttt caactaaaac     120
atctcaacag ataaaacaaa accactttgt tgataatcca atattttaat tttattgaga     180
agatgatatg ataaagtata cagttatata caaaatgttt tctgcatatt tccaattttg     240
tcaaatgtca cttttaagtg tcaaacacta ataaaataaa ataaataaa taatacttgg     300 attaatgagt aaaaaaatgg gcctaaacaa attatatcac taaaaagtaa tttagaaatt     360
cataattggc ccatttgacc gagttttaa agctaaaatt ttaaaggccc aaaacccctta    420
```

```
ttagggtttc aacagaaacc tataaggaga ctctatataa accctctctt cgttcattag    480
ggtttctcct tctctgaaga                                                500
```

<210> SEQ ID NO 5
<211> LENGTH: 500
<212> TYPE: DNA
<213> ORGANISM: Artificial Sequence
<220> FEATURE:
<223> OTHER INFORMATION: SP5

<400> SEQUENCE: 5

```
acatttcggt tatctgggta ctacataaag attgccaagt ccattgattg aattgtgtgt     60
gtttttatgg ctcacttata cgttgtcttt tttaacaaaa aatgttttca actaatttga    120
attttgttta caaacaaata caaataacca ttggtttctc aagaatcaat caagaattag    180
aaatgatatg atagatttct caataaaaga caaaattttc aattttttca gttttttgtaa  240 atctacagca tcatttgtga tatgtctatc aaattttgct taaataaata aatcctcaaa    300
tactttgaat gagtaaaaat gaaataatta ggcttacata gtaattaaat aggcttcaaa    360
aaggctaagg cccaaatttg ttaaattaag aattgaagtc caaaaaccta tgttaaaaca    420
atctaggtta gggtttcttc tctcctatat attctataaa ctaggtcatt ccattcgtca    480
aactcctctc ttgcaaactc                                                500
```

<210> SEQ ID NO 6
<211> LENGTH: 307
<212> TYPE: DNA
<213> ORGANISM: Artificial Sequence
<220> FEATURE:
<223> OTHER INFORMATION: SI1

<400> SEQUENCE: 6

```
caggtaagtt tctcttcttc agctcttctt cttcttcttg gatctcgatt ttcgtgtaca     60
tttcgtagtt cgatctgatt ttcgttgttg atctagattc ttgcgatttg ggttttgttg    120
tgttgataat tttcttagtg atctgataga ttgtttatag tgtttcagat tgtttagaaa    180
tcttctatga atttaggttt gatcggtttc ttgatcgatt tgatgatttc tatcaattga    240
ttagtggatc tgttttgttg tgatttctaa tattgatctg ttttgtttgc ttttttccga    300
tgcaggt                                                              307
```

<210> SEQ ID NO 7
<211> LENGTH: 307
<212> TYPE: DNA
<213> ORGANISM: Artificial Sequence
<220> FEATURE:
<223> OTHER INFORMATION: SI2

<400> SEQUENCE: 7

```
caggtaaaat ttctcctctc ctttcctctc tctcttctga ttctgatttc gttttcgctc     60
gatttggatc gtatttgtcg ttagttttta atcgttggga ttcttggttg gtgtttgttt    120
gaattttcag ttgtagatct ttatagatct ctgtgtttta tgcatttaca tttaagattt    180
tagaaattgt tctagattgg tctttttgtt tagattcatc tgatcaattc aatgattgat    240
tgtttgaatt gtgatttgat aagtttctac tttgatctgt atattgattt gtttgttcct    300
tgcaggt                                                              307
```

```
<210> SEQ ID NO 8
<211> LENGTH: 305
<212> TYPE: DNA
<213> ORGANISM: Artificial Sequence
<220> FEATURE:
<223> OTHER INFORMATION: SI3

<400> SEQUENCE: 8
caggtttaca tctttattcc ttgtgttctc ttatacttga atctttcatt ttggttttcg    60
atttgggttt ttcgatttgt ttagattaat ctgattggag ctgtgtttat cattgtttcg   120
atctgtgata ttgaccaaat gatttgtgtt ttggttttct tagcttgtat tattattgat   180
tgaattcatt tcccattgat atttcgtttc tttttagcat tccaatctcc attgtttttt   240
ctgattatgc ttgtggatct ttacattttc aaaactttgt ggtctaatgt ttttttggtt   300
taggt                                                              305

<210> SEQ ID NO 9
<211> LENGTH: 310
<212> TYPE: DNA
<213> ORGANISM: Artificial Sequence
<220> FEATURE:
<223> OTHER INFORMATION: SI4

<400> SEQUENCE: 9
tcaaggtact actttctcat ccctctttca tacttttatt ctcttttgca ttttgatttg    60
gttttactct gagttttcta tctctcgatc tttgatttaa tctaattagg ttttttctag   120
atctagatct agatttgaaa atttaatagc tgttggtctt ccttgatttt tgtttagctt   180
gagttttatg tatagaatgg tgtttctctt tgaatctgtt gcatttctct tatgaatctg   240
attaatcttt tgatttgtgt ttatcgtttc ttaaataaac ttgttgtttg gttttgagtt   300
tgcagagagg                                                         310

<210> SEQ ID NO 10
<211> LENGTH: 308
<212> TYPE: DNA
<213> ORGANISM: Artificial Sequence
<220> FEATURE:
<223> OTHER INFORMATION: SI5

<400> SEQUENCE: 10
caggtaaact tttcttctcc tcttctagat ctctcttctc tcgatttctg aattatttcg    60
taatttccga tctctgattt ttggtgttag attttgtttt ctgtgatcga tttgatttga   120
ttttcagttg tagagtaaag cttgtttgtt gtttgagggt tagatatatc agattatgat   180
ttccgatatt gttgtttctc tgtttcgttt tgattcatca tcttatctgt ggatttagat   240
tatttagtgt gattcgtatg tactctgatt gaatttgtgt gatctttgtg tttggttttt   300
gtgcaggt                                                           308

<210> SEQ ID NO 11
<211> LENGTH: 857
<212> TYPE: DNA
<213> ORGANISM: Arabidopsis thaliana

<400> SEQUENCE: 11
tgcgagtggg cgaattccgg agcactctga ttggctgaaa aaatagaaat agtagtgatg    60
ttgctcctcc tctcctcctc tattattaat ttttcgtcgt tcttcttctg aaagttgtgt   120
ggttttagga ggtcaccaaa aaaaatctat tttgagatac taaaaatatt tcgttttgca   180
```

```
ttttgttgtg cagccatttg ttacacaggt tgaagcttat aactgaaaat tggattcaaa      240
gaatcgtaga tgaagaaatc gaagtgagtt gaatattttc tgaacatatg aaaattggaa      300 caagttttt ctcattttgc tagtttcctg tttttatgtt ttcttgactt taggagatga      360
catatggagg tgaactatac aaaggttgtt gcaacgataa cattctcctt aattcagttt      420
ttgcaactcg gttacaagca ctcagtggac ttttggccaa gacaattttt tttttttttt      480
ctctctctct aaaatgttat agatacgaat cctttgttga ataaggaaa aagttgaaca       540 tttgattaca cataagactt aacataatc caactttttt ttatatgaag ctacaaacaa       600
gatttaaaac atcaaagatt ccatctaaac ttcattcatc ttcaatcttc aacatccttc      660
aatgactagt atgtatgtac ataagtaaaa ttgttgataa gaaaacaaaa caatgatggg      720
ctaaaatagc ccataaaagg cccattaaac ttgggtttag actttagatt caacgacgcc      780
agattagtga gtcacataac cctcttggaa agagtctcaa cacttgcaga gaaaagaac       840 aaggaagatc ccggaaa                                                     857

<210> SEQ ID NO 12
<211> LENGTH: 815
<212> TYPE: DNA
<213> ORGANISM: Arabidopsis thaliana

<400> SEQUENCE: 12
ggaggaggat atgattgttg cttcaacaac tatatatgga tttgataaca atcctttatc       60
ctcggaagat aaaccaaatt tcttaccaaa cccaccaaaa taagtaatta ccagtgttct      120
tcttctaaag acttctataa accaaaacaa gatcacatat aatcattaac ttaaagcaaa      180
acccaaagtc ttgttttatt tgttagtcag ctcaaccatc tttatctgaa actaaactgt      240
ttctctcttc tttgtttctg acaagtcaat gagattggtg tcttctctct gttgcacatt      300
taatattaac ttttgaaaaa ctacaaaacg aaacaaaaca agaaaagca gacatttaca       360 cgaaattatg cagacatata cacgaaattc aatctacctg aaaatgagaa taagttttga      420
gtaaatttcg tggagactcc tggaaataag tttgtttgtt ttcctatttt tatgtaactt      480
cgcttaaatt tctaattgcc taatcaaggt attaaaatag caaagcttgg tttggctcag      540
tcttcgcgta aactccaaga aacaatcata aaaacaaata aaaagacaa gaaaccaaaa       600 aaaaaaaaa agttgagaga tttcagtaga tgaaagttgg atagaagatt cgtgtagtta      660
gctacttaat gggccgttaa atatttaat aaggcccatt gggtctaaac tgtgttagga       720
ttactagggc acagaatcgg tctctgtccc atttcgcgaa cttctccctt agaatcggaa      780
cggacgaaga aggaagacaa ggaagaagat cggag                                 815

<210> SEQ ID NO 13
<211> LENGTH: 421
<212> TYPE: DNA
<213> ORGANISM: Artificial Sequence
<220> FEATURE:
<223> OTHER INFORMATION: IN1

<400> SEQUENCE: 13
cagtgagtca cataaccctc ttggaaagag tctcaacact tgcagagaaa agaacaagg       60 aagatcccgg aaacaggtaa tttctctcct ctctattttt accattttcc attgacgacg      120
atctaggttt tctgatttga ttttggagaa cgcctcgatg agtttataga ttcgtagatt      180
ggttttgaga ttcagtataa tttcacccgg attccaattt ttgaaccgat acctaatttt      240
gaattgattt ggtagatcga ttggtcaaat ttgaaattga ttttttctcca taatatctga      300
```

| | | |
|---|---|---|
| agcgtcttat tggatcaaat ctacaacatt tctctgttga aaggatcgat ttttttttc | 360 | |
| ttggaacatg ataacttttg attattcatc aaagttttgt tctttttaat atttcacagg | 420 | |
| t | 421 | |

<210> SEQ ID NO 14
<211> LENGTH: 819
<212> TYPE: DNA
<213> ORGANISM: Artificial Sequence
<220> FEATURE:
<223> OTHER INFORMATION: IN2

<400> SEQUENCE: 14

| | | |
|---|---|---|
| cagatttcgc gaactttctc cttagaatcg gaacggacga agaaggaaga caaggaagaa | 60 | |
| gatcggaggt aagccttttc gatcctttaa tcgtcgatgt tggatcttag atctggattc | 120 | |
| ttcacgttct tgtgttctcg attcctgatt tgttttgag taatttgttg gaataatctg | 180 | |
| atttcctaaa agtatcgga attaagtgga aagtgaatca tctgcttctg gatttgatct | 240 | |
| tcgattttgc atttaaccttt tcctctgctt ctggatttga tcagttcaat actatcttca | 300 | |
| tacaatgttg ttatgtccaa attgttgaat ttttcattta gagttagctt cagagaaaac | 360 | |
| aacaaaacta gtagtatgtg tgaaacaaga acatgaagaa gatggaaagc tgattgggaa | 420 | |
| cattgcattt agatgtcttt tctcgtttat gtttggatct caattcttca tgttcttgtt | 480 | |
| gtgtgtcatt gaaattgttg gaatacgtag atatcagagt aggtcatttt gggaaagcta | 540 | |
| ttgaatttaa gaggaagatg aatcatttta acaagctcca tcgattttgc gcttaatctg | 600 | |
| tctctcttct gcttctggat ttgattaatt tcattctatt ttgttttctc ataagttgtt | 660 | |
| gttatgttca aattgttgaa tttggaatga tttcatttct caaatagggt ttactgagac | 720 | |
| aatgattcca gatttagtct atctgaaaat ggttcagctt tcttcttgtt gatccatttg | 780 | |
| tctaacattc tctcatgttt ttgttttttcc ttgacaggt | 819 | |

<210> SEQ ID NO 15
<211> LENGTH: 1326
<212> TYPE: DNA
<213> ORGANISM: Artificial Sequence
<220> FEATURE:
<223> OTHER INFORMATION: SP1/IN2

<400> SEQUENCE: 15

| | | |
|---|---|---|
| aaatagggtt tttctccccc cacggcccac cacggcccac ctaggcccac cctaaaaaaa | 60 | |
| ccctaggtgg gtgggcccat tttttttttt tttttttttt ttttaggtgg ggtgggccgt | 120 | |
| ggggggaggt gggccgtggg cccatgaaaa aaaaaaaata gggttgggcc cacctaaaaa | 180 | |
| aaaaacccta gggtgggccc aaaaaaaaaa aaaaaatgg gcccacccta tagggttttt | 240 | |
| tttttttta agagtccgga cttccagaag aataataatc tcggcccacg tctaaaaaag | 300 | |
| aaaccaccca tccgtccatg ggcccacctc agaccggccc accaagacaa agcccaccaa | 360 | |
| cggtgggccg gcccattggt tcacagtcac ggcccacggc ccaccggcc caccgctcta | 420 | |
| taaaccctat ataagaaacc ctccacctcc tcgccctctt ggtttcctcc ctcttccgcc | 480 | |
| gcacacaccc acccagagat cggaccgcag atttcgcgaa cttctccctt agaatcggaa | 540 | |
| cggacgaaga aggaagacaa ggaagaagat cggaggtaag ccttttcgat cctttaatcg | 600 | |
| tcgatgttgg atcttagatc tggattcttc acgttcttgt gttctcgatt cctgatttgt | 660 | |
| ttttgagtaa tttgttggaa taatctgatt tcctaaaagt tatcggaatt aagtggaaag | 720 | |
| tgaatcatct gcttctggat ttgatcttcg attttgcatt taacctttcc tctgcttctg | 780 | |

| | |
|---|---|
| gatttgatca gttcaatact atcttcatac aatgttgtta tgtccaaatt gttgaatttt | 840 |
| tcatttagag ttagcttcag agaaaacaac aaaactagta gtatgtgtga aacaagaaca | 900 |
| tgaagaagat ggaaagctga ttgggaacat tgcatttaga tgtcttttct cgtttatgtt | 960 |
| tggatctcaa ttcttcatgt tcttgttgtg tgtcattgaa attgttggaa tacgtagata | 1020 |
| tcagagtagg tcattttggg aaagctattg aatttaagag gaagatgaat cattttaaca | 1080 |
| agctccatcg atttttgcgct taatctgtct ctcttctgct tctggatttg attaatttca | 1140 |
| ttctattttg ttttctcata agttgttgtt atgttcaaat tgttgaattt ggaatgattt | 1200 |
| catttctcaa atagggttta ctgagacaat gattccagat ttagtctatc tgaaaatggt | 1260 |
| tcagctttct tcttgttgat ccatttgtct aacattctct catgttttttg ttttccttg | 1320 |
| acaggt | 1326 |

<210> SEQ ID NO 16
<211> LENGTH: 1028
<212> TYPE: DNA
<213> ORGANISM: Artificial Sequence
<220> FEATURE:
<223> OTHER INFORMATION: SP2/IN1

<400> SEQUENCE: 16

| | |
|---|---|
| gctagcgctt atggagcgtg atggactgaa agagacccct accacgtgtt gacgtaagca | 60 |
| atgacataaa accgatccta atctctccta cgaacgacag cggagagtac tgctgaaagc | 120 |
| tatgctttta ttttctttta tttttctcgt cagtggaata cacgttttgt cggtgtgtgt | 180 |
| ccttttccaa agaaagacgg aactgcctag gacaacgtcg gctaccaaag cacaatgtaa | 240 |
| agtagacatg atgatcgacg acgtcatgca tgacgtttaa catgcattgt atgtgtccgt | 300 |
| cagtctataa ataggtcaag aacaaacatc gagaaaggc agaggcgaaa tacccatctg | 360 |
| cctatctctc aagaaataac tctctcttgt tcttcatcct ttctttcata gtttaaaaac | 420 |
| ctgaaattgg gcaagcccca taggcatttt ggtatcagag cgagtaagga caagtaggta | 480 |
| agtccctaaa atacttctat caataaaatt tctacgccaa gaagggtaag ttgtacgttt | 540 |
| atcctacacc cttgtgtttg taaccaggct tggtcaagtg cacaagggta tttgagtccc | 600 |
| cggaccgcag tgagtcacat aaccctcttg gaaagagtct caacacttgc agagaaaaag | 660 |
| aacaaggaag atcccggaaa caggtaattt ctctcctctc tatttttacc attttccatt | 720 |
| gacgacgatc taggttttct gatttgattt tggagaacgc ctcgatgagt ttatagattc | 780 |
| gtagattggt tttgagattc agtataattt cacccggatt ccaattttttg aaccgatacc | 840 |
| taattttgaa ttgatttggt agatcgattg gtcaaatttg aaattgattt ttctccataa | 900 |
| tatctgaagc gtcttattgg atcaaatcta caacatttct ctgttgaaag gatcgatttt | 960 |
| ttttttcttg gaacatgata acttttgatt attcatcaaa gttttgttct ttttaatatt | 1020 |
| tcacaggt | 1028 |

<210> SEQ ID NO 17
<211> LENGTH: 1426
<212> TYPE: DNA
<213> ORGANISM: Artificial Sequence
<220> FEATURE:
<223> OTHER INFORMATION: SP2/IN2

<400> SEQUENCE: 17

| | |
|---|---|
| gctagcgctt atggagcgtg atggactgaa agagacccct accacgtgtt gacgtaagca | 60 |
| atgacataaa accgatccta atctctccta cgaacgacag cggagagtac tgctgaaagc | 120 |

-continued

```
tatgctttta ttttctttta tttttctcgt cagtggaata cacgttttgt cggtgtgtgt    180
ccttttccaa agaaagacgg aactgcctag gacaacgtcg gctaccaaag cacaatgtaa    240
agtagacatg atgatcgacg acgtcatgca tgacgtttaa catgcattgt atgtgtccgt    300
cagtctataa ataggtcaag aacaaacatc gagaaaaggc agaggcgaaa tacccatctg    360
cctatctctc aagaaataac tctctcttgt tcttcatcct ttctttcata gtttaaaaac    420
ctgaaattgg gcaagcccca taggcatttt ggtatcagag cgagtaagga caagtaggta    480
agtccctaaa atacttctat caataaaatt tctacgccaa gaagggtaag ttgtacgttt    540
atcctcacac cttgtgtttg taaccaggct tggtcaagtg cacaagggta tttgagtccc    600
cggaccgcag atttcgcgaa ctttctcctt agaatcggaa cggacgaaga aggaagacaa    660
ggaagaagat cggaggtaag cctttttcgat cctttaatcg tcgatgttgg atcttagatc    720
tggattcttc acgttcttgt gttctcgatt cctgatttgt ttttgagtaa tttgttggaa    780
taatctgatt tcctaaaagt tatcggaatt aagtggaaag tgaatcatct gcttctggat    840
ttgatcttcg attttgcatt taacctttcc tctgcttctg gatttgatca gttcaatact    900
atcttcatac aatgttgtta tgtccaaatt gttgaatttt tcatttagag ttagcttcag    960
agaaaacaac aaaactagta gtatgtgtga acaagaaca tgaagaagat ggaaagctga    1020
ttgggaacat tgcatttaga tgtcttttct cgtttatgtt tggatctcaa ttcttcatgt    1080
tcttgttgtg tgtcattgaa attgttgaaa tacgtagata tcagagtagg tcattttggg    1140
aaagctattg aatttaagag gaagatgaat cattttaaca agctccatcg attttgcgct    1200
taatctgtct ctcttctgct tctggatttg attaatttca ttctattttg ttttctcata    1260
agttgttgtt atgttcaaat tgttgaattt ggaatgattt catttctcaa atagggttta    1320
ctgagacaat gattccagat ttagtctatc tgaaaatggt tcagctttct tcttgttgat    1380
ccatttgtct aacattctct catgttttttg ttttccttg acaggt                   1426
```

<210> SEQ ID NO 18
<211> LENGTH: 928
<212> TYPE: DNA
<213> ORGANISM: Artificial Sequence
<220> FEATURE:
<223> OTHER INFORMATION: SP3/IN1

<400> SEQUENCE: 18

```
aacataactt gtatatttaa acataaagat aaaccttctt agagagaaca tatttaaatt     60
gtgttatcca ttacttttaa taaggaaata taatctttc agtttgaatt gaaaataact     120
ttatcaaaat ttatgacaaa tacaaataaa aaccaaaaca acaaaagaat tgtgtatatg    180
ttattgagaa acgatttta ttcactcgta catgattcat agaaaatttt aatttagtat     240
aaaaagtata aatataatat taatcaaata aattcttatg aaataaataa attcttcttc    300
aagggtaaat gaaaccttat gagtaaagtc tattctgcac ttaaaagaaa agagaattga    360 gtatttttg gaagcccatt tgggcccatt ttaaaatata ataagaaag cccaataatg      420 agaattaaaa accctagttt tcttcccctc ctatataaat cgacattttg ttcgttcctt    480
ctcttctctt ctcttcctct cggaccgcag tgagtcacat aaccctcttg gaaagagtct    540
caacacttgc agagaaaaag aacaaggaag atcccggaaa caggtaattt ctctcctctc    600
tatttttacc attttccatt gacgacgatc taggttttct gatttgattt tggagaacgc    660
ctcgatgagt ttatagattc gtagattggt tttgagattc agtataattt cacccggatt   720 ccaattttg aaccgatacc taatttgaa ttgatttggt agatcgattg gtcaaatttg     780
```

```
aaattgattt ttctccataa tatctgaagc gtcttattgg atcaaatcta caacatttct    840
ctgttgaaag gatcgatttt tttttcttg gaacatgata acttttgatt attcatcaaa     900
gttttgttct tttaatatt tcacaggt                                         928
```

```
<210> SEQ ID NO 19
<211> LENGTH: 1326
<212> TYPE: DNA
<213> ORGANISM: Artificial Sequence
<220> FEATURE:
<223> OTHER INFORMATION: SP3/IN2

<400> SEQUENCE: 19
```

```
aacataactt gtatatttaa acataaagat aaaccttctt agagagaaca tatttaaatt    60
gtgttatcca ttacttttaa taaggaaata taatctttc agtttgaatt gaaaataact    120
ttatcaaaat ttatgacaaa tacaaataaa aaccaaaaca acaaaagaat tgtgtatatg   180
ttattgagaa acgatttta ttcactcgta catgattcat agaaaatttt aatttagtat    240
aaaaagtata aatataatat taatcaaata aattcttatg aaataaataa attcttcttc   300
aagggtaaat gaaaccttat gagtaaagtc tattctgcac ttaaaagaaa agagaattga   360 gtatttttg gaagcccatt tgggcccatt ttaaaatata ataagaaag cccaataatg    420 agaattaaaa accctagttt tcttcccctc ctatataaat cgacattttg ttcgttcctt   480
ctcttctctt ctcttcctct cggaccgcag atttcgcgaa ctttctcctt agaatcggaa   540
cggacgaaga aggaagacaa ggaagaagat cggaggtaag cctttcgat cctttaatcg    600 tcgatgttgg atcttagatc tggattcttc acgttcttgt gttctcgatt cctgatttgt   660
ttttgagtaa tttgttggaa taatctgatt tcctaaaagt tatcggaatt aagtggaaag   720
tgaatcatct gcttctggat ttgatcttcg attttgcatt taacctttcc tctgcttctg   780
gatttgatca gttcaatact atcttcatac aatgttgtta tgtccaaatt gttgaatttt   840
tcatttagag ttagcttcag agaaaacaac aaaactagta gtatgtgtga acaagaaca    900 tgaagaagat ggaaagctga ttgggaacat tgcatttaga tgtctttttct cgtttatgtt   960 tggatctcaa ttcttcatgt tcttgttgtg tgtcattgaa attgttggaa tacgtagata  1020
tcagagtagg tcattttggg aaagctattg aatttaagag gaagatgaat cattttaaca  1080
agctccatcg attttgcgct taatctgtct ctcttctgct tctggatttg attaatttca  1140
ttctattttg ttttctcata agttgttgtt atgttcaaat tgttgaattt ggaatgattt  1200
catttctcaa atagggttta ctgagacaat gattccagat ttagtctatc tgaaaatggt  1260
tcagctttct tcttgttgat ccatttgtct aacattctct catgtttttg tttttccttg  1320
acaggt                                                             1326
```

```
<210> SEQ ID NO 20
<211> LENGTH: 928
<212> TYPE: DNA
<213> ORGANISM: Artificial Sequence
<220> FEATURE:
<223> OTHER INFORMATION: SP5/IN1

<400> SEQUENCE: 20
```

```
acatttcggt tatctgggta ctacataaag attgccaagt ccattgattg aattgtgtgt    60 gttttatgg ctcacttata cgttgtcttt tttaacaaaa aatgttttca actaatttga    120
attttgttta caaacaaata caaataacca ttggtttctc aagaatcaat caagaattag   180
aaatgatatg atagatttct caataaaaga caaaattttc aatttttca gttttgtaa    240
```

```
atctacagca tcatttgtga tatgtctatc aaattttgct taaataaata aatcctcaaa      300
tactttgaat gagtaaaaat gaaataatta ggcttacata gtaattaaat aggcttcaaa      360
aaggctaagg cccaaatttg ttaaattaag aattgaagtc caaaaaccta tgttaaaaca      420
atctaggtta gggtttcttc tctcctatat attctataaa ctaggtcatt ccattcgtca      480
aactcctctc ttgcaaactc cggaccgcag tgagtcacat aaccctcttg aaagagtct      540 caacacttgc agagaaaaag aacaaggaag atcccggaaa caggtaattt ctctcctctc      600 tattttacc attttccatt gacgacgatc taggttttct gatttgattt tggagaacgc      660
ctcgatgagt ttatagattc gtagattggt tttgagattc agtataattt cacccggatt      720 ccaattttg aaccgatacc taattttgaa ttgatttggt agatcgattg gtcaaatttg      780
aaattgattt ttctccataa tatctgaagc gtcttattgg atcaaatcta caacatttct      840
ctgttgaaag gatcgatttt ttttttcttg gaacatgata acttttgatt attcatcaaa      900
gttttgttct ttttaatatt tcacaggt                                        928

<210> SEQ ID NO 21
<211> LENGTH: 125
<212> TYPE: DNA
<213> ORGANISM: Artificial Sequence
<220> FEATURE:
<223> OTHER INFORMATION: SP3 bad70, -118 to +7 region

<400> SEQUENCE: 21
tgagacgtat atggcttccc gttaatcccc aatttaaaat ttatcacact tagccggatt       60
acgtgagtat aaaattctcg ccttcgtgcc ctcctttata gatcgagact ttttctttta      120
gttct                                                                  125

<210> SEQ ID NO 22
<211> LENGTH: 125
<212> TYPE: DNA
<213> ORGANISM: Artificial Sequence
<220> FEATURE:
<223> OTHER INFORMATION: SP3 bad80,-118 to +7 region

<400> SEQUENCE: 22
tgattatatt ttggaagccc atatggtgac atcttaaaat ataataaaga aatccgaata       60
atgcgagtta aacaccgtag ttttcttccc ctgtcatata gatcgacatt tagatcgttc      120
cttct                                                                  125

<210> SEQ ID NO 23
<211> LENGTH: 125
<212> TYPE: DNA
<213> ORGANISM: Artificial Sequence
<220> FEATURE:
<223> OTHER INFORMATION: SP3 bad90,-118 to +7 region

<400> SEQUENCE: 23
tgagtatttt tttgaagccc atatggcccc attttaaaat gtaataaagt aagcccaata       60
atgagaatta taaagcttag ttttctttca ctgctttata aatcgacctt tgttcgttc      120 cttcc                                                                  125

<210> SEQ ID NO 24
<211> LENGTH: 125
<212> TYPE: DNA
<213> ORGANISM: Artificial Sequence
<220> FEATURE:
<223> OTHER INFORMATION: SP3 good70,-118 to +7 region
```

```
<400> SEQUENCE: 24
tgggtattga ccggaagccc atttgggccc attttaattc tcaccaataa cggcccaata      60
ttgagaatta aaaaccctag ttctcttccc ctcctatata tatcgacatc gctgccattc     120
gttcc                                                                125

<210> SEQ ID NO 25
<211> LENGTH: 125
<212> TYPE: DNA
<213> ORGANISM: Artificial Sequence
<220> FEATURE:
<223> OTHER INFORMATION: SP3 good80,-118 to +7 region

<400> SEQUENCE: 25
tgagtattga tgggaagccc atttgggccc attttaagtt aagctaagga aagcccaata      60
gtgagaataa aaaccctag ttttcttccc ctcctatata aatcgacatt ttgttccttc      120
gttca                                                                125

<210> SEQ ID NO 26
<211> LENGTH: 125
<212> TYPE: DNA
<213> ORGANISM: Artificial Sequence
<220> FEATURE:
<223> OTHER INFORMATION: SP3 good90,-118 to +7 region

<400> SEQUENCE: 26
tgggtattca tgggaagccc atttgggccc attttaaaat ggggcaaata aagcccaata      60
atgagaataa aaaccctag ttttcttccc ctcctatata aatcgacatt tcattcgttc      120
cttct                                                                125

<210> SEQ ID NO 27
<211> LENGTH: 125
<212> TYPE: DNA
<213> ORGANISM: Artificial Sequence
<220> FEATURE:
<223> OTHER INFORMATION: SP4 bad70,-118 to +7 region

<400> SEQUENCE: 27
atcgctaatc aaccaagttg actcattttt ttaggcctaa atttcacagt tcctaccctc      60
tgattactgt tacaatagag tcctatagga attctctatc taaagctcgt gatcgttaca     120
caggg                                                                125

<210> SEQ ID NO 28
<211> LENGTH: 125
<212> TYPE: DNA
<213> ORGANISM: Artificial Sequence
<220> FEATURE:
<223> OTHER INFORMATION: SP4 bad80,-118 to +7 region

<400> SEQUENCE: 28
attcataagt ggctcatcta attgagtttt ttaagctaca attataaggg gccaacaccc      60
ttctttggct ttatacaata acctctaagg aggctctctt taaaccctct attcggtcat     120
taggc                                                                125

<210> SEQ ID NO 29
<211> LENGTH: 125
<212> TYPE: DNA
<213> ORGANISM: Artificial Sequence
<220> FEATURE:
<223> OTHER INFORMATION: SP4 bad90,-118 to +7 region
```

```
<400> SEQUENCE: 29
attcataagt aggctatatg agttagtttt taaagctata attttaaagg tccaaaaccc    60
ttcctaaggt ttcgacagaa acctataagg agactctata taactcctcc cttcgtgcat   120
taggg                                                               125

<210> SEQ ID NO 30
<211> LENGTH: 125
<212> TYPE: DNA
<213> ORGANISM: Artificial Sequence
<220> FEATURE:
<223> OTHER INFORMATION: SP4 good70,-118 to +7 region

<400> SEQUENCE: 30
ggccataatt ggcccattgg gtcgagtatt ttaagttaag gcccaaaagg cccaaaccct    60
aaattagggt ttcaaaccta gcctataagg agactctata aaaacccgcc tctcgttcat   120
taggg                                                               125

<210> SEQ ID NO 31
<211> LENGTH: 125
<212> TYPE: DNA
<213> ORGANISM: Artificial Sequence
<220> FEATURE:
<223> OTHER INFORMATION: SP4 good80,-118 to +7 region

<400> SEQUENCE: 31
gatcattatt ggcccatttt accgagttta ttaagctaaa attttaaagg cccaaaacct    60
atattagggt ttcaacagaa acctataagg agactatata taaactctcg tctcgttcat   120
taggg                                                               125

<210> SEQ ID NO 32
<211> LENGTH: 125
<212> TYPE: DNA
<213> ORGANISM: Artificial Sequence
<220> FEATURE:
<223> OTHER INFORMATION: SP4 good90,-118 to +7 region

<400> SEQUENCE: 32
attcataatt ggcccatttg accgagtttg taaagctaaa attttaaagg cccaaaaccc    60
agattagggt ttcaacagaa acctataagg agactctata taaactctct cttcgttcat   120
taggg                                                               125

<210> SEQ ID NO 33
<211> LENGTH: 125
<212> TYPE: DNA
<213> ORGANISM: Artificial Sequence
<220> FEATURE:
<223> OTHER INFORMATION: SP5 bad70,-118 to +7 region

<400> SEQUENCE: 33
aaaaacgcaa agcccgtagt tggttaatct cagagttgcg attgagaata atatatttaa    60
acagactcgg taggcgtcac ctctctccga ttgaatcagt aaactaaatc aacccttttct  120 ggaaa                                                               125

<210> SEQ ID NO 34
<211> LENGTH: 125
<212> TYPE: DNA
<213> ORGANISM: Artificial Sequence
<220> FEATURE:
<223> OTHER INFORMATION: SP5 bad80,-118 to +7 region
```

```
<400> SEQUENCE: 34
aaaaaggtca aggcttaaat tgttatatc aagtatttaa gtcaaaaaac ctatctttaa      60
ggaatcaagg ttaaggttgc ttaactccca tttatcctat aaacttggtc attccattcg    120
tcaaa                                                                125

<210> SEQ ID NO 35
<211> LENGTH: 125
<212> TYPE: DNA
<213> ORGANISM: Artificial Sequence
<220> FEATURE:
<223> OTHER INFORMATION: SP5 bad90,-118 to +7 region

<400> SEQUENCE: 35
aataaggcta aggcccaaat tgttaaatt aagaattgag gtccaaaaat ctatgttaga      60
acactgtagg tcggggtttc tactctcctg tatattcgat aaactcggtc attccattcg    120
tctaa                                                                125

<210> SEQ ID NO 36
<211> LENGTH: 125
<212> TYPE: DNA
<213> ORGANISM: Artificial Sequence
<220> FEATURE:
<223> OTHER INFORMATION: SP5 good70,-118 to +7 region

<400> SEQUENCE: 36
tacagggcta aggcccatta ttatttgggt aagaattgaa gccctaaggc aagggttaaa     60
acacaaccac ctagggtttc tctctcccta taaactatat aaacttgttc attttgttcg    120
ttcct                                                                125

<210> SEQ ID NO 37
<211> LENGTH: 125
<212> TYPE: DNA
<213> ORGANISM: Artificial Sequence
<220> FEATURE:
<223> OTHER INFORMATION: SP5 good80,-118 to +7 region

<400> SEQUENCE: 37
gatgggccta aggcccatta ttgtaagtta aagaattgaa gcccaaaccc tagaattaaa     60
acaatccata ttagggtttt gccgcaccta tatattctat aaactaggtc aactcttttcg   120 tcgaa                                                                125

<210> SEQ ID NO 38
<211> LENGTH: 125
<212> TYPE: DNA
<213> ORGANISM: Artificial Sequence
<220> FEATURE:
<223> OTHER INFORMATION: SP5 good90,-118 to +7 region

<400> SEQUENCE: 38
aaaacggcta aggcccaaat tgttaagtt aagaattgaa gtccaaagcc caatattaaa      60
acaatctacc ctagggtttc ttctctccta tatattctat aaactaggtc ttcccattgg    120
tcaaa                                                                125

<210> SEQ ID NO 39
<211> LENGTH: 8
<212> TYPE: DNA
<213> ORGANISM: Artificial Sequence
<220> FEATURE:
<223> OTHER INFORMATION: Site II, wherein r is a or g, and w is a or t
```

```
<400> SEQUENCE: 39 rgcccaww                                                              8

<210> SEQ ID NO 40
<211> LENGTH: 9
<212> TYPE: DNA
<213> ORGANISM: Artificial Sequence
<220> FEATURE:
<223> OTHER INFORMATION: telo box, wherein r is a or g

<400> SEQUENCE: 40 aaaccctar                                                             9

<210> SEQ ID NO 41
<211> LENGTH: 8
<212> TYPE: DNA
<213> ORGANISM: Artificial Sequence
<220> FEATURE:
<223> OTHER INFORMATION: TATA box, wherein w is a or t

<400> SEQUENCE: 41 tatawawa                                                              8

<210> SEQ ID NO 42
<211> LENGTH: 500
<212> TYPE: DNA
<213> ORGANISM: Artificial Sequence
<220> FEATURE:
<223> OTHER INFORMATION: SP3good90

<400> SEQUENCE: 42
taaataaatt gtctttgtca acataaagat aaaccttctt agagagaaca tatttaaatt     60
ttgttatcca ttacttttaa taaggaaaaa atatcttttc agtttgaatt gaaatccact    120
tcaaccacgc ttttgacaaa tacaaatcca aaccaaaaca acaaagaat tgtgtatatg     180 ttattgagaa acgattttc ttcactcgta catgattcgt acaaaatct aatttagtat      240 aaaaagtata tatataatat taatcaaata aagtcttatg aaataaatac attcttcttc   300
aagggtaaat gaaacctaat gagtaaagtc tattctgcac ttcaaagaaa atagaattgg   360
gtattcatgg gaagcccatt tgggcccatt ttaaaatggg gcaaataaag cccaataatg   420
agaataaaaa accctagttt tcttcccctc ctatataaat cgacatttca ttcgttcctt   480
ctcttctctt ctcttctttt                                               500

<210> SEQ ID NO 43
<211> LENGTH: 500
<212> TYPE: DNA
<213> ORGANISM: Artificial Sequence
<220> FEATURE:
<223> OTHER INFORMATION: SP4good90

<400> SEQUENCE: 43
aaattgttga tagaattccg aacagaacat aacttaactt gaaatataaa tcaattatca     60
gaaatacgtt cacgttcatc cgattttgtc ttttcgattg tataacttgt caacttcgac   120
atctcaacag ataaaacaaa accactttgt tgagaatcca aaactaggtt ttgattgaga   180
agatgatatg attcagaata cagttatata caaaatgttt tctgcatatt tccaattttg   240
tcaaatgtca ctattcattg tcaaacacta ttcaattaaa ttagatgaaa caatacttgg   300
attaatgagt taaaaaatgg gcctaagtta gttatatcac tcaaaagtaa ttgagcaatt   360
cataattggc ccatttgacc gagtttgtaa agctaaaatt ttaaaggccc aaaacccaga   420
```

```
ttagggtttc aacagaaacc tataaggaga ctctatataa actctctctt cgttcattag    480
ggtttctcct tctctgaaga                                                500
```

```
<210> SEQ ID NO 44
<211> LENGTH: 500
<212> TYPE: DNA
<213> ORGANISM: Artificial Sequence
<220> FEATURE:
<223> OTHER INFORMATION: SP5good90

<400> SEQUENCE: 44
attgctgggt tatctgggta ctacataaag attgccaagt ccattgatag aattgtgtgt    60
gttttgatgg ctcacttata cgttgtctgt tctaacaaaa tatgtttgca actaacttcg    120
attttatgaa caaacagata caaataacca ttggtttctc aagaatcctt caagagttag    180
aaatgatatg atagatttct caataaaaga caaaatttta cagttttttca gttttttgtaa    240 ctctacagca tcacttgtga tatgtctatc aaatttcgtt tgactaaata aatcctcaaa    300
tactttgaat gagtaaaaat gaataattaa ggcttaagta gtaatttgat aggcttcaaa    360
acggctaagg cccaaatttg ttaagttaag aattgaagtc caaagcccaa tattaaaaca    420
atctacccta gggtttcttc tctcctatat attctataaa ctaggtcttc ccattggtca    480
aactcctctc ttgcaaactc                                                500
```

```
<210> SEQ ID NO 45
<211> LENGTH: 500
<212> TYPE: DNA
<213> ORGANISM: Artificial Sequence
<220> FEATURE:
<223> OTHER INFORMATION: SP3good80

<400> SEQUENCE: 45
ttccaaactt gtatgttaga acataacata aaacctactt agagagagaa ttgcatgtga    60
ttgtgatcca ttacttttat ctgcgaaatc cgatttttttc agtttgaatt gaatgttact    120
ttatcaagac tcttgacaaa cacaaaattt cgccaaaaca acaaaagaat tgtgtatagg    180
tttttgagaa acgattttgg tgctctcgta catgattgga tggaaaatta aatttagtat    240
aaaaagtgtc actataatat gtgccaaaca tatacttatg aaataaataa attcttcttc    300
aagggtaaat gaatcctagt tggttaacgc aattctgcac tagatagaaa ggcctattga    360
gtattgatgg gaagcccatt tgggcccatt ttaagttaag ctaaggaaag cccaatagtg    420
agaataaaaa accctagttt tcttcccctc ctatataaat cgacattttg ttccttcgtt    480
cacttctctt ctcttcctct                                                500
```

```
<210> SEQ ID NO 46
<211> LENGTH: 500
<212> TYPE: DNA
<213> ORGANISM: Artificial Sequence
<220> FEATURE:
<223> OTHER INFORMATION: SP4good80

<400> SEQUENCE: 46
taattgttga gagaatccat aacataacat aacattacaa gaattctggt tcaaattgga    60
gaaatacttt agctgttttc tgttttttgtc ttttcgattg tttcagtttt caacttgaac    120
atctcaacag ataaaacgta accaacttgt tgagaatcca ataaaagaat ttgtttgaga    180
agatgatatg atagataaaa cagttatact caaaatgttt tctgcatatt tccaattttg    240
tcgaatgtca ctataaagtg tcaaacacta aagacagata aataaataat gattacttgg    300
```

| | |
|---|---|
| attgaggagc aaaaatttgg gcctaaacgc attaaaaacc tccctatcaa ggcccaagat | 360 |
| cattattggc ccatttttacc gagtttatta agctaaaatt ttaaaggccc aaaacctata | 420 |
| ttagggtttc aacagaaacc tataaggaga ctatatataa actctcgtct cgttcattag | 480 |
| ggtttctctt gctcataaga | 500 |

```
<210> SEQ ID NO 47
<211> LENGTH: 500
<212> TYPE: DNA
<213> ORGANISM: Artificial Sequence
<220> FEATURE:
<223> OTHER INFORMATION: SP5good80

<400> SEQUENCE: 47
```

| | |
|---|---|
| atgtctgtgt tatctgggta ctacataaag aggcccaagt caattgagag aactgtgtgt | 60 |
| gtgttgatgg ctcacttcta cgttgagttt tttaacaaaa aatcatttca actagtttga | 120 |
| atttaacaaa caaacagata gaaataacca ttggtctctc aagaatcatt caagtataga | 180 |
| agatgatatg atagatttct ctaccaaaga caaaattgtc gtatttgtca gttttttgtaa | 240 |
| atctacagct tcatttgtga tatgtctatc aaagcttgaa taattaaatt tttcctcaaa | 300 |
| tccttggcct gagtaaaaat gaaaagaaaa ggcttacata gtaattttat aggcttagat | 360 |
| gggcctaagg cccattattg taagttaaag aattgaagcc caaaccctag aattaaaaca | 420 |
| atccatatta gggttttgcc gcacctatat attctataaa ctaggtcaac tctttcgtcg | 480 |
| aacccttctc ttgcaaactc | 500 |

```
<210> SEQ ID NO 48
<211> LENGTH: 500
<212> TYPE: DNA
<213> ORGANISM: Artificial Sequence
<220> FEATURE:
<223> OTHER INFORMATION: SP3good70

<400> SEQUENCE: 48
```

| | |
|---|---|
| acgagacttt gttttgagtg agttgaagat aaacgttgag atagagagat gtgtgtgtgt | 60 |
| tttttatcca tcacttagcc aaatgcacaa aaatgttttc agtttgaatt ggacttcgct | 120 |
| tttccatcct tgttgacaaa tacaaatata atccaataca aaacgatcag aattagtttt | 180 |
| cctttttagaa acgatttaga ttctctcgta catgattgga dacaacatcc aatttaataa | 240 |
| acaaagtaat tcattgttac tattcaaaca cagccgtgag agataaatac attcttcttc | 300 |
| aagggtaaat gaaagccaat gagttaagtc tattctgcac taaaagcaaa atagaattgg | 360 |
| gtattgaccg gaagcccatt tgggcccatt ttaattctca ccaataacgg cccaatattg | 420 |
| agaattaaaa accctagttc tcttcccctc ctatatatat cgacatcgct gccattcgtt | 480 |
| cctctcttct cttctcttcc | 500 |

```
<210> SEQ ID NO 49
<211> LENGTH: 500
<212> TYPE: DNA
<213> ORGANISM: Artificial Sequence
<220> FEATURE:
<223> OTHER INFORMATION: SP4good70

<400> SEQUENCE: 49
```

| | |
|---|---|
| ccattgttga gagaatccat aacataacat aactgtgact taactgatct tcctgtgagt | 60 |
| gaaatactta tcacttcatc cgatttttgtt tttgcgatag tagttactct caacttcgac | 120 |
| atctcaacag ataagataat acagaaatag tgagaatcca aaacgaacat cagtttgaga | 180 |

```
agatgatatg ataacaagta cagttgaagt gaaaatcttt tctgcatttt taaaatcttc    240
acgaatgtca ctaatctatg tcaaacacta ttcactgaaa tacgatttgg tgatactttg    300 aggaagggt taaaaatgg gcctaaactc taaaacacac taaaaaggcg tttaataggc      360
cataattggc ccattgggtc gagtatttta agttaaggcc caaaaggccc aaaccctaaa    420
ttagggtttc aaacctagcc tataaggaga ctctataaaa acccgcctct cgttcattag    480
ggtttctctt cttctgaaga                                                500

<210> SEQ ID NO 50
<211> LENGTH: 500
<212> TYPE: DNA
<213> ORGANISM: Artificial Sequence
<220> FEATURE:
<223> OTHER INFORMATION: SP5good70

<400> SEQUENCE: 50
acttttccgt attctgggta cttcagtaag attgccaagt ccagatagag aactgagtgt     60
gtgttgatgg ctcacttata cgttttctgt tttaacagag aaaaatttca acttgagtga    120
atgtacgaaa tcaacagata catagattca ttggtctctc aagaataatc aaaatataag    180
gaatgatatg ttagattttt ctcatagatt caactttac attttttgtca gttttttgttc    240 ctctacagca ccacgcgtgt tttgtgtttc aaagtcttta tgattaaatc ctcccacaaa    300
tcctttaaat gagtaaaaaa gcaacgtaaa ggctttagta gaaatttgat aggcctttac    360
agggctaagg cccattatta tttgggtaag aattgaagcc ctaaggcaag ggttaaaaca    420
caaccaccta gggtttctct ctccctataa actatataaa cttgttcatt tgttcgttc     480 ctctcttctc ttgcaaactc                                                500

<210> SEQ ID NO 51
<211> LENGTH: 500
<212> TYPE: DNA
<213> ORGANISM: Artificial Sequence
<220> FEATURE:
<223> OTHER INFORMATION: SP3bad90

<400> SEQUENCE: 51
aacataactt gtatatgtaa agatgaatgt aaaccttctt agagaggaca tatataaatt     60
gtgttatcca ttacttttaa taaggaaatc caagcttttc aggtccaatt gaaaataagt    120
ttatcaaaat ttatgaaaat tacaaataaa aaccaaaaca accaaagaat tatgtatatc    180
ttatggtgga acgattatta ttcactcgta catgattcat agcaaatttt aattgattac    240
aaaaagtata aatataatat taataaaata aacgcttatg aaaaagataa attcttcttc    300
aaggccaaat gaaccttat gagtaacgtc tattctgcac ttaaaaaaaa agagaattga    360 gtatttttt gaagcccata tggcccccatt ttaaaatgta ataagtaag cccaataatg    420 agaattataa agcttagttt tctttcactg ctttataaat cgaccttttg ttcgttcctt    480
cccttctctt atcttcatct                                                500

<210> SEQ ID NO 52
<211> LENGTH: 500
<212> TYPE: DNA
<213> ORGANISM: Artificial Sequence
<220> FEATURE:
<223> OTHER INFORMATION: SP4bad90
```

```
<400> SEQUENCE: 52
aaattgttga tagaatttca aacataatat aactgaacat taaatcttaa ttaattatca      60
gaaatatgat cactataatc cgactttgtc tttcggattt tattaatttt caactaaaaa     120
atctcaacag ataaaacaaa cctactctgt cgataatcca atattttaat tttattgaga     180
agctcatatg acaacgtgta cagatatcta caaaatgttt tctacatatt tccaattttg     240
tcacatgtca attttaagtg tcaaacacta ataaaataaa ctaaattaga ttattttcgt     300
attaatgagt aaaaaaatgg gcctaaacaa attgtatcac taaaaagtaa tttagaaatt     360
cataagtagg ctatatgagt tagttttttaa agctataatt ttaaaggtcc aaaacccttc    420
ctaaggtttc gacagaaacc tataaggaga ctctatataa ctcctcccttt cgtgcattag    480 ggtatctcat tctctgaaga                                                  500

<210> SEQ ID NO 53
<211> LENGTH: 500
<212> TYPE: DNA
<213> ORGANISM: Artificial Sequence
<220> FEATURE:
<223> OTHER INFORMATION: SP5bad90

<400> SEQUENCE: 53
actgttcggt tgtctgggtt ctacataaag attaccaagt ccattgattg tattgcgtgt      60 tttttttgtgg cgcacttata cgttgtattt tgtaacgaaa aatgtttcca actaatttga    120
attttgtttc caaacaactt caaataatca ttggtttctc aagagtcaac caagaattag     180
aaatggtatg atagatttct caataaacaa caaaattgtc aatttttatca gttttggtga    240 agctacagca tcatttgtga tctgtctttc aaattttgct taaataaata aatcctcaaa     300
tagttggaat gagtaaaaat gaataattaa ggcttacata gtatttaaat aggcttcaat     360
aaggctaagg cccaaatttg ttaaattaag aattgaggtc caaaaatcta tgttagaaca     420
ctgtaggtcg gggtttctac tctcctgtat attcgataaa ctcggtcatt ccattcgtct     480
aactaatctc tcgcaaactc                                                  500

<210> SEQ ID NO 54
<211> LENGTH: 500
<212> TYPE: DNA
<213> ORGANISM: Artificial Sequence
<220> FEATURE:
<223> OTHER INFORMATION: SP3bad80

<400> SEQUENCE: 54
aacatcaagc gtgcatttaa acataaagat aaaccatctt agagagcaca tatctaaatt      60
gtgttagtca tcacctttaa ttagtatata tgatctttttc actaccaatg gaggattact    120
ttagctcaat ttatgggact ggcataggat atccaaaaca ataacagaac tgtggctatg     180
caaatgggga acgattttta ttcacttgtg catgatttct agaaggtttt tattttgtat     240
aaaaagtata aacataatat taatcaaata aatgcttttg aaatacataa atacttctgc     300
aagggtaaat gcaacctaat ctgtaacgtc tattctgctt gtaagaaaat agagatgtga     360
ttatattttg gaagcccata tggtgacatc ttaaaatata ataagaaat ccgaataatg      420 cgagttaaac accgtagttt tcttcccctg tcatatagat cgacatttag atcgttcctt     480
ctcttaggct gtcttcctct                                                  500
```

```
<210> SEQ ID NO 55
<211> LENGTH: 500
<212> TYPE: DNA
<213> ORGANISM: Artificial Sequence
<220> FEATURE:
<223> OTHER INFORMATION: SP4bad80

<400> SEQUENCE: 55
aaatcgctgt tataatttca aacataacag accataaaat taaattttac ttaattctca      60
tatatacgat aactatcatc ctatgttgtg ttttcgctat tattaatctt caactaaatc     120
atataaattg gcaaggcaaa cccactttt tgataatcca atcttttaat tttattgaga      180
aggttatatg ctaaagtata ccgttatata caaaatgctt tctccatatt tgagattgtg     240
ttggaagtcc cacttaggtg tcgaacgcta aaaaaatcaa atatcgtaac tcatactttg     300
attaatgagt actaccatgg tcctaaacaa atgataacaa taagaagtaa tttagaaatt     360
cataagtggc tcatctaatt gagtttttta agctacaatt ataagggggcc aacacccttc    420 tttggcttta tacaataacc tctaaggagg ctctctttaa accctctatt cggtcattag     480
gctcttgcct tctctgaaga                                                 500

<210> SEQ ID NO 56
<211> LENGTH: 500
<212> TYPE: DNA
<213> ORGANISM: Artificial Sequence
<220> FEATURE:
<223> OTHER INFORMATION: SP5bad80

<400> SEQUENCE: 56
acactcggat tatttgagta ctccattagg attgccgtct ccctagattg aattatgtgt      60 gatttttctcg cccacttgta cgttgtcttg ttccacaaaa aatctttttt attaatttga    120
ctatcgtttc taaacaaata cacataacga ttggatcccc tagagtcaat gaagaattac     180
aaatgatatg gtagatttct aaagaaaaga caaaattgtc atttttttca gtgtatgtat     240
atcttcagag ccatttgtgt taggtctagc aagttctgct taaataaata aatcctcata    300
tacttagagt gcctaaaaag taaagtatta gtcttaaatg gtcgttagac taaccccaaa    360
aaggtcaagg cttaaatttg ttatatcaag tatttaagtc aaaaaaccta tctttaagga    420
atcaaggtta aggttgctta actcccattt atcctataaa cttggtcatt ccattcgtca   480
aattccgctc ttgcaaattc                                                 500

<210> SEQ ID NO 57
<211> LENGTH: 500
<212> TYPE: DNA
<213> ORGANISM: Artificial Sequence
<220> FEATURE:
<223> OTHER INFORMATION: SP3bad70

<400> SEQUENCE: 57
aacctaattt gcgtatacaa atatagcgat tcaccttctt agaaacaaca tacttagtag     60
gtgtcataaa gtgcatgtaa taaggatgta taatcttttt attctgaatt ttagataaca    120
ctattaatat taatgacaaa tataaacaga atcatagaca caacaagcaa ggagtaaatg    180
ggatcgagaa acgattttc tttactcgta cgtcatcgat agaaacttag aacgccctct    240
caaacgttta agtataatac caaccagaca aattcacatg aagttaaaaa atacttcttt    300
tggggtaaat gaaacctaac gaggaaagcc ttttcgctac ttaaacataa agagacatga   360
gacgtatatg gcttcccgtt aatccccaat ttaaaattta tcacacttag ccggattacg    420
```

```
tgagtataaa attctcgcct tcgtgccctc ctttatagat cgagactttt ttctttagtt    480
ctagcttctt gactatcctt                                                500

<210> SEQ ID NO 58
<211> LENGTH: 500
<212> TYPE: DNA
<213> ORGANISM: Artificial Sequence
<220> FEATURE:
<223> OTHER INFORMATION: SP4bad70

<400> SEQUENCE: 58
caattgctga aagaatttca gtcataacat aactcaacat gatttcctaa tccactattt     60
aatatacgtg ccccatcctc caggttagtc tcctcgcctt gagtaatttt taagtataaa    120
atcatgacag atgaaagaaa tgcactttgg tgaggatcca atattgtaat ataatttaga    180
cattgatatg aaaaaggctt caagtattta cataaggact catgcatata ttgaatttcg    240
cttagcgtca gtctcgcagc tgaaagacta ataaaataca atacgataaa taatacttgg    300
attaatgagt acaaaaatac gcctagtcga ctgtgatttg gcaaaaataa tttagaaatc    360
gctaatcaac caagttgact cattttttta ggcctaaatt tcacagttcc taccctctga    420
ttactgttac aatagagtcc tataggaatt ctctatctaa agctcgtgat cgttacacag    480
ggtgtcactt tctgtgaaaa                                                500

<210> SEQ ID NO 59
<211> LENGTH: 500
<212> TYPE: DNA
<213> ORGANISM: Artificial Sequence
<220> FEATURE:
<223> OTHER INFORMATION: SP5bad70

<400> SEQUENCE: 59
aggtcggacc tatcttggga cgacatagcc attgccaata ggcacaatcg tattctgtgc     60
gttttaatgg ctcccttatt gtttgccttt tttaaaaaga tatctgttca cctaattgct    120
attatgttca cgcacacttt ccaagaacga taggtatctc aagaaacagt caataagtag    180
aactactatg atagtcatct tattaaaaga ccaaatcttg aatcttttca gttttttga    240 atctatagca tctttggggt tacgtctttc aaccatggct taaataaaaa cttgcgcaaa    300
aactttggat tgctaaatat aaacttatta tcggtacatg gtgattataa aggcttcaaa    360
aacgcaaagc ccgtagttgg ttaatctcag agttgcgatt gagaataata tatttaaaca    420
gactcggtag gcgtcacctc tctccgattg aatcagtaaa ctaaatcaac cctttctgga    480
aaccgctctc ctgcaaacgc                                                500
```